United States Patent
Cha et al.

(10) Patent No.: US 12,114,562 B2
(45) Date of Patent: Oct. 8, 2024

(54) COMPOUND FOR ORGANIC LIGHT-EMITTING DIODE AND LONG LIFESPAN ORGANIC LIGHT-EMITTING DIODE COMPRISING SAME

(71) Applicant: SFC CO., LTD., Cheongju-si (KR)

(72) Inventors: Soon-Wook Cha, Cheongju-si (KR); Yoona Shin, Cheongju-si (KR); Jung-Ho Yoo, Cheongju-si (KR); Sung Woo Kim, Cheongju-si (KR); Jiwon Lee, Cheongju-si (KR); Seok-Bae Park, Cheongju-si (KR); Hee-Dae Kim, Cheongju-si (KR); Yu-Rim Lee, Cheongju-si (KR); Dong Myung Park, Cheongju-si (KR); Seongeun Woo, Cheongju-si (KR)

(73) Assignee: SFC CO., LTD., Cheongju-si (KR)

( * ) Notice: Subject to any disclaimer, the term of this patent is extended or adjusted under 35 U.S.C. 154(b) by 674 days.

(21) Appl. No.: 17/420,379

(22) PCT Filed: Jan. 14, 2020

(86) PCT No.: PCT/KR2020/000690
§ 371 (c)(1),
(2) Date: Jul. 1, 2021

(87) PCT Pub. No.: WO2020/153650
PCT Pub. Date: Jul. 30, 2020

(65) Prior Publication Data
US 2022/0123219 A1    Apr. 21, 2022

(30) Foreign Application Priority Data

Jan. 21, 2019  (KR) .................. 10-2019-0007428
Jun. 18, 2019  (KR) .................. 10-2019-0071986

(51) Int. Cl.
| | | |
|---|---|---|
| C07D 307/91 | (2006.01) | |
| H10K 85/60 | (2023.01) | |
| H10K 50/12 | (2023.01) | |
| H10K 50/15 | (2023.01) | |
| H10K 50/16 | (2023.01) | |
| H10K 50/17 | (2023.01) | |

(52) U.S. Cl.
CPC ....... *H10K 85/626* (2023.02); *H10K 85/6574* (2023.02); *H10K 50/12* (2023.02); *H10K 50/15* (2023.02); *H10K 50/16* (2023.02); *H10K 50/171* (2023.02)

(58) Field of Classification Search
None
See application file for complete search history.

(56) References Cited

U.S. PATENT DOCUMENTS

| | | | |
|---|---|---|---|
| 2018/0009776 A1 | 1/2018 | Cha et al. | |
| 2018/0123055 A1 | 5/2018 | Park et al. | |
| 2021/0053998 A1* | 2/2021 | Kim | ........... H10K 85/6572 |
| 2022/0416170 A1* | 12/2022 | Tasaki | ........... H10K 85/60 |

FOREIGN PATENT DOCUMENTS

| | | |
|---|---|---|
| KR | 101068224 B1 | 9/2011 |
| KR | 101111406 B1 | 4/2012 |
| KR | 20180077887 A | 7/2018 |
| KR | 20180131963 A | 12/2018 |
| WO | WO2016171429 A2 | 10/2016 |
| WO | WO2018066830 A1 | 4/2018 |
| WO | WO2018066831 A1 | 4/2018 |
| WO | WO2018174293 A1 | 9/2018 |

OTHER PUBLICATIONS

Machine translation of KR-2018007787-A, translation generated Mar. 2024, 48 pages. (Year: 2024).*
International Search Report of PCT/KR2019/000690, May 1, 2020, English translation.
Office Action from Korean Intellectual Property Office of 10-2019-0071986, Jul. 18, 2019.
The extended European search report of EP 20 74 5758, Jul. 20, 2022.
Ping Wang et al, Synthesis of all-deuterated tris(2-phenylpyridine) iridium for highly stable electrophosphorescence; the "deuterium effect", Journal of Materials Chemistry C, Jul. 2, 2013, vol. 1, pp. 4821-4825, RSC Publishing, Cambridge, United Kingdom.
Hayato Tsuji et al, The hydrogen/deuterium isotope effect of the host material on the lifetime of organic light-emitting diodes, ChemComm, Sep. 15, 2014, vol. 50, pp. 14870-14872, Royal Society of Chemistry, Cambridge, United Kingdom.

* cited by examiner

*Primary Examiner* — Robert S Loewe
(74) *Attorney, Agent, or Firm* — STIP Law Group, LLC

(57) ABSTRACT

Disclosed herein are an anthracene derivative represented by [Chemical Formula A] and an organic light-emitting diode comprising same. In [Chemical Formula A], the substituents $R_1$ to $R_5$, R, $R_{11}$ to $R_{18}$, $L_1$, and n are as defined in the description.

16 Claims, 1 Drawing Sheet

| 80 |
|---|
| 70 |
| 60 |
| 50 |
| 40 |
| 30 |
| 20 |
| 10 |

COMPOUND FOR ORGANIC LIGHT-EMITTING DIODE AND LONG LIFESPAN ORGANIC LIGHT-EMITTING DIODE COMPRISING SAME

CROSS-REFERENCE TO RELATED APPLICATIONS

This application is the U.S. National Phase under 35 U.S.C. § 371 of International Application No. PCT/KR2020/000690 filed on Jan. 14, 2020, which in turn claims the benefit of Korean Applications No. 10-2019-0007428 filed on Jan. 21, 2019, and No. 10-2019-0071986 filed on Jun. 18, 2019, the disclosures of which are incorporated by reference into the present application.

TECHNICAL FIELD

The present disclosure relates to a compound for an organic light-emitting diode and an organic light-emitting diode, characterized by longevity, comprising same.

BACKGROUND ART

Organic light-emitting diodes (OLEDs), which are self-emitting devices, enjoy advantages including a wide viewing angle, high contrast, fast response time, high luminance, a low driving voltage, a high response speed, and polychromatic properties.

A typical organic light emitting diode includes an anode and a cathode, which face each other, with an organic emission layer for light emission disposed therebetween.

In detail, the organic light-emitting diode may have a structure in which a hole transport layer, a light-emitting layer, an electron transport layer, and a cathode are sequentially formed on an anode. Here, the hole transport layer, the light-emitting layer, and the electron transport layer are each an organic thin film composed of an organic compound.

Having such a structure, the organic light-emitting diode operates according to the following principle. When a voltage is applied between the anode and the cathode, a hole injected from the anode moves toward the light-emitting layer through the hole transport layer while an electron injected from the cathode moves toward the light-emitting layer through the electron transport layer. In the light-emitting layer zone, the carriers such as a hole and an electron recombine to produce an exciton. The exciton returns to the ground state from the excited state, emitting light.

Materials used as organic layers in organic light-emitting diodes may be divided according to functions into luminescent materials and charge transport materials, for example, a hole injection material, a hole transport material, an electron transport material, and an electron injection material. The light-emitting mechanism forms the basis of classification of luminescent materials as fluorescent and phosphorescent materials, which use excitons in singlet and triplet states, respectively.

When a single material is employed as the luminescent material, intermolecular actions cause the maximum luminescence wavelength to shift toward a longer wavelength, resulting in a reduction in color purity and luminous efficiency due to light attenuation. In this regard, a host-dopant system may be used as a luminescent material so as to increase the color purity and the luminous efficiency through energy transfer.

This is based on the principle whereby, when a dopant which is smaller in energy band gap than a host forming a light-emitting layer is added in a small amount to the light-emitting layer, excitons are generated from the light-emitting layer and transported to the dopant, emitting light at high efficiency. Here, light with desired wavelengths can be obtained depending on the kind of the dopant because the wavelength of the host moves to the wavelength range of the dopant.

Meanwhile, studies have been made to introduce a deuterium-substituted compound as a material in the light emitting layer in order to improve the longevity and stability of the organic light emitting diode.

Compounds substituted with deuterium are known to exhibit differences in thermodynamic behavior from those bonded with hydrogen because the atomic mass of deuterium is twice as great as that of hydrogen, which results in lower zero point energy and lower vibration energy level.

In addition, physicochemical properties involving deuterium, such as chemical bond lengths, etc., appear to be different from those involving hydrogen for hydrogen. In particular, the van der Waals radius of deuterium is smaller than that of hydrogen because of the smaller stretching amplitude of the C-D bond compared to the C—H bond. Generally, the C-D bond is shorter and stronger than the C—H bond. Upon deuterium substitution, the ground state energy is lowered and a short bond length is formed between the carbon atom and the deuterium atom. Accordingly, the molecular hardcore volume becomes smaller, thereby reducing the electron polarizability can be reduced, and the thin film volume can be increased by weakening the intermolecular interaction.

As discussed above, deuterium substitution provides the effect of reducing the crystallinity of the thin film, that is, it makes the thin film amorphous. Generally, a compound having deuterium substitution may be advantageously used to increase the lifespan and driving characteristics of an OLED and further improve the thermal resistance.

With respect to related arts for organic light emitting compounds containing deuterium, reference may be made to Korean Patent Number 10-1111406, which discloses a low-voltage driving and long lifespan diode employing a deuterium-substituted, carbazole-containing compound or a mixture of deuterium-substituted compounds and to Korean Patent Number 10-1068224, which discloses the use of an anthracene derivative bearing a deuterium-substituted phenyl group as a host.

In spite of various efforts, including the techniques of the cited documents, made to fabricate organic light emitting diodes exhibiting longevity characteristics, there is a still continuing need for development of an organic light-emitting diode that has improved long lifespan characteristics.

DISCLOSURE

Technical Problem

In order to solve problems encountered in the conventional techniques, an aspect of the present disclosure is to provide an anthracene derivative as a host in a light emitting layer of an organic light emitting diode, the anthracene derivative being based on a special structure and having deuterium introduced at a specific content or higher thereinto, whereby more enhanced long lifespan characteristics can be imparted to the organic light emitting diode.

Another aspect of the present disclosure is to provide an organic light emitting diode comprising the anthracene derivative as a host in a light emitting layer thereof.

Technical Solution

The present disclosure provides an anthracene derivative represented by the following Chemical Formula A:

[Chemical Formula A]

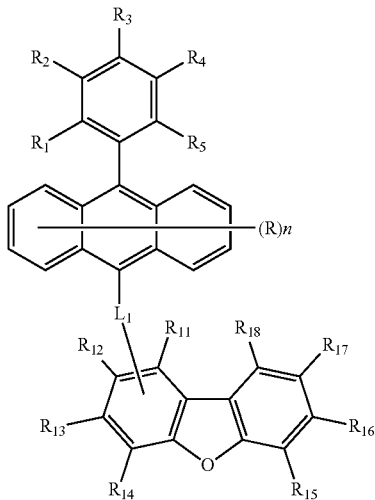

wherein, $R_1$ to $R_5$, which may be same or different, are each independently a hydrogen or deuterium atom, R is a deuterium atom, n is an integer of 0 to 8, with a hydrogen atom positioned on an aromatic carbon atom which is not substituted with R within the anthracene moiety, $L_1$, which functions as a linker, is a single bond or a deuterium-substituted or unsubstituted arylene of 6 to 12 carbon atoms;

$R_{11}$ to $R_{14}$, which may be same or different, are each independently a hydrogen or deuterium atom, with a proviso that one of $R_{11}$ to $R_{14}$ is a single bond to the linker $L_1$ through which the anthracenyl moiety is connected to one of the 6-membered aromatic rings in the dibenzofuran moiety, and $R_{15}$ to $R_{18}$, which may be same or different, are each independently selected from a hydrogen atom, a deuterium atom, a deuterium-substituted or unsubstituted phenyl, a deuterium-substituted or unsubstituted biphenyl, a deuterium-substituted or unsubstituted terphenyl, a deuterium-substituted or unsubstituted naphthyl, a deuterium-substituted or unsubstituted phenanthryl, and a fluorenyl in which identical or different alkyls of 1 to 5 carbon atoms may or may not be substituted on the carbon atom at position 9 and a deuterium atom may or may not be substituted on each of the carbon atoms of the aromatic rings, at least one of $R_{15}$ to $R_{18}$ being selected from a deuterium-substituted or unsubstituted phenyl, a deuterium-substituted or unsubstituted biphenyl, a deuterium-substituted or unsubstituted terphenyl, a deuterium-substituted or unsubstituted naphthyl, a deuterium-substituted or unsubstituted phenanthryl, and a fluorenyl in which identical or different alkyls of 1 to 5 carbon atoms may or may not be substituted on the carbon atom at position 9 and a deuterium atom may or may not be substituted on each of the carbon atoms of the aromatic rings, wherein the anthracene derivative has a degree of deuteration of 30% or more (percentages of all deuterium atoms bonded directly to carbon atoms of the anthracene derivative relative to a sum of all deuterium and hydrogen atoms bonded directly to carbon atoms of the anthracene derivative).

In addition, the present disclosure provides an organic light-emitting diode comprising the anthracene derivative represented by Chemical Formula A.

Advantageous Effects

When used as hosts in a light-emitting layer, the anthracene derivatives according to the present disclosure exhibit longer lifespan properties than preexisting materials. Thus, the anthracene derivatives according to the present disclosure can impart improved properties to organic light-emitting diodes.

BRIEF DESCRIPTION OF THE DRAWINGS

The above and other aspects, features, and advantages of the present disclosure will be more apparent from the following detailed description taken in conjunction with the accompanying drawings, in which:

FIG. 1 is a schematic view of the structure of an organic light-emitting diode according to an embodiment of the present disclosure.

MODE FOR CARRYING OUT THE INVENTION

Hereinafter, exemplary embodiments which can be easily implemented by those skilled in the art will be described with reference to the accompanying drawing.

In each drawing of the present disclosure, sizes or scales of components may be enlarged or reduced from their actual sizes or scales for better illustration, and known components may not be depicted therein to clearly show features of the present disclosure. Therefore, the present disclosure is not limited to the drawings. When describing the principle of the embodiments of the present disclosure in detail, details of well-known functions and features may be omitted to avoid unnecessarily obscuring the presented embodiments.

In drawings, for convenience of description, sizes of components may be exaggerated for clarity. For example, since sizes and thicknesses of components in drawings are arbitrarily shown for convenience of description, the sizes and thicknesses are not limited thereto. Furthermore, throughout the description, the terms "on" and "over" are used to refer to the relative positioning, and mean not only that one component or layer is directly disposed on another component or layer but also that one component or layer is indirectly disposed on another component or layer with a further component or layer being interposed therebetween. Also, spatially relative terms, such as "below", "beneath", "lower", and "between" may be used herein for ease of description to refer to the relative positioning.

Throughout the specification, when a portion may "include" a certain constituent element, unless explicitly described to the contrary, it may not be construed to exclude another constituent element but may be construed to further include other constituent elements. Further, throughout the specification, the word "on" means positioning on or below the object portion, but does not essentially mean positioning on the lower side of the object portion based on a gravity direction.

The present disclosure provides an anthracene derivative useful in a light emitting layer of an organic light emitting diode, the anthracene derivative being based on a special structure and having deuterium introduced at a specific content or higher thereinto, whereby more enhanced long lifespan characteristics can be imparted to the organic light emitting diode.

In greater detail, the present disclosure provides an anthracene derivative represented by the following Chemical Formula A:

[Chemical Formula A]

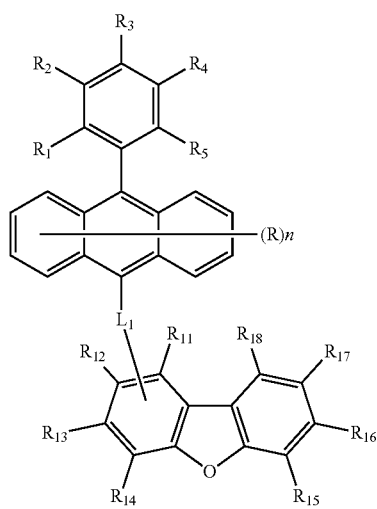

wherein,
$R_1$ to $R_5$, which may be same or different, are each independently a hydrogen or deuterium atom,
R is a deuterium atom,
n is an integer of 0 to 8, with a hydrogen atom positioned on an aromatic carbon atom which is not substituted with R within the anthracene moiety,
$L_1$, which functions as a linker, is a single bond or a deuterium-substituted or unsubstituted arylene of 6 to 12 carbon atoms;
$R_{11}$ to $R_{14}$, which may be same or different, are each independently a hydrogen or deuterium atom, with a proviso that one of $R_{11}$ to $R_{14}$ is a single bond to the linker $L_1$ through which the anthracenyl moiety is connected to one of the 6-membered aromatic rings in the dibenzofuran moiety, and
$R_{15}$ to $R_{18}$, which may be same or different, are each independently selected from a hydrogen atom, a deuterium atom, a deuterium-substituted or unsubstituted phenyl, a deuterium-substituted or unsubstituted biphenyl, a deuterium-substituted or unsubstituted terphenyl, a deuterium-substituted or unsubstituted naphthyl, a deuterium-substituted or unsubstituted phenanthryl, and a fluorenyl in which identical or different alkyls of 1 to 5 carbon atoms may or may not be substituted on the carbon atom at position 9 and a deuterium atom may or may not be substituted on each of the carbon atoms of the aromatic rings,
at least one of $R_{15}$ to $R_{18}$ being selected from a deuterium-substituted or unsubstituted phenyl, a deuterium-substituted or unsubstituted biphenyl, a deuterium-substituted or unsubstituted terphenyl, a deuterium-substituted or unsubstituted naphthyl, a deuterium-substituted or unsubstituted phenanthryl, and a fluorenyl in which identical or different alkyls of 1 to 5 carbon atoms may or may not be substituted on the carbon atom at position 9 and a deuterium atom may or may not be substituted on each of the carbon atoms of the aromatic rings,
wherein the anthracene derivative has a degree of deuteration of 30% or more (percentages of all deuterium atoms bonded directly to carbon atoms of the anthracene derivative relative to a sum of all deuterium and hydrogen atoms bonded directly to carbon atoms of the anthracene derivative).

The expression indicating the number of carbon atoms, such as "a substituted or unsubstituted alkyl of 1 to 30 carbon atoms", "a substituted or unsubstituted aryl of 5 to 50 carbon atoms", etc. means the total number of carbon atoms of, for example, the alkyl or aryl radical or moiety alone, exclusive of the number of carbon atoms of substituents attached thereto. For instance, a phenyl group with a butyl at the para position falls within the scope of an aryl of 6 carbon atoms, even though it is substituted with a butyl radical of 4 carbon atoms.

As used herein, the term "aryl" means an organic radical derived from an aromatic hydrocarbon by removing one hydrogen that is bonded to the aromatic hydrocarbon. It may be a single or fused aromatic system including a 5- to 7-membered ring, and preferably a 5- to 6-membered ring. Further, the aromatic system may include a fused ring that is formed by adjacent substituents on the aryl radical.

Examples of the aryl include phenyl, naphthyl, biphenyl, terphenyl, anthryl, indenyl, fluorenyl, phenanthryl, triperylenyl, pyrenyl, perylenyl, chrysenyl, naphthacenyl, and fluoranthenyl, but are not limited thereto.

At least one hydrogen atom of the aryl may be substituted by a deuterium atom, a halogen atom, a hydroxy, a nitro, a cyano, a silyl, an amino (—$NH_2$, —NH(R), —N(R') (R'') wherein R' and R'' are each independently an alkyl of 1 to 10 carbon atoms, in this case, called "alkylamino"), an amidino, a hydrazine, a hydrazone, a carboxyl, a sulfonic acid, a phosphoric acid, an alkyl of 1 to 24 carbon atoms, a halogenated alkyl of 1 to 24 carbon atoms, an alkenyl of 1 to 24 carbon atoms, an alkynyl of 1 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms, or a heteroarylalkyl of 2 to 24 carbon atoms.

The heteroaryl substituent used in the compound of the present disclosure refers to a hetero aromatic radical of 2 to 24 carbon atoms bearing 1 to 4 heteroatoms selected from among N, O, P, Se, Te, Si, Ge, and S. In the aromatic radical, two or more rings may be fused. One or more hydrogen atoms on the heteroaryl may be substituted by the same substituents as on the aryl.

Examples of the alkyl substituent useful in the present disclosure include methyl, ethyl, propyl, isopropyl, isobutyl, sec-butyl, tert-butyl, pentyl, iso-amyl, and hexyl. At least one hydrogen atom of the alkyl may be substituted by the same substituent as in the aryl.

Examples of the alkoxy substituent useful in the present disclosure include methoxy, ethoxy, propoxy, isobutyloxy, sec-butyloxy, pentyloxy, iso-amyloxy, and hexyloxy. At least one hydrogen atom of the alkoxy may be substituted by the same substituent as in the aryl.

Representative among examples of the silyl useful in the present disclosure are trimethylsilyl, triethylsilyl, triphenylsilyl, trimethoxysilyl, dimethoxyphenylsilyl, diphenylmethylsilyl, diphenylvinylsilyl, methylcyclobutylsilyl, and dimethylfurylsilyl. One or more hydrogen atoms of the silyl may be substituted by the same substituent as in the aryl.

In the anthracene derivative represented by Chemical Formula A according to the present disclosure, the anthracene ring moiety has a deuterium-substituted or unsubstituted phenyl as a substituent on the carbon atom at position 10 thereof and a deuterium-substituted or unsubstituted arylene of 6 to 12 carbon atoms as a linker $L_1$ on the carbon atom at position 9, the linker $L_1$ being bonded to a carbon atom of the dibenzofuran ring moiety (see the following Diagram 1), and at least one of the carbon atoms to which the linker is not bonded in the dibenzofuran ring moiety has a substituent selected from a hydrogen atom, a deuterium atom, a deuterium-substituted or unsubstituted phenyl, a deuterium-substituted or unsubstituted biphenyl, a deuterium-substituted or unsubstituted terphenyl, a deuterium-substituted or unsubstituted naphthyl, a deuterium-substituted or unsubstituted phenanthryl, and a fluorenyl in which identical or different alkyls of 1 to 5 carbon atoms may or may not be substituted on the carbon atom at position 9 and a deuterium atom may or may not be substituted on each of the carbon atoms of the aromatic rings, wherein the degree of deuteration of the anthracene derivative amounts to of 30% or more (percentages of all deuterium atoms bonded directly to carbon atoms of the anthracene derivative relative to a sum of all deuterium and hydrogen atoms bonded directly to carbon atoms of the anthracene derivative).

In Diagram 1, Z is a substituent selected from a deuterium-substituted or unsubstituted phenyl, a deuterium-substituted or unsubstituted biphenyl, a deuterium-substituted or unsubstituted terphenyl, a deuterium-substituted or unsubstituted naphthyl, a deuterium-substituted or unsubstituted phenanthryl, and a fluorenyl in which identical or different alkyls of 1 to 5 carbon atoms may or may not be substituted on the carbon atom at position 9 and a deuterium atom may or may not be substituted on each of the carbon atoms of the aromatic rings, and n is an integer of 0 to 4.

In this regard, the degree of deuteration preferably amounts to 35% or higher, more preferably to 40% or higher, more preferably to 45% or higher, more preferably to 50% or higher, more preferably to 55% or higher, more preferably to 60% or higher, more preferably to 65% or higher, more preferably to 70% or higher, more preferably to 75% or higher, and more preferably to 80% or higher.

With respect to the degree of deuteration used herein, the term "deuterated derivative" of compound X means a compound that is structurally identical to compound X, but has at least one deuterium (D) atom in substitution with a hydrogen atom bonded to a carbon atom, a nitrogen atom, or an oxygen atom in compound X.

In this regard, the term "yy % deuterated" or "yy % deuteration" refers to yy % for the ratio of deuterium atoms to a sum of hydrogen and deuterium atoms bonded directly to carbon, nitrogen, or oxygen atoms within compound X.

Thus, when two of six hydrogen atoms in benzene, the resulting benzene compound C6H4D2 is 33% deuterated (2/(4+2)×100=33%).

Likewise, when the anthracene derivative of the present disclosure is deuterated, the degree of deuteration thereof is expressed as a percentage of deuterium atoms bonded directly to carbon atoms within the anthracene derivative relative to a sum of hydrogen and deuterium atoms bonded directly to carbon atoms within the anthracene derivative.

For example, the anthracene derivative represented by Compound 1, below, has a total of 10 deuterium atoms including five deuterium atoms bonded to the phenyl group linked to the anthracene moiety and five deuterium atoms bonded to the phenyl group linked to the dibenzofuran moiety and a total of 14 hydrogen atoms including eight hydrogen atoms bonded to the anthracene moiety and six hydrogen atoms bonded to the 6-membered aromatic rings of the dibenzofuran moiety, so that its degree of deuteration can be calculated as 100×10/(10+14)=41.7%.

[Diagram 1]

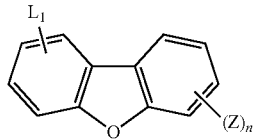

[Compound 1]

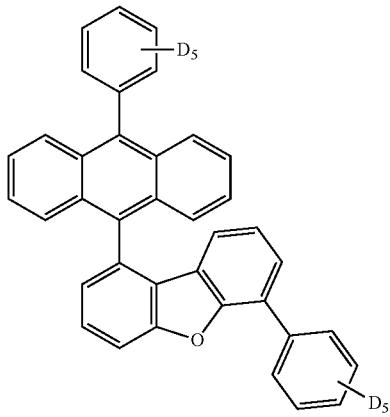

For a specific substituent, a degree of deuteration may differ from one compound molecule to another and thus is expressed as an average value.

An example is given by a partially deuterium-substituted anthracene radical. When a deuterium atom is intended to be substituted on all carbon atoms in an anthracene, the resulting anthracene derivative may be deuterated fully or partially according to reaction conditions. That is, there may be a mixture including fully deuterated anthracene molecules and partially deuterated anthracene molecules. It is very difficult to separate the fully deuterated anthracene molecules and the partially deuterate anthracene molecules from each other. In this case, the degree of deuteration can be calculated according to the entire structural formula with reference to an average degree of deuteration.

According to the present disclosure, the use of the anthracene derivative represented by Chemical Formula A as a material for a light-emitting layer in an organic light-emitting diode can further improve the lifespan of the organic light-emitting diode.

In an embodiment, the anthracene moiety in the anthracene derivative of the present disclosure may be fully hydrogenated, so that n may be 0.

In an embodiment, the anthracene moiety in the anthracene derivative of the present disclosure may be substituted with 4 to 8 deuterium atoms, so that n may be 4 to 8.

In an embodiment, the anthracene moiety in the anthracene derivative of the present disclosure may be substituted with 4 or 8 deuterium atoms so that n may be 4 or 8, respectively.

In an embodiment, the substituents $R_1$ to $R_5$ in the phenyl moiety of Chemical Formula A may each be a deuterium atom.

In an embodiment, the linker $L_1$ may be a single bond or a deuterium-substituted or unsubstituted phenylene.

In an embodiment, only one of the substituents $R_{15}$ to $R_{18}$ may be selected from a deuterium-substituted or unsubstituted phenyl, a deuterium-substituted or unsubstituted biphenyl, a deuterium-substituted or unsubstituted terphenyl, a deuterium-substituted or unsubstituted naphthyl, a deuterium-substituted or unsubstituted phenanthryl, and a fluorenyl in which identical or different alkyls of 1 to 5 carbon atoms may or may not be substituted on the carbon atom at position 9 and a deuterium atom may or may not be substituted on each of the carbon atoms of the aromatic rings.

Concrete examples of the anthracene derivative represented by Chemical Formula A include compounds represented by <Compound 1> to <Compound 66> below, but are not limited thereto:

<Compound 1>

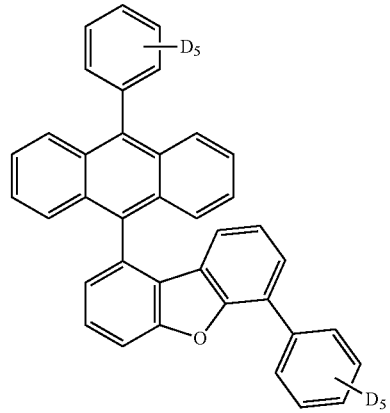

<Compound 2>

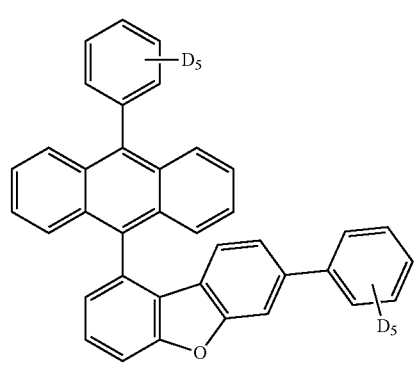

<Compound 3>
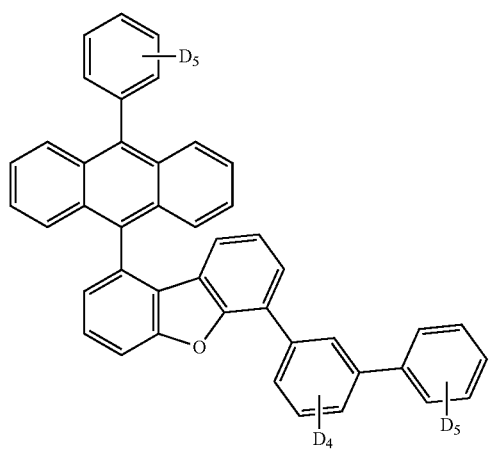
<Compound 4>
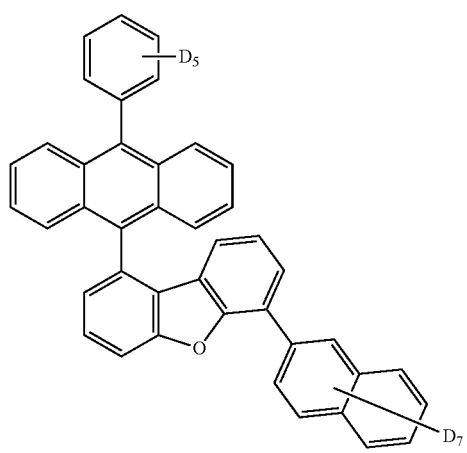
<Compound 5>
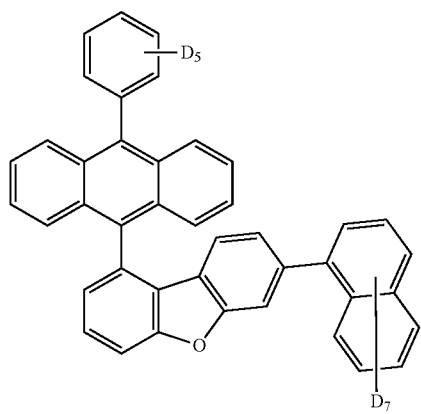
<Compound 6>
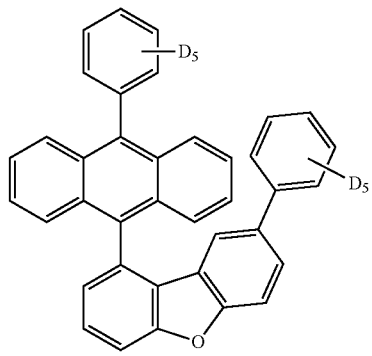
<Compound 7>
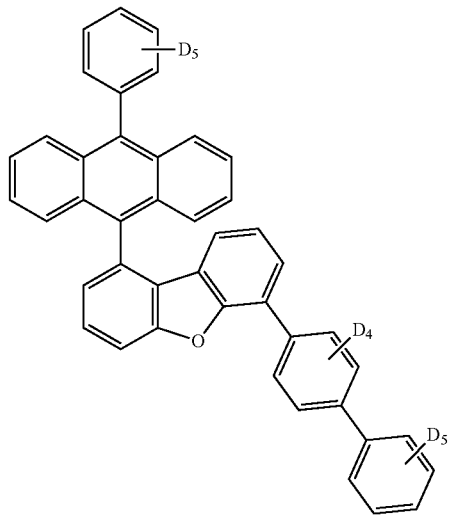
<Compound 8>
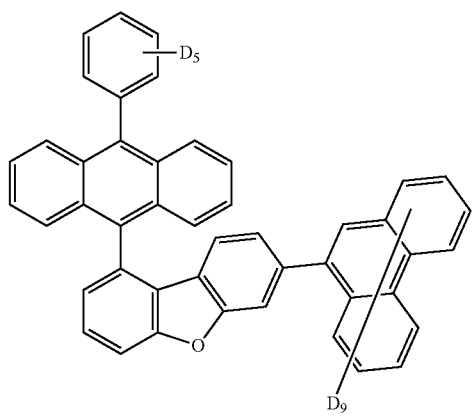

<Compound 9>
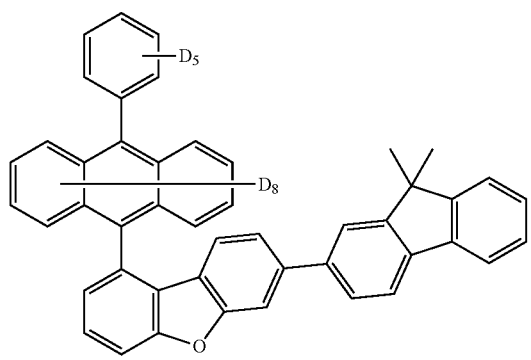
<Compound 10>
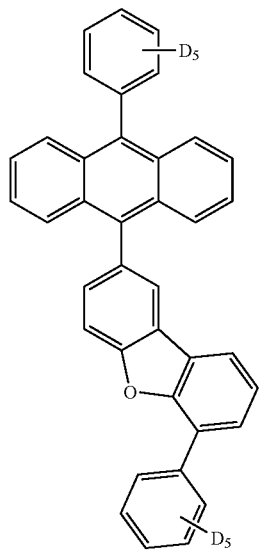
<Compound 11>
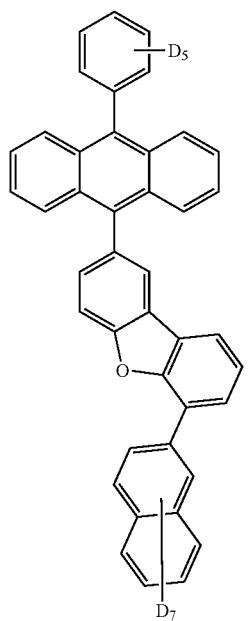
<Compound 12>
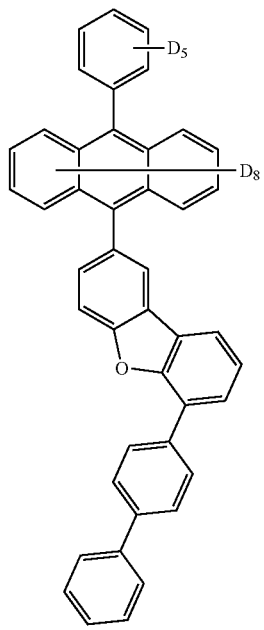
<Compound 13>
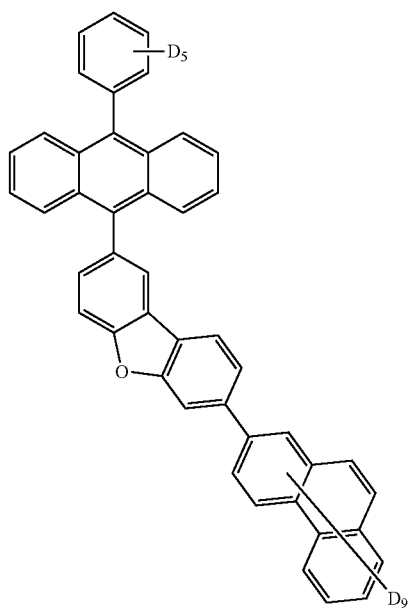

<Compound 14>
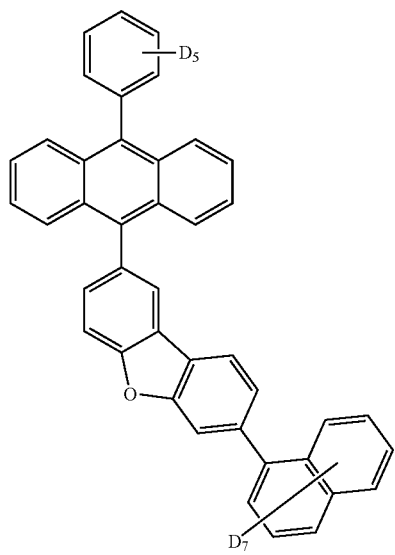
<Compound 15>
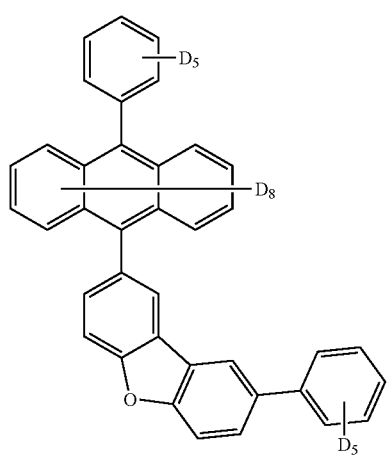
<Compound 16>
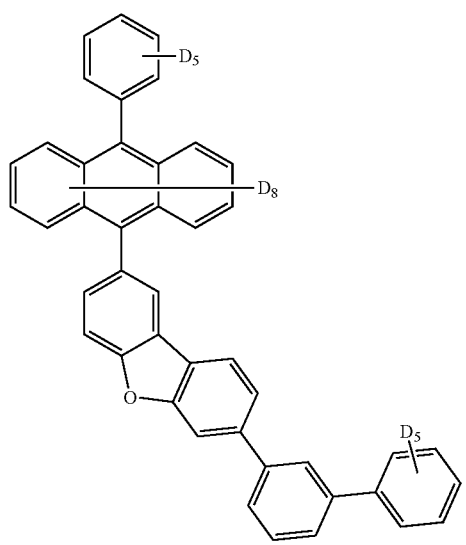
<Compound 17>
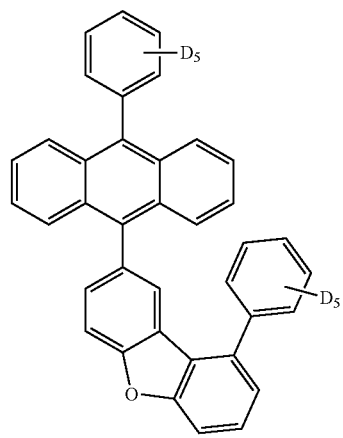
<Compound 18>
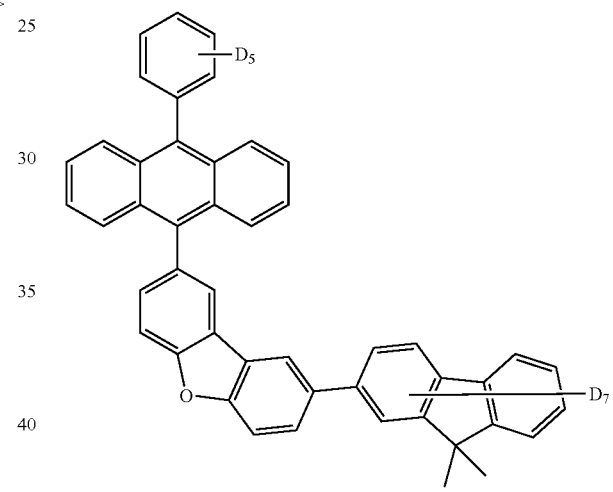
<Compound 19>
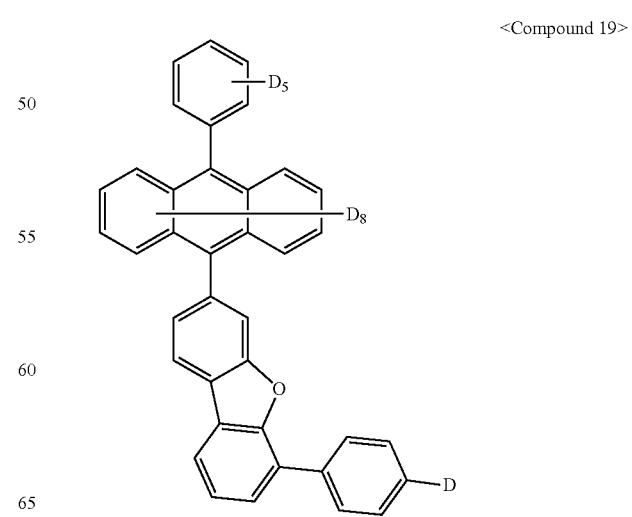

<Compound 20>
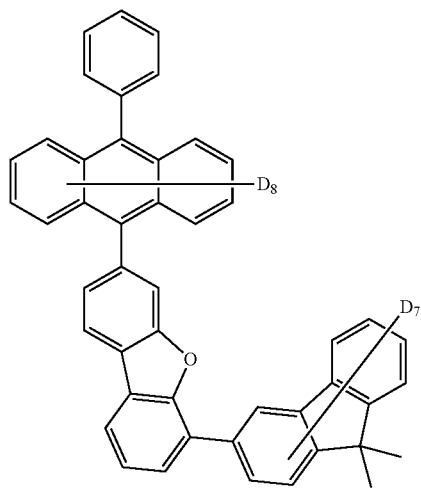
<Compound 22>
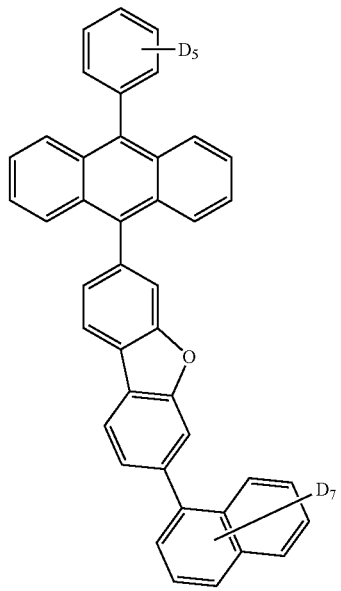
<Compound 21>
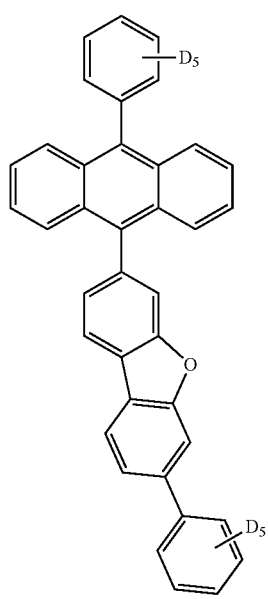
<Compound 23>
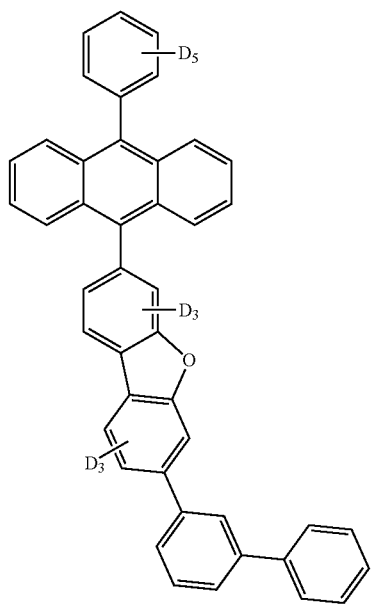

<Compound 24>
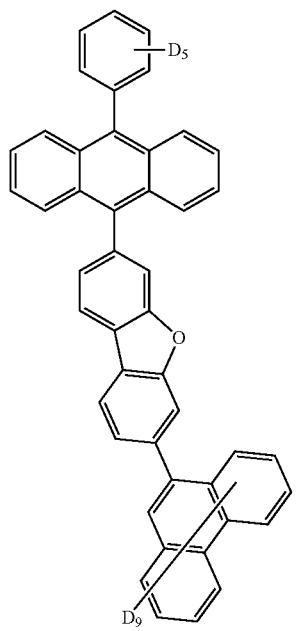
<Compound 25>
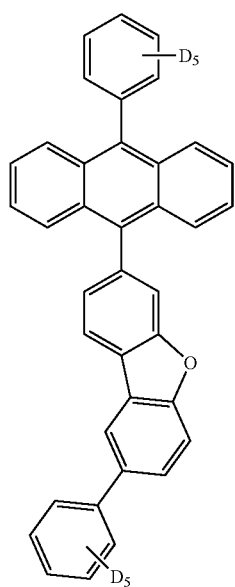
<Compound 26>
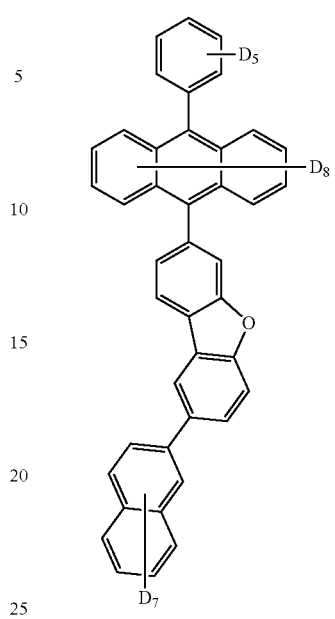
<Compound 27>
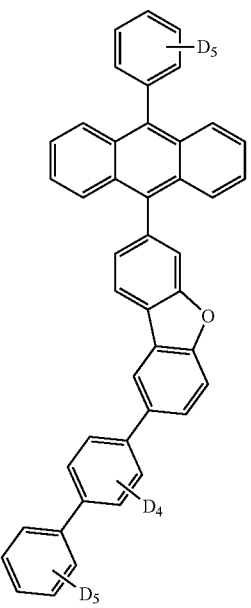

<Compound 28>
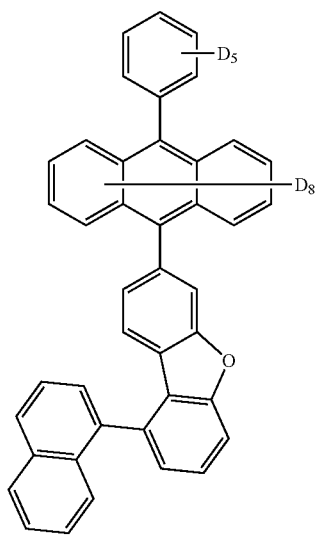
<Compound 29>
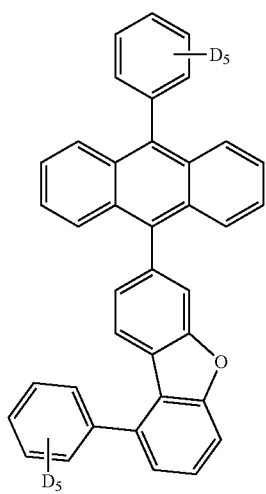
<Compound 30>
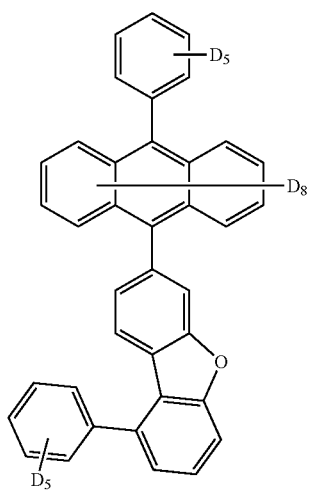
<Compound 31>
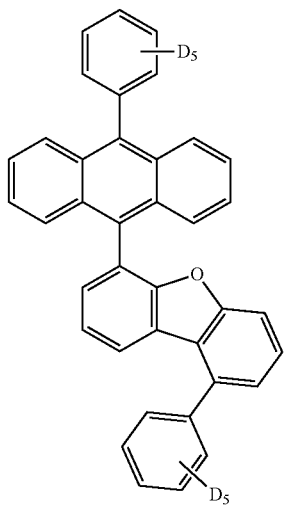
<Compound 32>
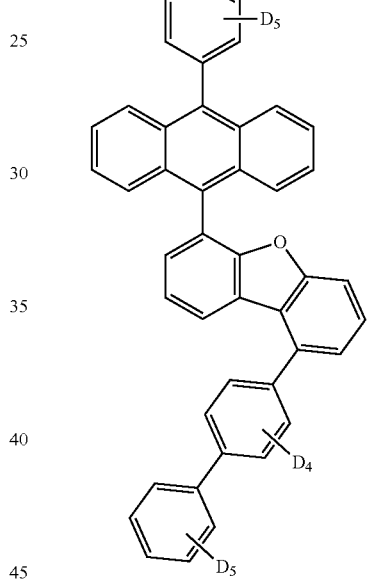
<Compound 33>
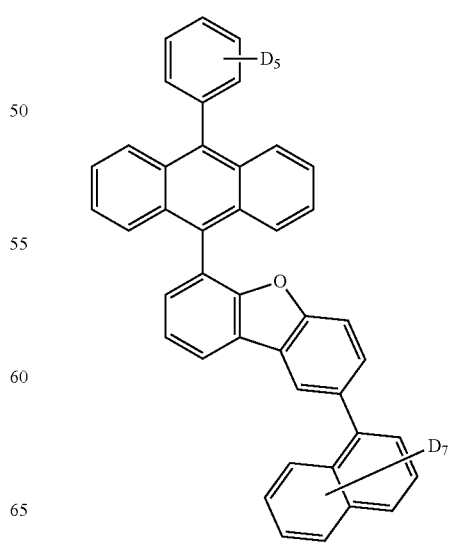

<Compound 34>
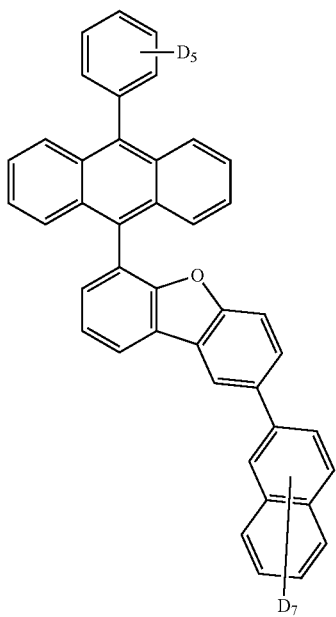
<Compound 35>
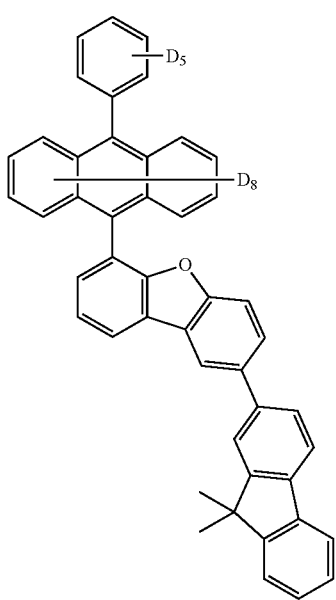
<Compound 36>
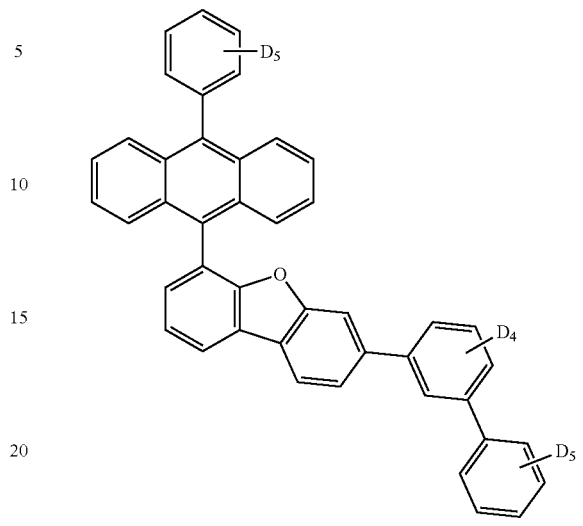
<Compound 37>
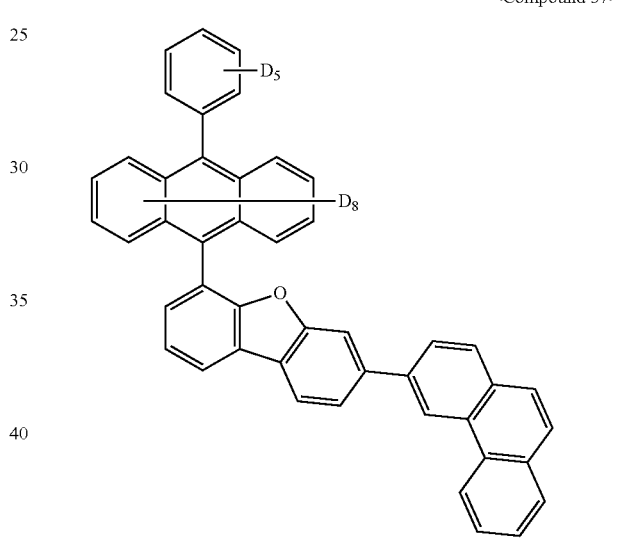
<Compound 38>
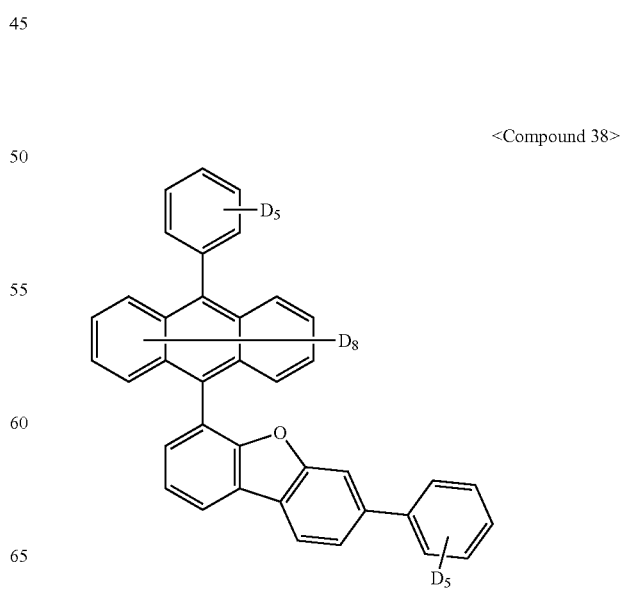

<Compound 39>
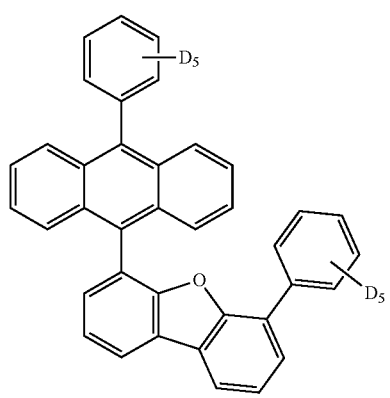
<Compound 40>
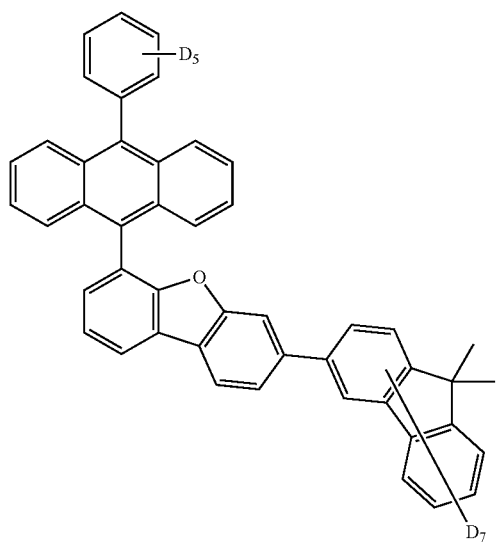
<Compound 41>
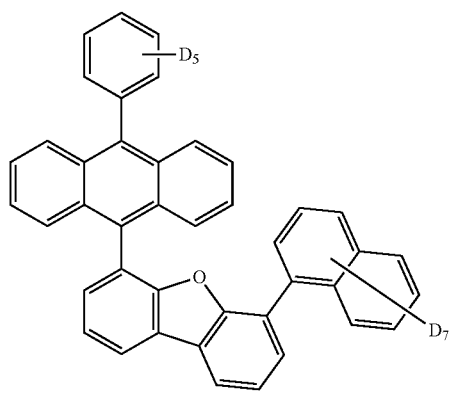
<Compound 42>
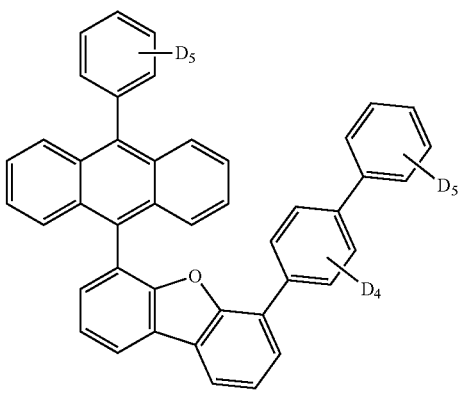
<Compound 43>
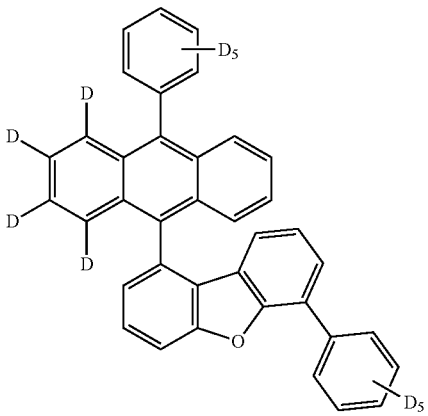
<Compound 44>
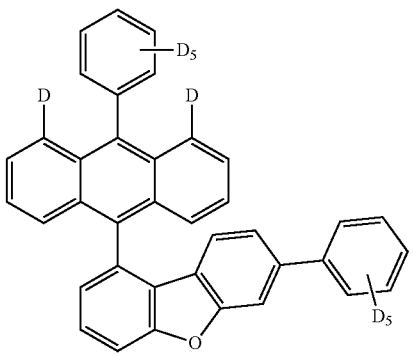

<Compound 45>
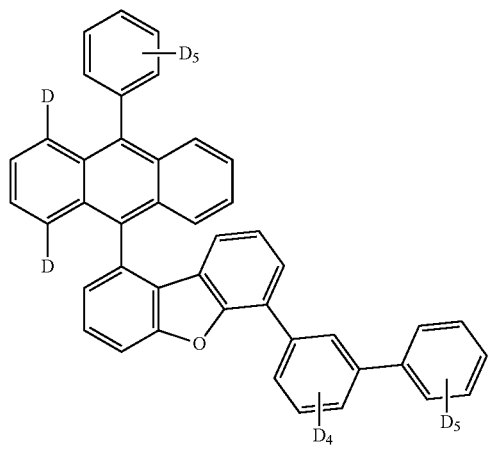
<Compound 46>
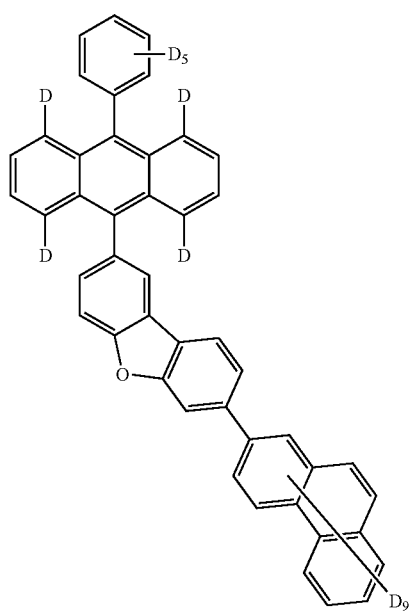
<Compound 47>
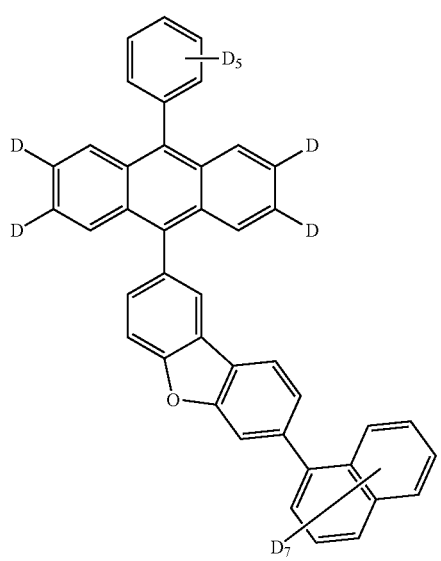
<Compound 48>
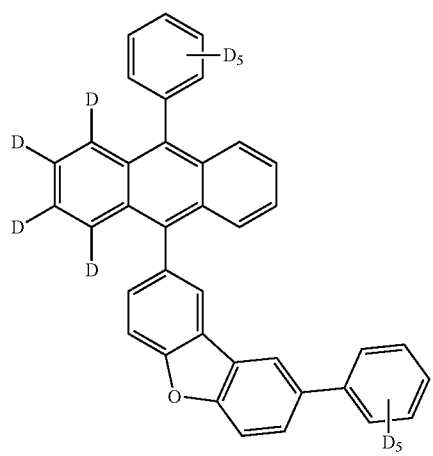
<Compound 49>
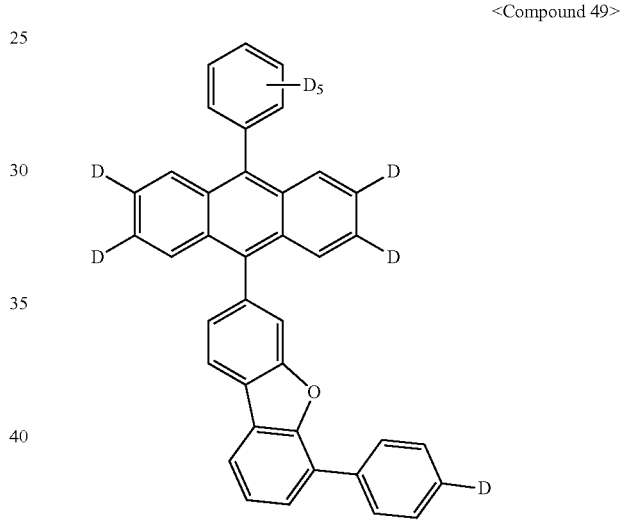
<Compound 50>
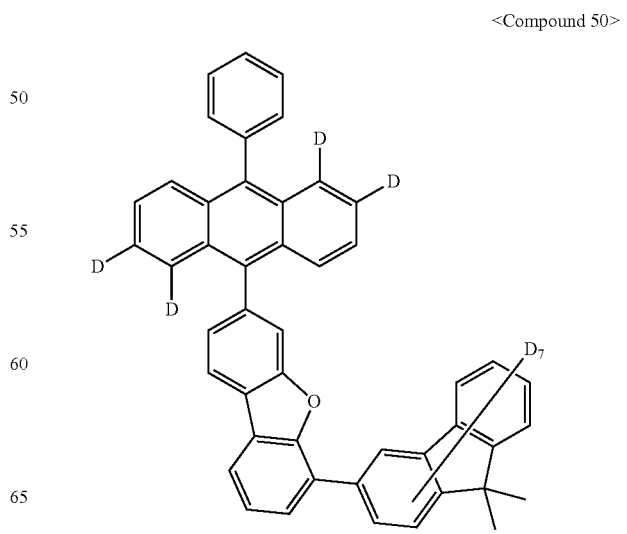

<Compound 51>
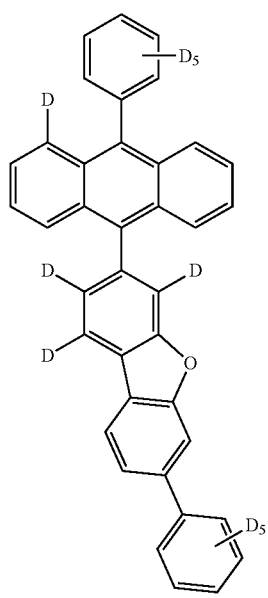
<Compound 52>
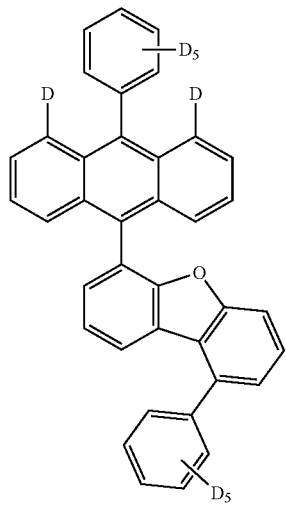
<Compound 53>
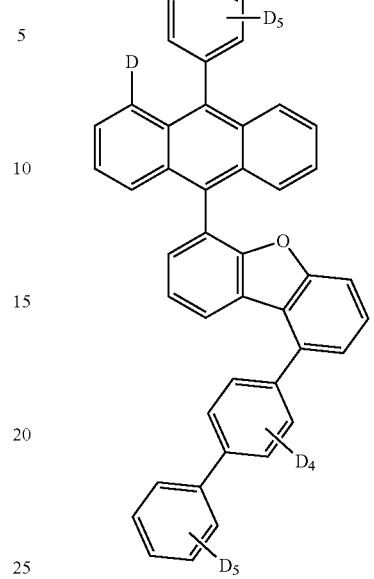
<Compound 54>
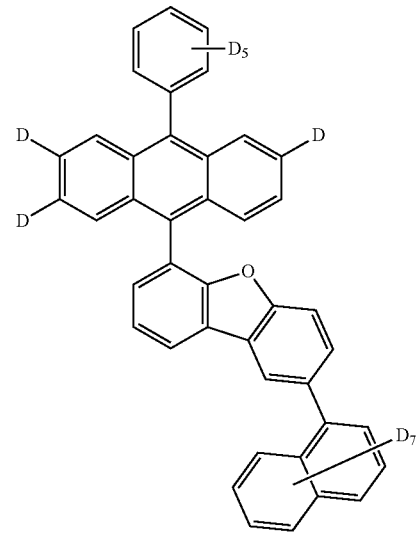

<Compound 55>
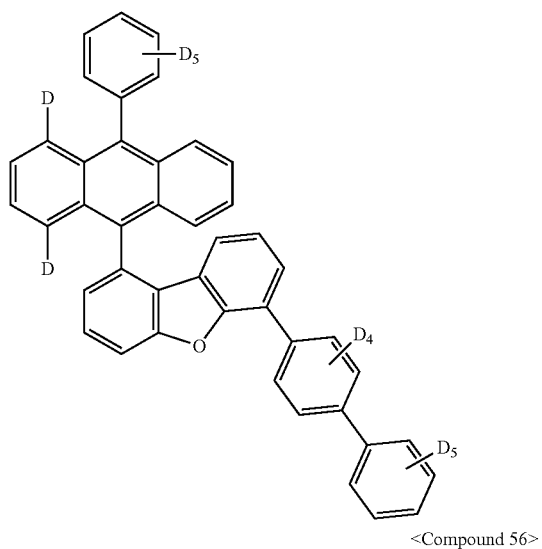
<Compound 56>
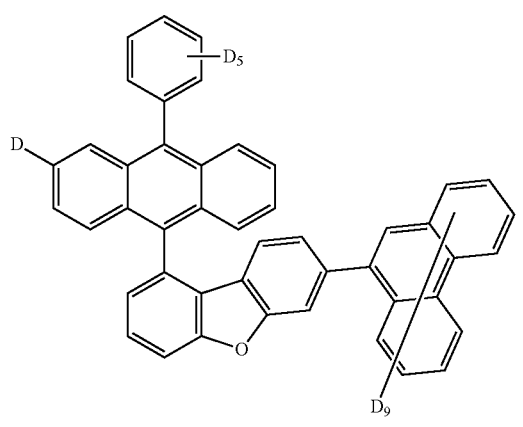
<Compound 57>
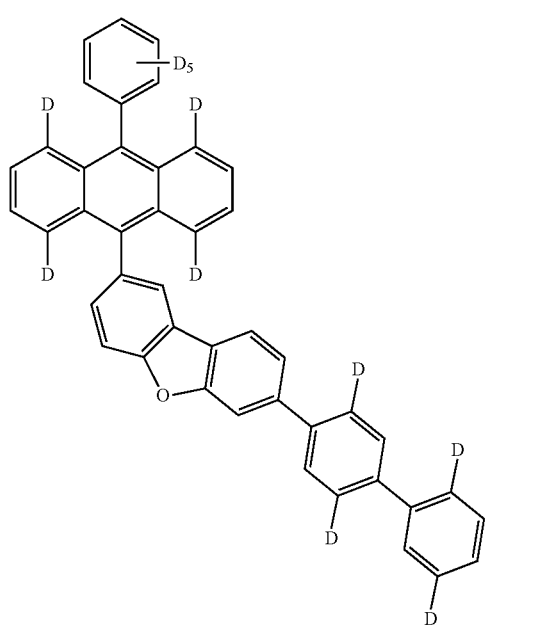
<Compound 58>
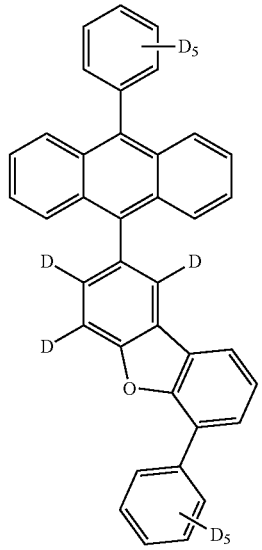
<Compound 59>
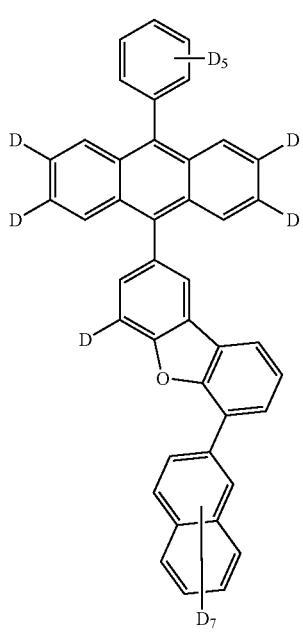
<Compound 60>
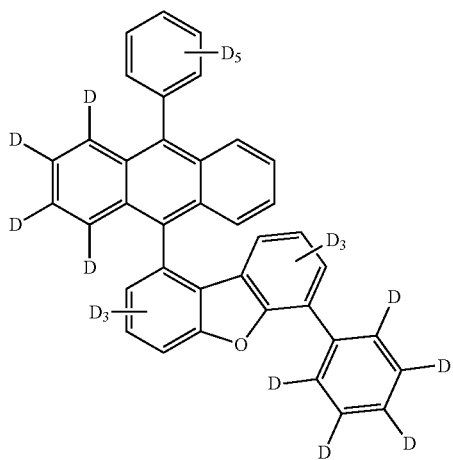

<Compound 61>
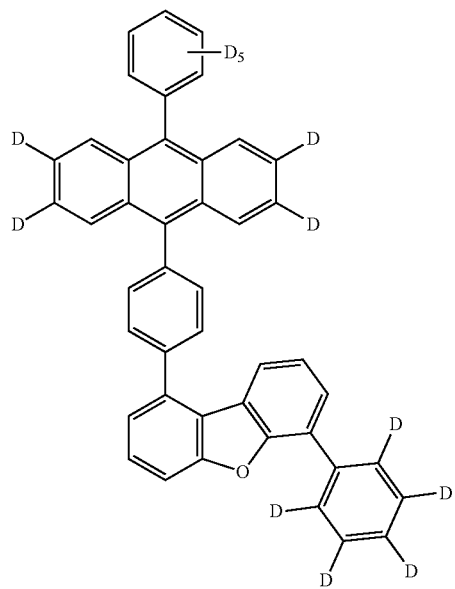
<Compound 62>
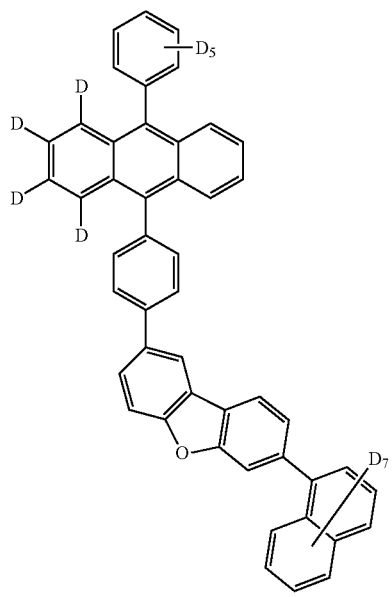
<Compound 63>
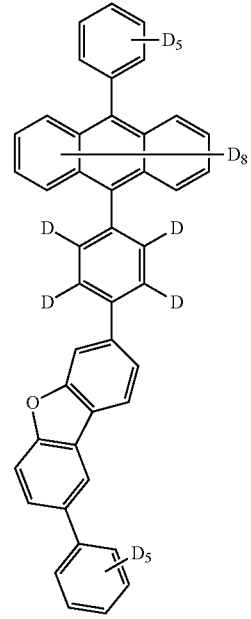
<Compound 64>
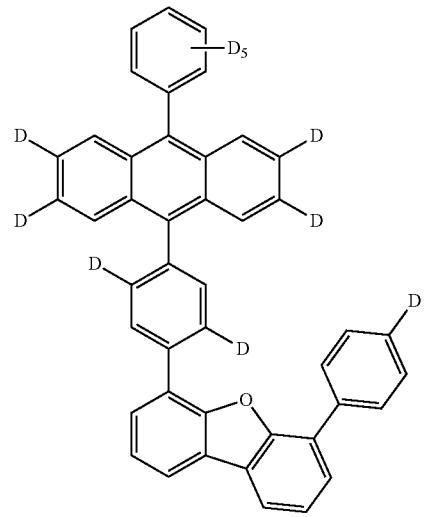

-continued

<Compound 65>

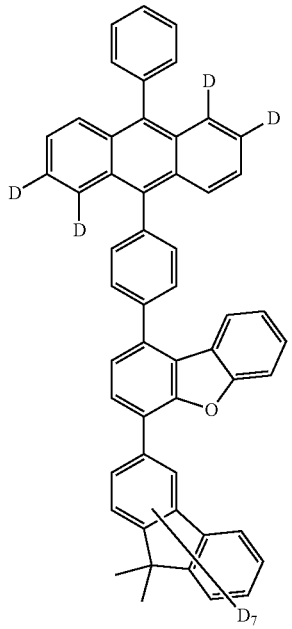

<Compound 66>

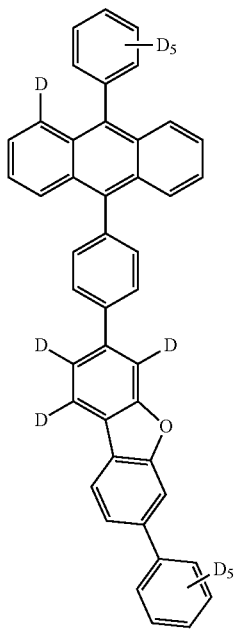

The present disclosure provides an organic light-emitting diode comprising the anthracene derivative represented by Chemical Formula A.

In detail, the organic light-emitting diode may comprise: a first electrode; a second electrode facing the first electrode; and an organic layer disposed between the first electrode and the second electrode, wherein the organic layer includes the anthracene derivative of the present disclosure.

In this regard, the organic layer within the organic light-emitting diode may at least one of a hole injection layer, a hole transport layer, a functional layer capable of both hole injection and hole transport, an electron transport layer, and an electron injection layer, in addition to the light-emitting layer.

Moreover, when the organic layer interposed between the first electrode and the second electrode is a light emitting layer, the light emitting layer may further contain a dopant wherein the anthracene derivative according to the present disclosure serves as a host.

FIG. 1 is a schematic view of the structure of an organic light-emitting diode according to the present disclosure.

As shown in FIG. 1, the organic light-emitting diode according to an embodiment of the present disclosure comprises an anode 20, a hole transport layer 40, an organic light-emitting layer 50, an electron transport layer 60, and a cathode 80, and optionally a hole injection layer 30 and an electron injection layer 70. In addition, one or two intermediate layers may be further formed in the organic light-emitting diode.

Here, the anthracene derivative represented by Chemical Formula A can be used as a host in the light emitting layer.

Reference is made to FIG. 1 with regard to the organic light-emitting diode of the present disclosure and the fabrication thereof. First, a substrate 10 is coated with an anode electrode material to form an anode 20. So long as it is used in a typical organic electroluminescence device, any substrate may be used as the substrate 10. Preferable is an organic substrate or transparent plastic substrate that exhibits excellent transparency, surface smoothness, ease of handling, and waterproofness. As the anode electrode material, indium tin oxide (ITO), indium zinc oxide (IZO), tin oxide ($SnO_2$), or zinc oxide (ZnO), which are transparent and superior in terms of conductivity, may be used.

A hole injection layer material is applied on the anode 20 by thermal deposition in a vacuum or by spin coating to form a hole injection layer 30. Subsequently, thermal deposition in a vacuum or by spin coating may also be conducted to form a hole transport layer with a hole transport layer material on the hole injection layer 30.

No particular limitations are imparted to the hole injection layer material, as long as it is one that is typically used in the art. For example, mention may be made of 2-TNATA [4,4',4''-tris(2-naphthylphenyl-phenylamino)-triphenylamine], NPD [N,N'-di(1-naphthyl)-N,N'-diphenylbenzidine)], TPD [N,N'-diphenyl-N,N'-bis(3-methylphenyl)-1,1'-biphenyl-4,4'-diamine], or DNTPD [N,N'-diphenyl-N,N'-bis-[4-(phenyl-m-tolyl-amino)-phenyl]-biphenyl-4,4'-diamine], but the present disclosure is not limited thereby.

So long as it is typically used in the art, any material may be selected for the hole transport layer without particular limitation. Examples include, but are not limited to, N,N'-bis(3-methylphenyl)-N,N'-diphenyl-[1,1-biphenyl]-4,4'-diamine (TPD), and N,N'-di(naphthalen-1-yl)-N,N'-diphenyl-benzidine (a-NPD).

Then, an organic light-emitting layer 50 containing a host and a dopant is deposited on the hole transport layer 40 by deposition in a vacuum or by spin coating. In some embodiments of the present disclosure, the light-emitting layer particularly ranges in thickness from 50 to 2,000 Å. Here, an electron density control layer (not shown) may be further formed on the organic light emitting layer 50, as necessary.

On the other hand, the light emitting layer may contain a dopant material as well as the host including the organic light emitting compound according to the present disclosure. In the case where the light-emitting layer contains a host and a dopant, the content of the dopant may range from about 0.01 to 20 parts by weight, based on 100 parts by weight of the host, but is not limited thereto.

In addition, the anthracene derivative represented by Chemical Formula A may be used as a host, alone, or in combination with a well-known host.

When used in combination with a well-known host, an available host may be at least one of the compounds represented by Chemical Formula B, below:

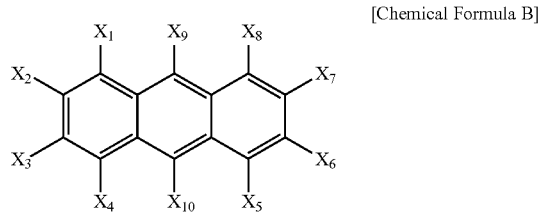

[Chemical Formula B]

wherein, $X_1$ to $X_{10}$, which may be the same or different, are each independently selected from the group consisting of a hydrogen atom, a deuterium atom, a substituted or unsubstituted alkyl of 1 to 30 carbon atoms, a substituted or unsubstituted alkenyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted aryl of 5 to 50 carbon atoms, a substituted or unsubstituted heteroaryl of 3 to 50 carbon atoms bearing O, N, or S as a heteroatom, a substituted or unsubstituted silicone, a substituted or unsubstituted boron, a substituted or unsubstituted silane, a carbonyl, a phosphoryl, an amino, a nitrile, a halogen, an amide, and an ester, wherein adjacent radicals may form an aliphatic, an aromatic, an aliphatic hetero, or an aromatic hetero fused ring.

More particularly, concrete examples of the host compound represented by Chemical Formula B include, but are not limited to, compounds of [Chemical Formula H-1] to [Chemical Formula H-196]:

[Chemical Formula H-1]

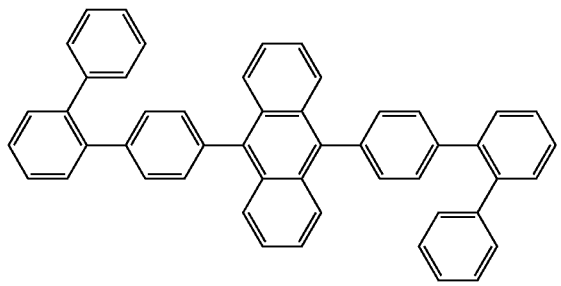

[Chemical Formula H-2]

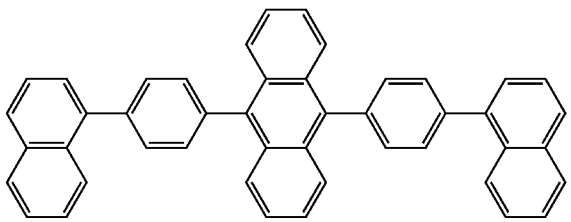

[Chemical Formula H-3]

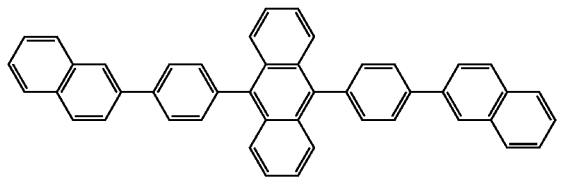

[Chemical Formula H-4]

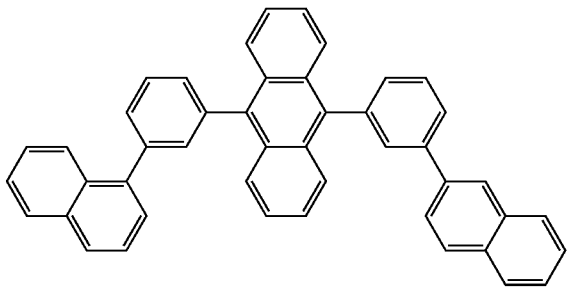

[Chemical Formula H-5]
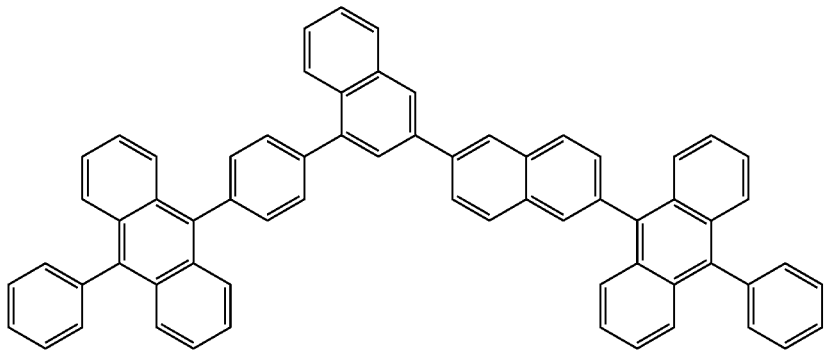
[Chemical Formula H-6]
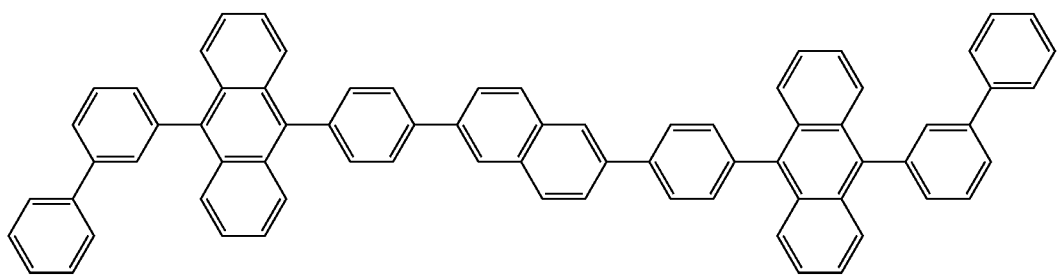
[Chemical Formula H-7]
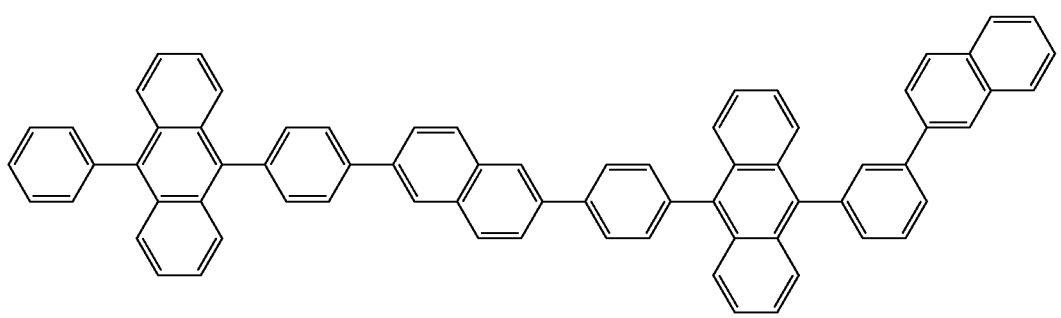
[Chemical Formula H-8]
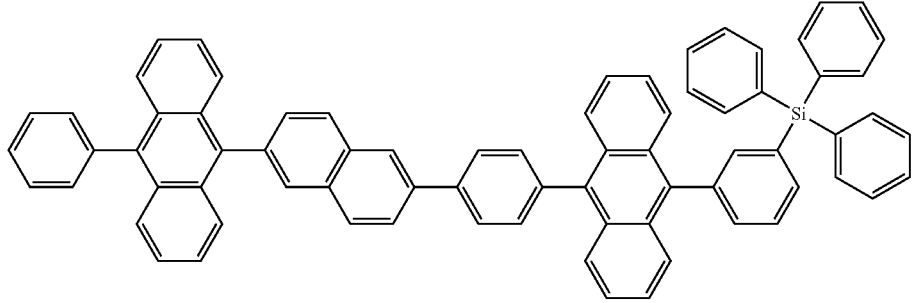
[Chemical Formula H-9]
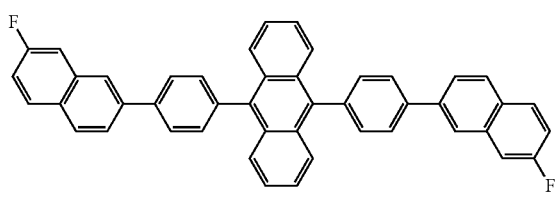
[Chemical Formula H-10]
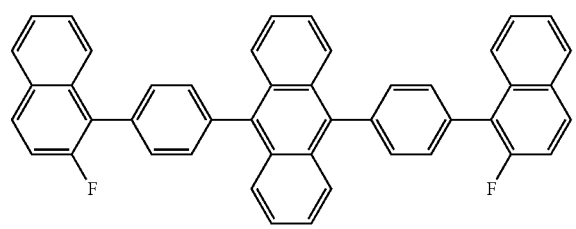

[Chemical Formula H-11]
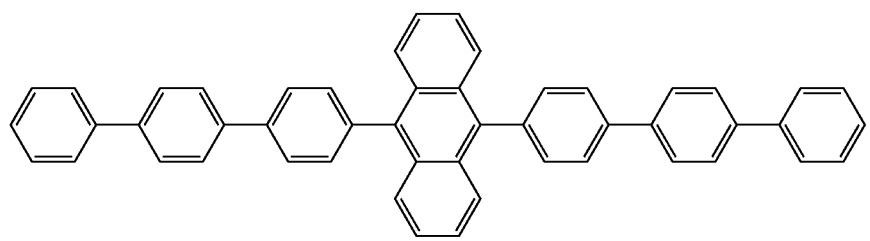
[Chemical Formula H-12]
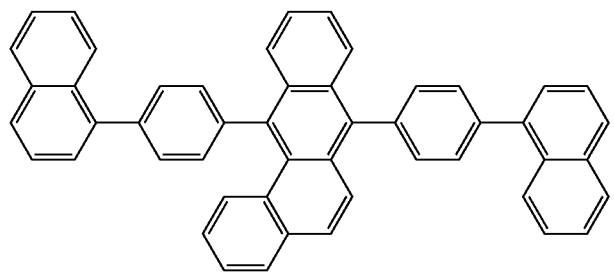
[Chemical Formula H-13]
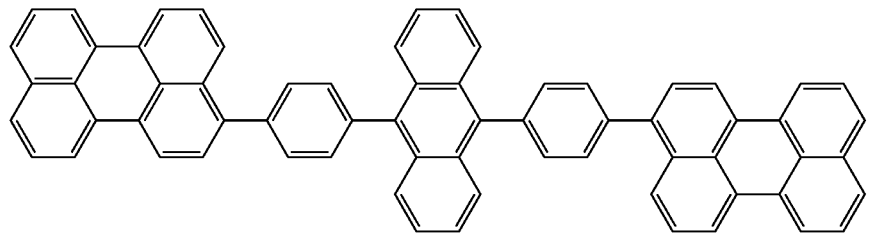
[Chemical Formula H-14]
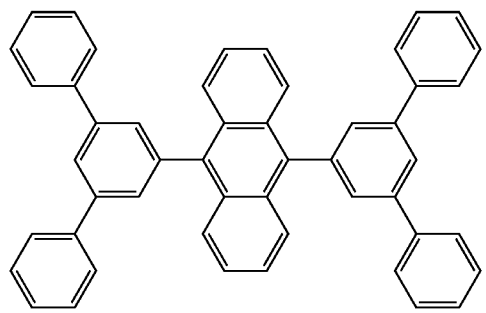
[Chemical Formula H-15]
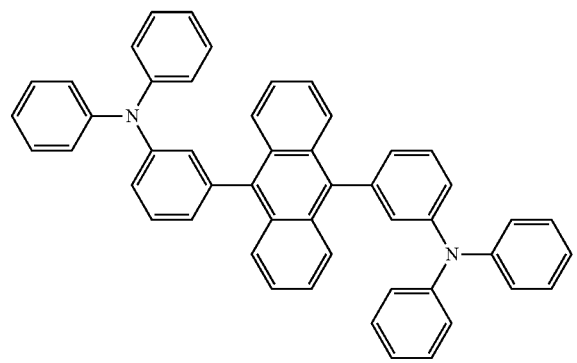
[Chemical Formula H-16]
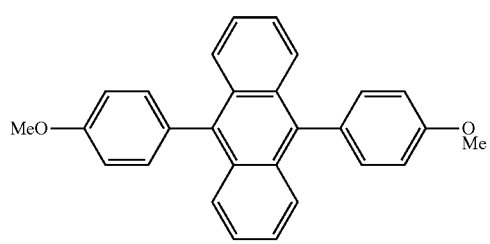

[Chemical Formula H-17]
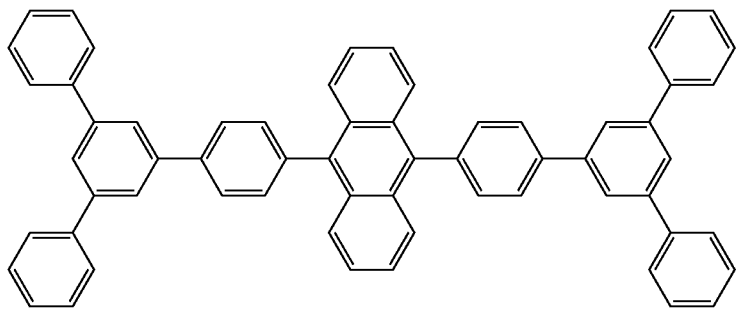
[Chemical Formula H-18]
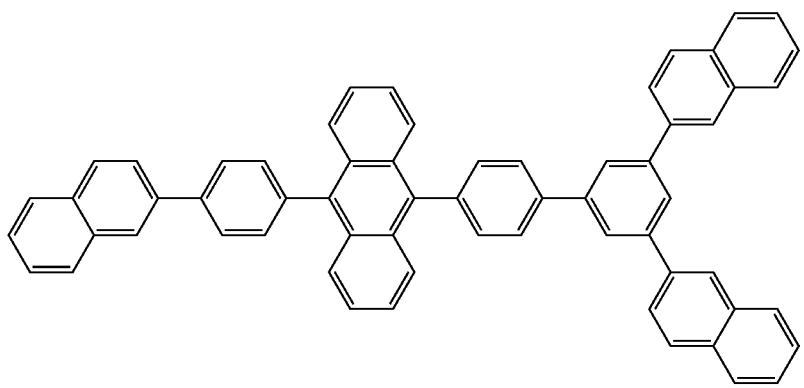
[Chemical Formula H-19]
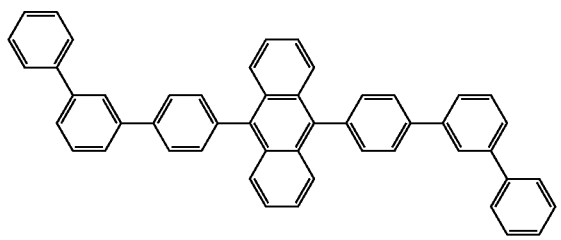
[Chemical Formula H-20]
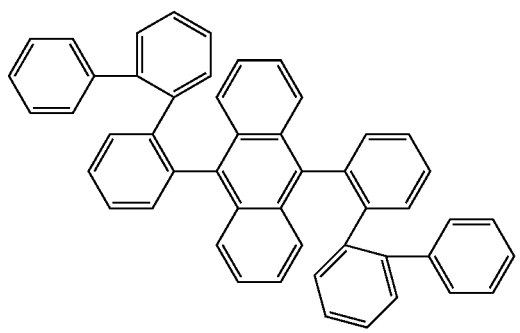
[Chemical Formula H-21]
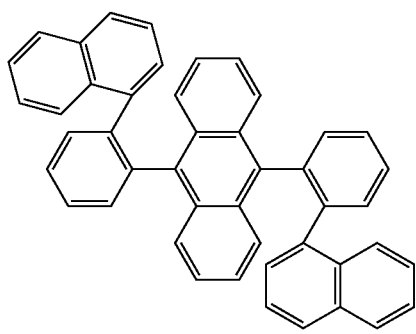
[Chemical Formula H-22]
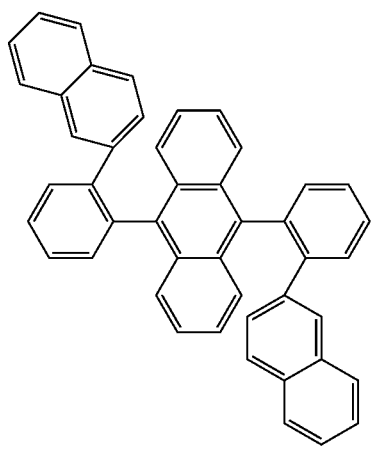

[Chemical Formula H-23]
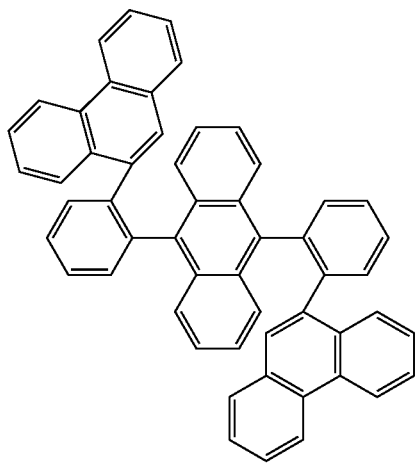
[Chemical Formula H-24]
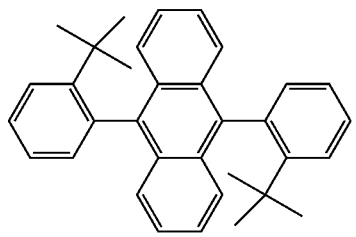
[Chemical Formula H-25]
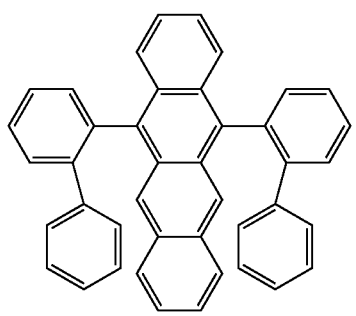
[Chemical Formula H-26]
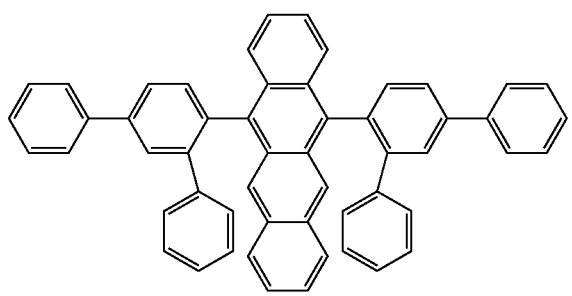
[Chemical Formula H-27]
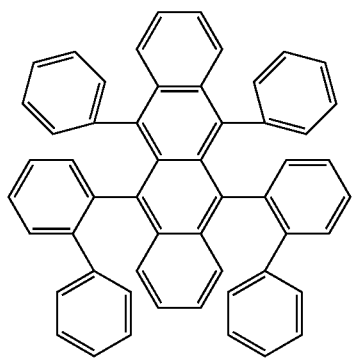
[Chemical Formula H-28]
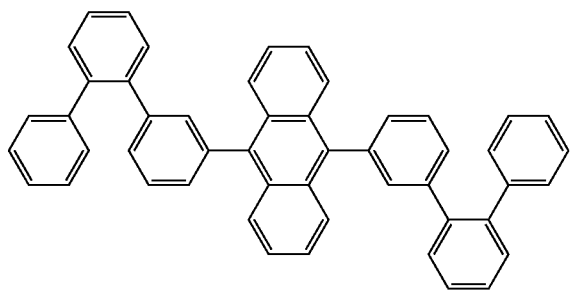
[Chemical Formula H-29]
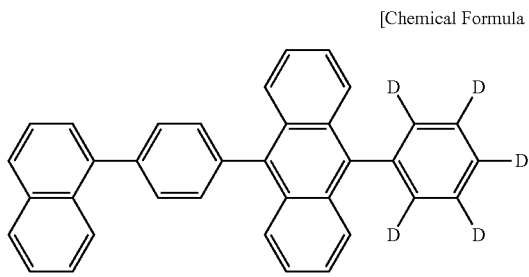
[Chemical Formula H-30]
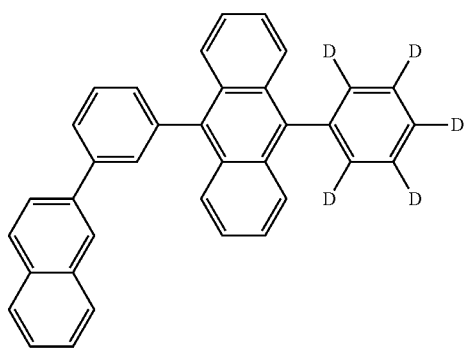

[Chemical Formula H-31]
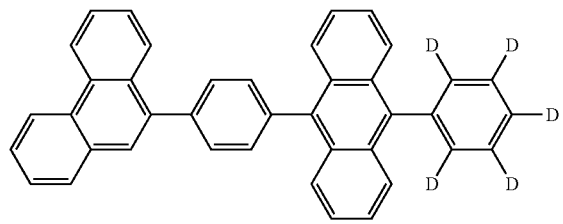
[Chemical Formula H-32]
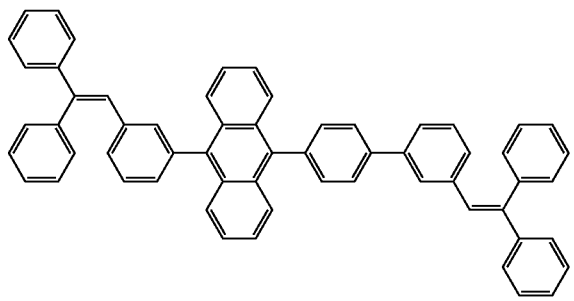
[Chemical Formula H-33]
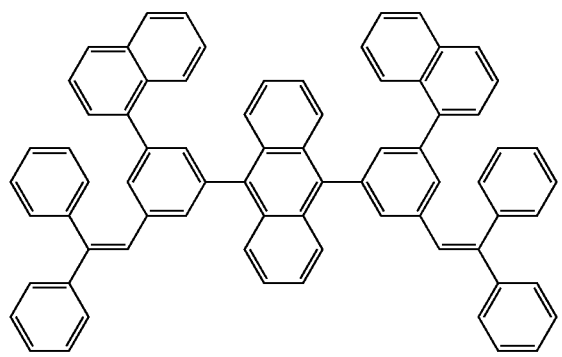
[Chemical Formula H-34]
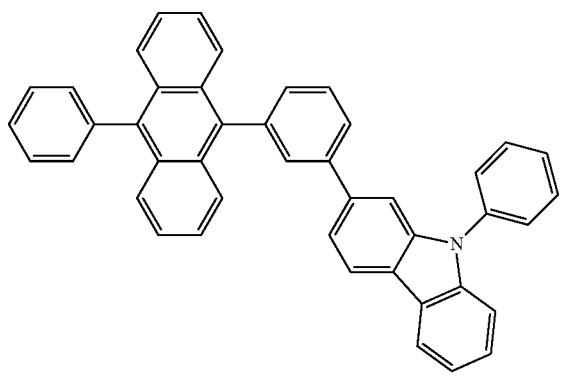
[Chemical Formula H-35]
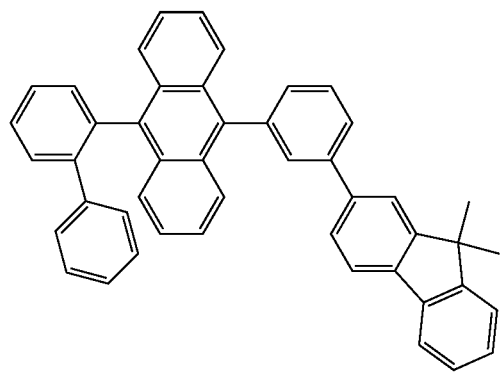
[Chemical Formula H-36]
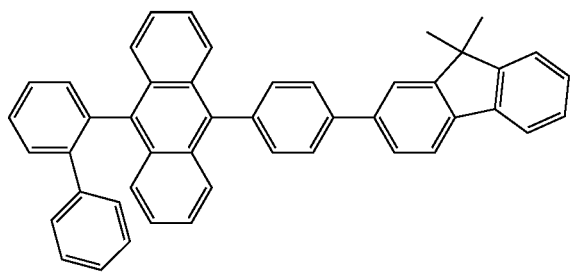
[Chemical Formula H-37]
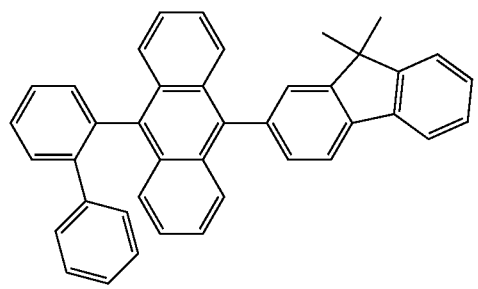
[Chemical Formula H-38]
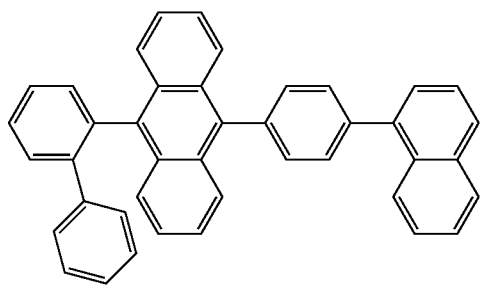

[Chemical Formula H-39]
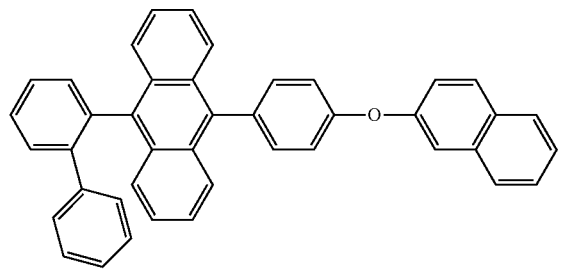
[Chemical Formula H-40]
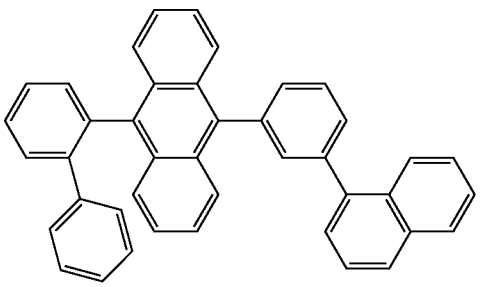
[Chemical Formula H-41]
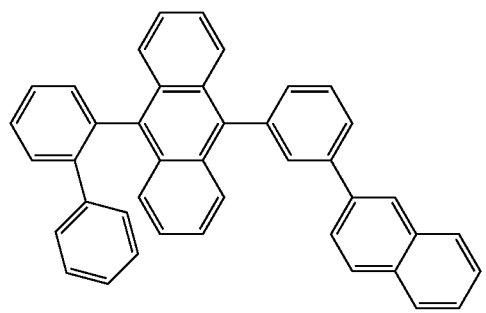
[Chemical Formula H-42]
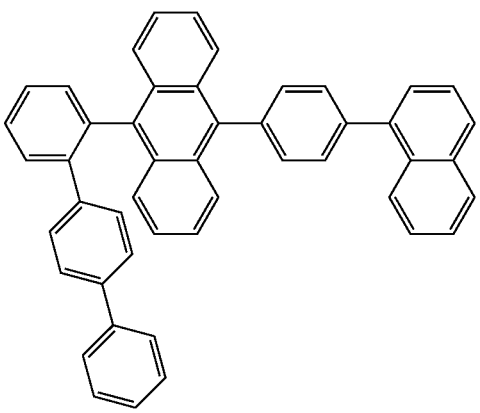
[Chemical Formula H-43]
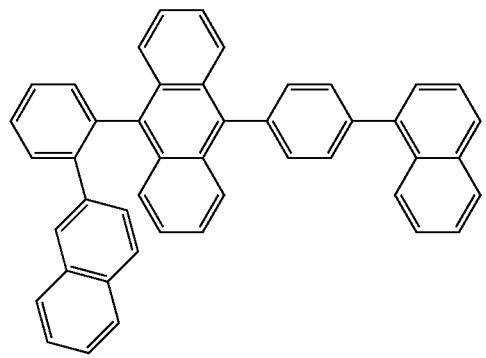
[Chemical Formula H-44]
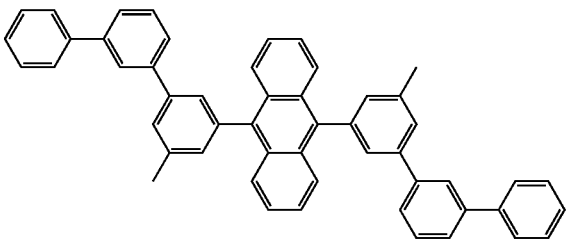
[Chemical Formula H-45]
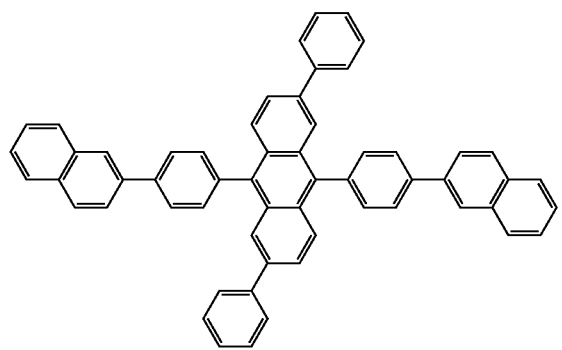
[Chemical Formula H-46]
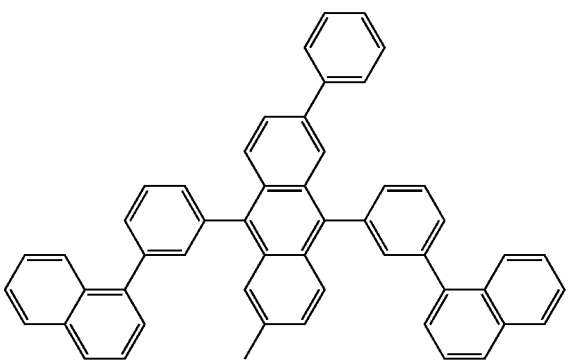

-continued

[Chemical Formula H-47]

[Chemical Formula H-48]

[Chemical Formula H-49]

[Chemical Formula H-50]

[Chemical Formula H-51]

[Chemical Formula H-52]

[Chemical Formula H-53]
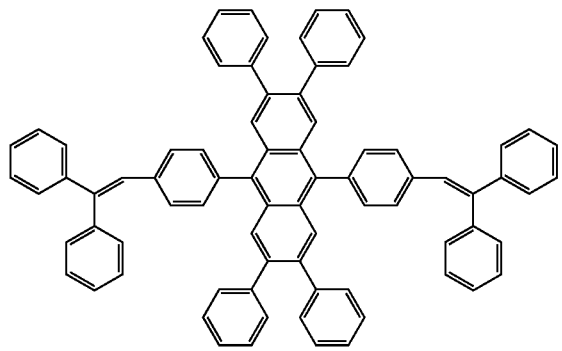
[Chemical Formula H-54]
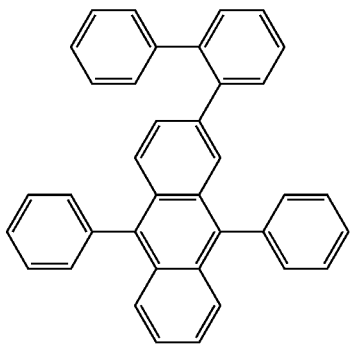
[Chemical Formula H-55]
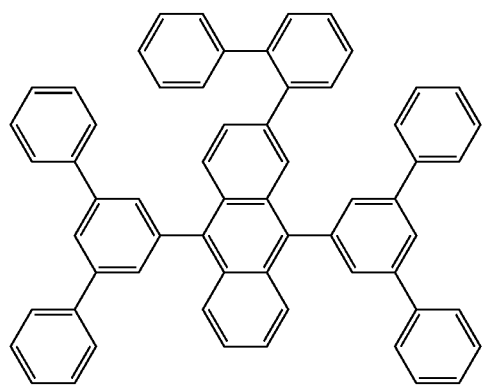
[Chemical Formula H-56]
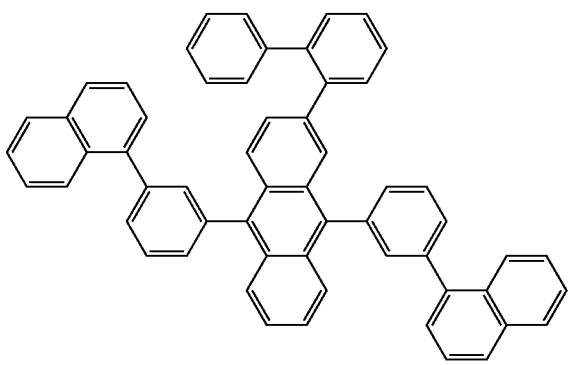
[Chemical Formula H-57]
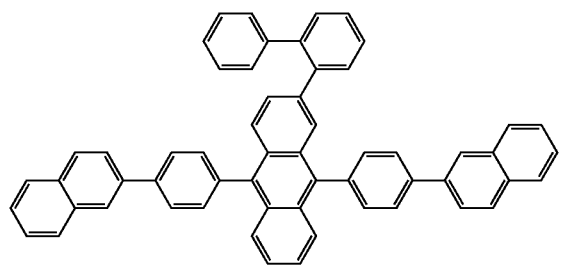
[Chemical Formula H-58]
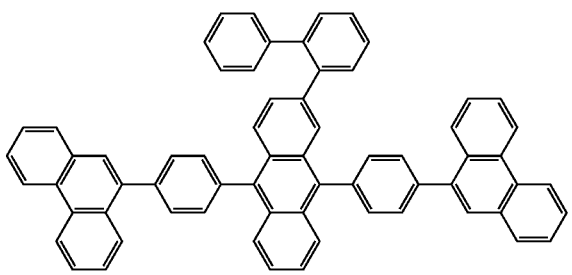
[Chemical Formula H-59]
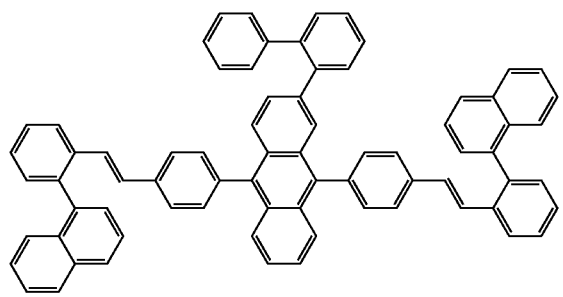
[Chemical Formula H-60]
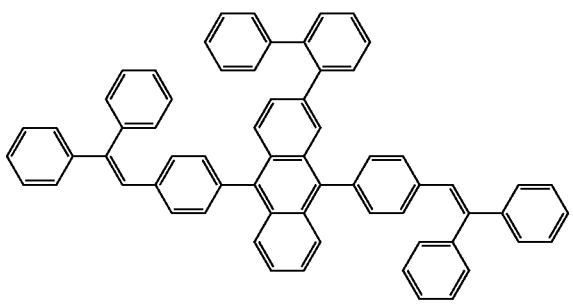

-continued
[Chemical Formula H-61]
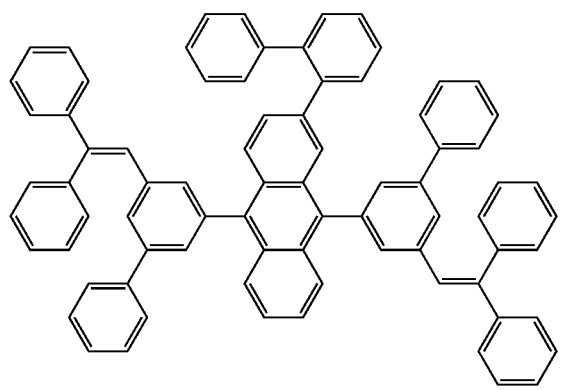
[Chemical Formula H-62]
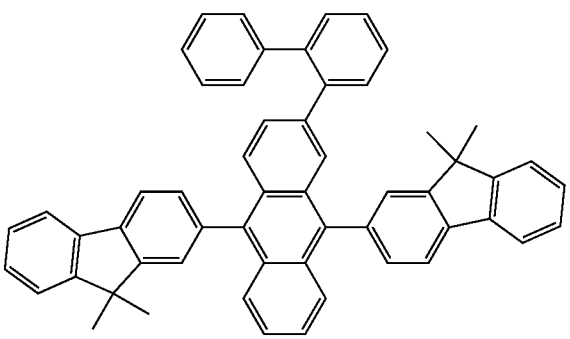
[Chemical Formula H-63]
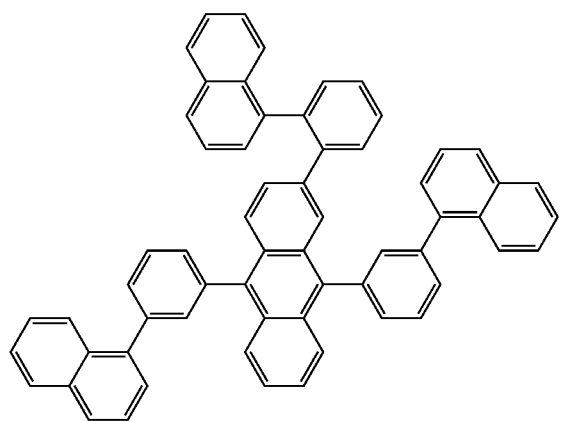
[Chemical Formula H-64]
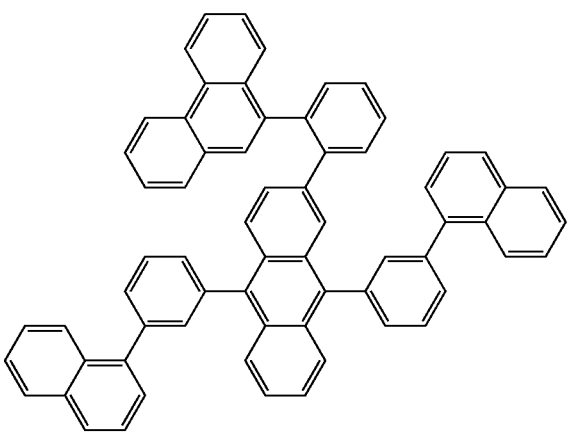
[Chemical Formula H-65]
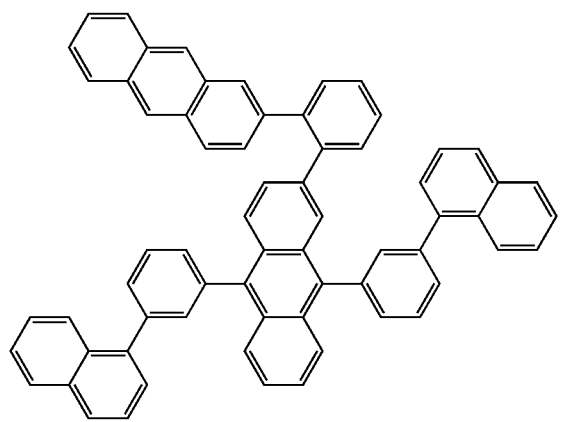
[Chemical Formula H-66]
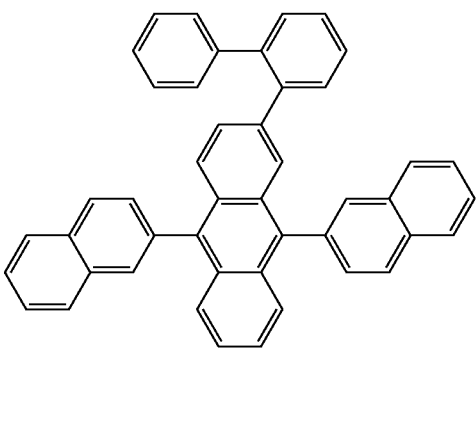

[Chemical Formula H-67]
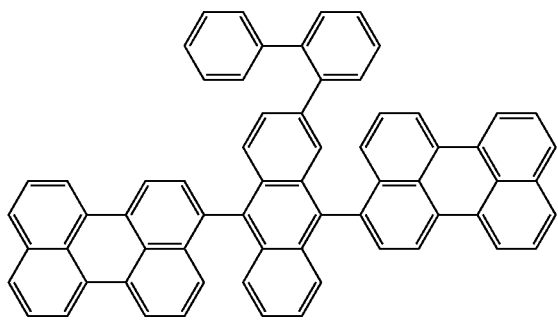
[Chemical Formula H-68]
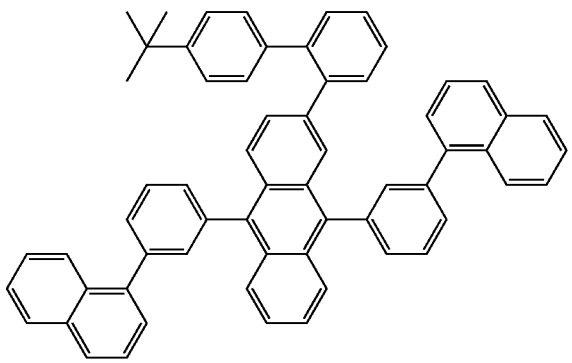
[Chemical Formula H-69]
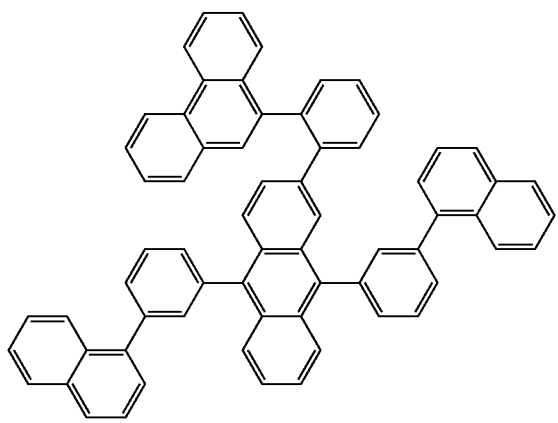
[Chemical Formula H-70]
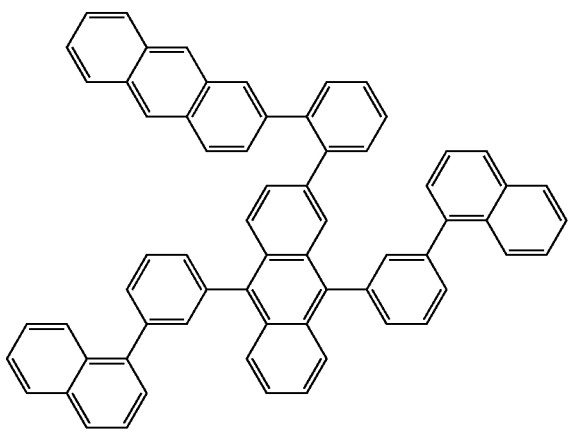
[Chemical Formula H-71]
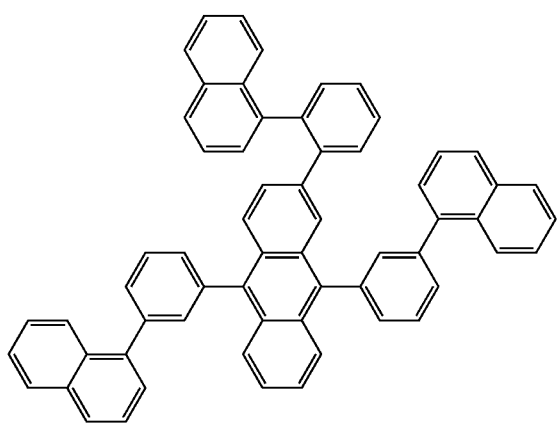
[Chemical Formula H-72]
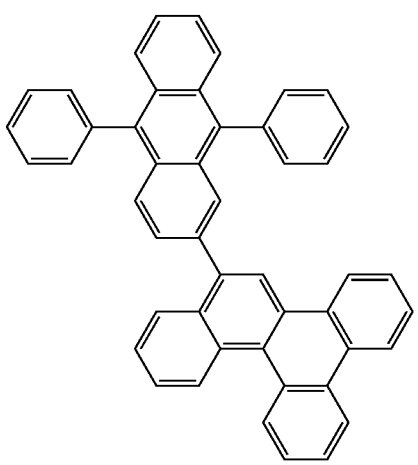

[Chemical Formula H-73]
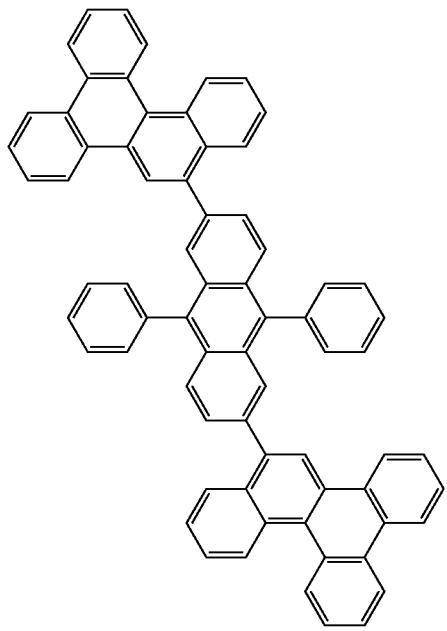
[Chemical Formula H-74]
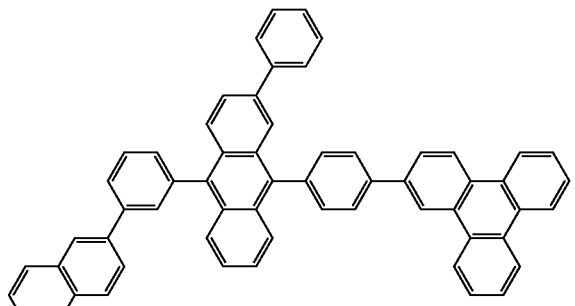
[Chemical Formula H-75]
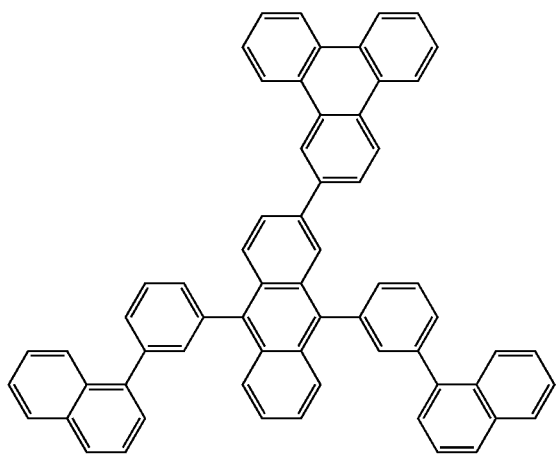
[Chemical Formula H-76]
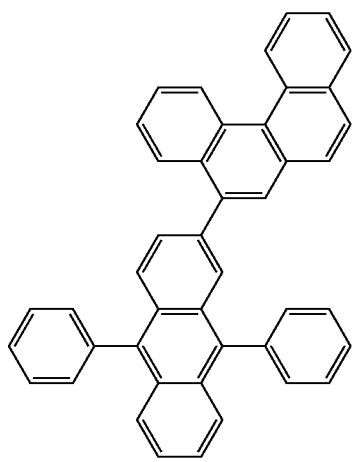
[Chemical Formula H-77]
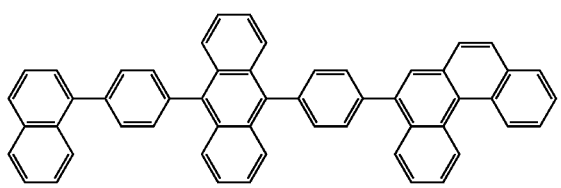
[Chemical Formula H-78]
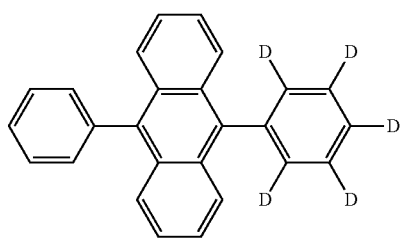
[Chemical Formula H-79]
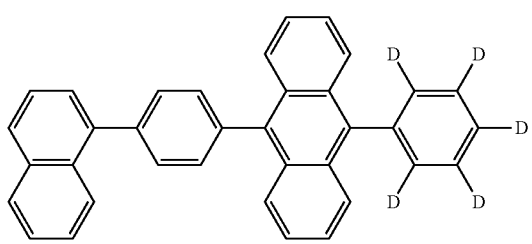
[Chemical Formula H-80]
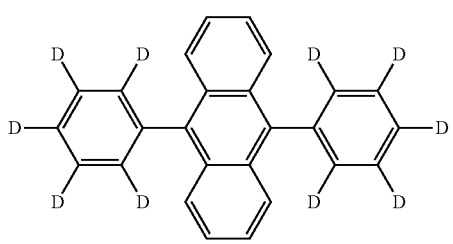

[Chemical Formula H-81]
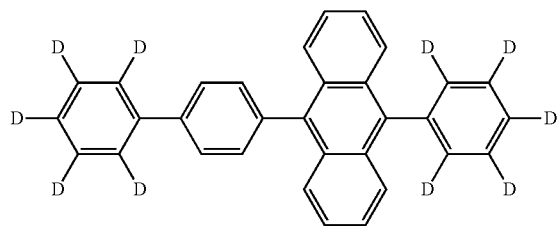
[Chemical Formula H-82]
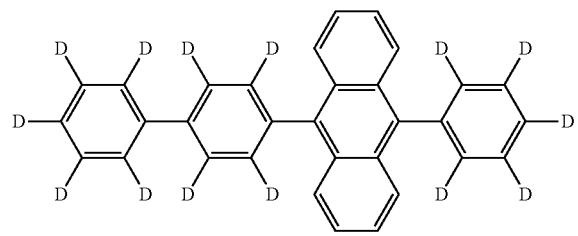
[Chemical Formula H-83]
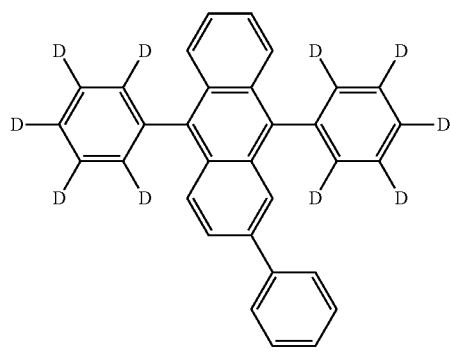
[Chemical Formula H-84]
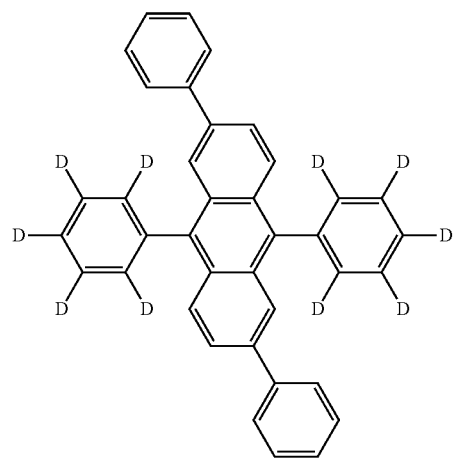
[Chemical Formula H-85]
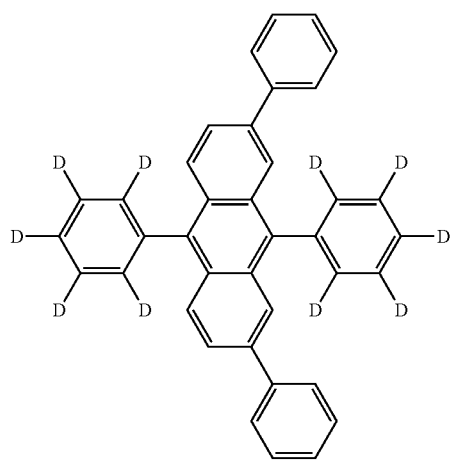
[Chemical Formula H-86]
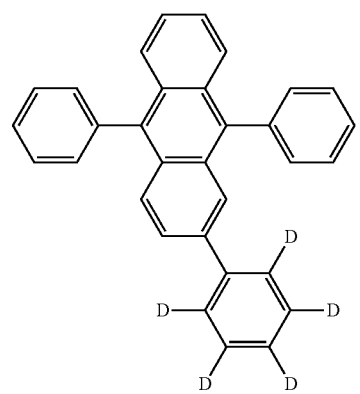

-continued
[Chemical Formula H-87]
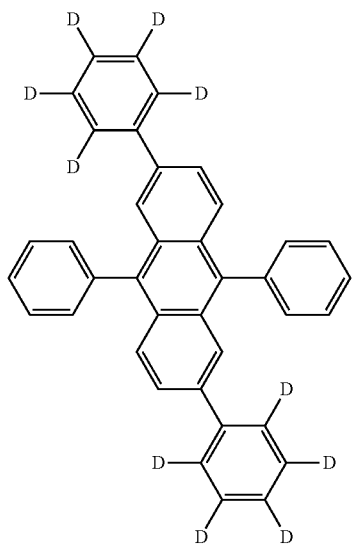
[Chemical Formula H-88]
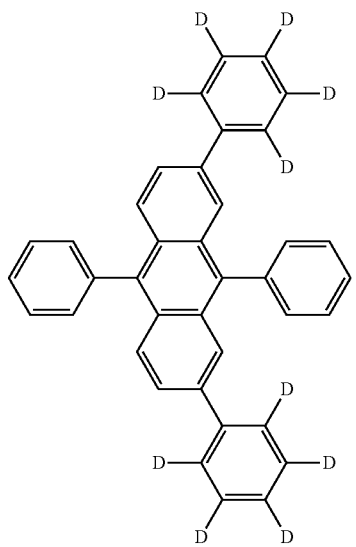
[Chemical Formula H-89]
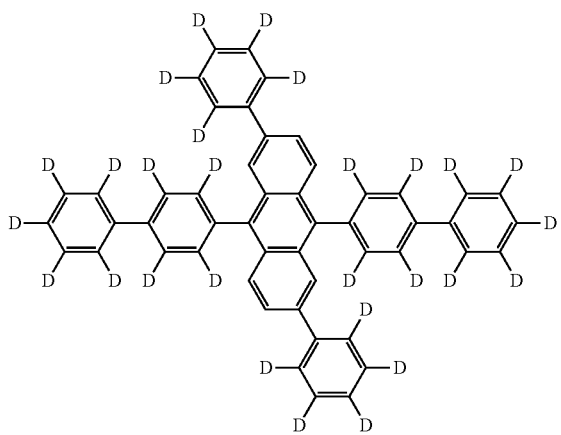
[Chemical Formula H-90]
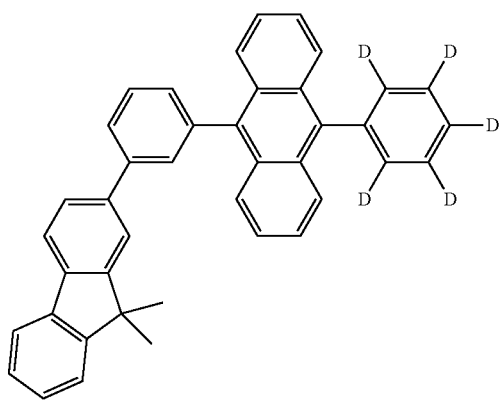
[Chemical Formula H-91]
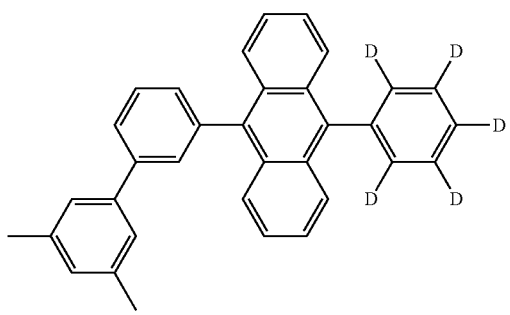
[Chemical Formula H-92]
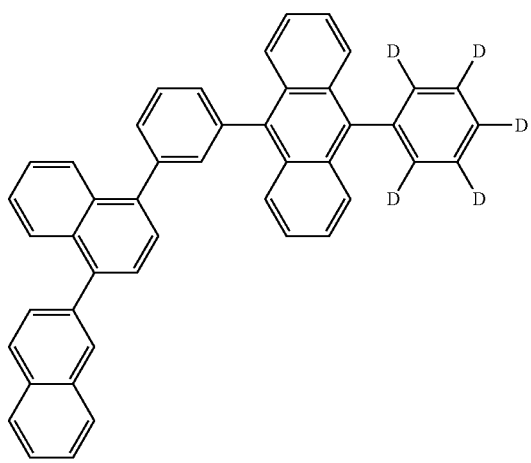

[Chemical Formula H-93]
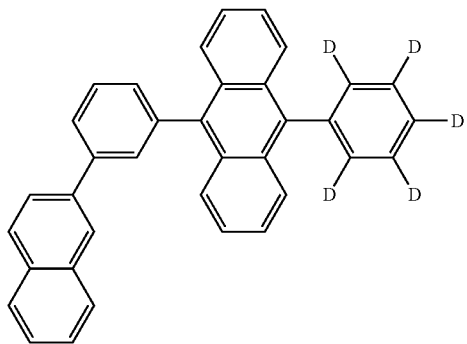
[Chemical Formula H-94]
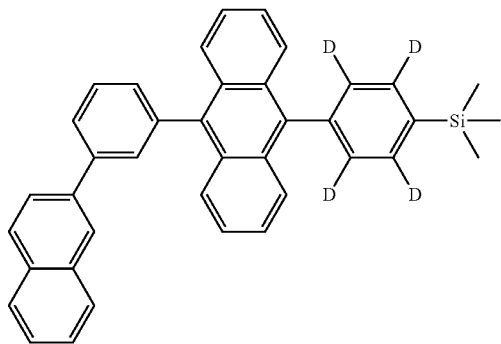
[Chemical Formula H-95]
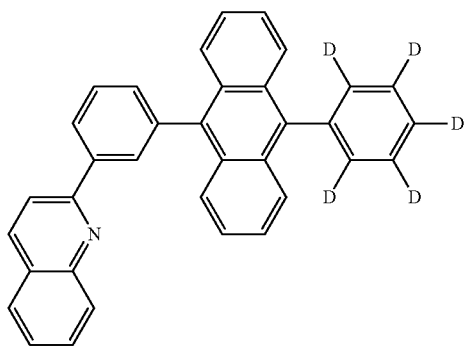
[Chemical Formula H-96]
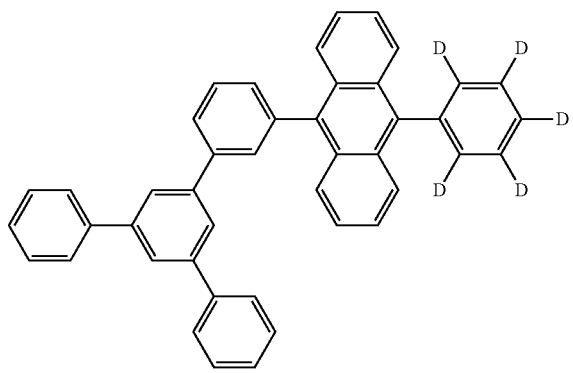
[Chemical Formula H-97]
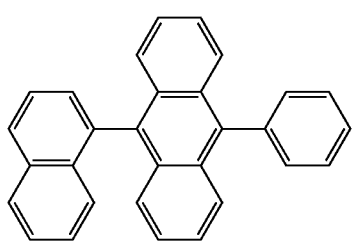
[Chemical Formula H-98]
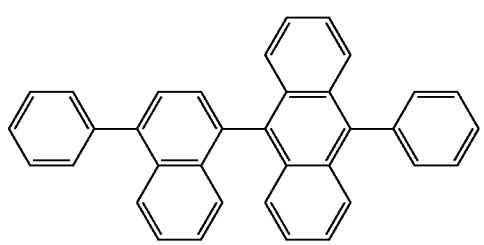
[Chemical Formula H-99]
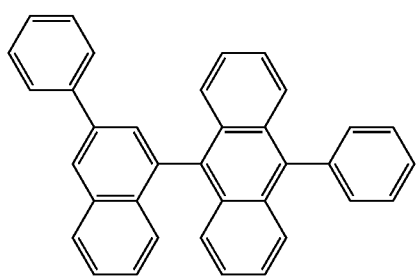
[Chemical Formula H-100]
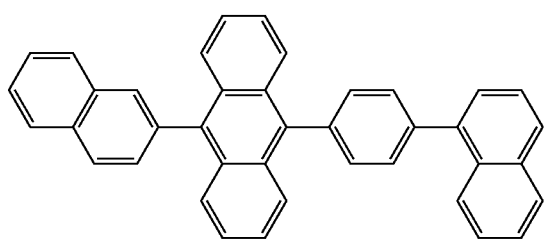
[Chemical Formula H-101]
[Chemical Formula H-102]
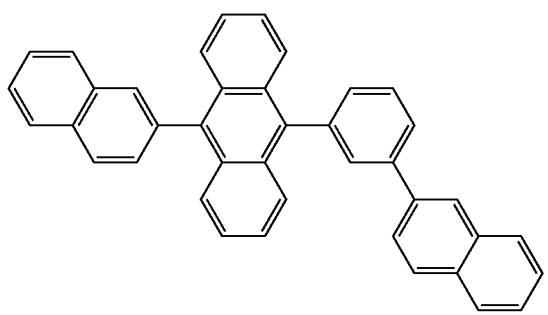

-continued
[Chemical Formula H-103]
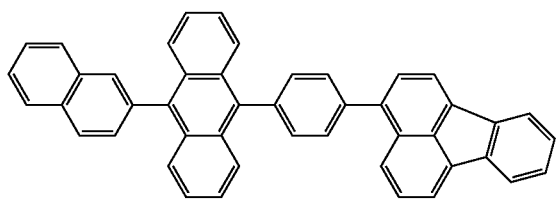
[Chemical Formula H-104]
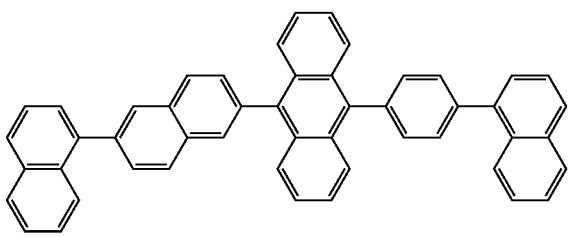
[Chemical Formula H-105]
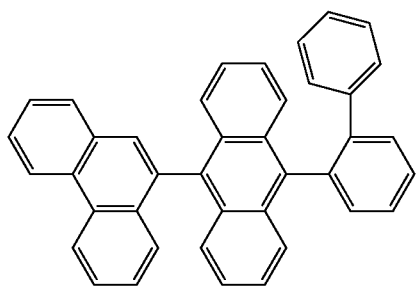
[Chemical Formula H-106]
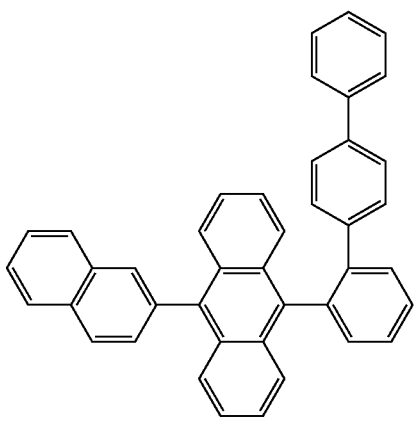
[Chemical Formula H-107]
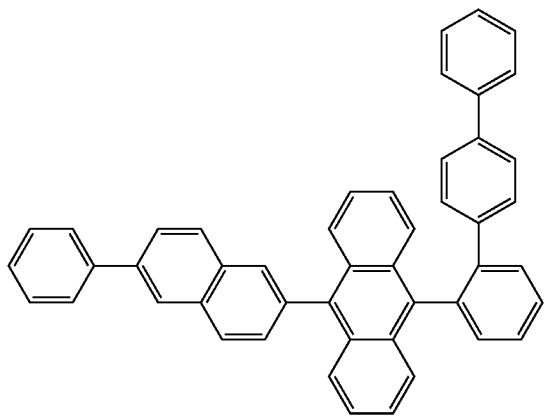
[Chemical Formula H-108]
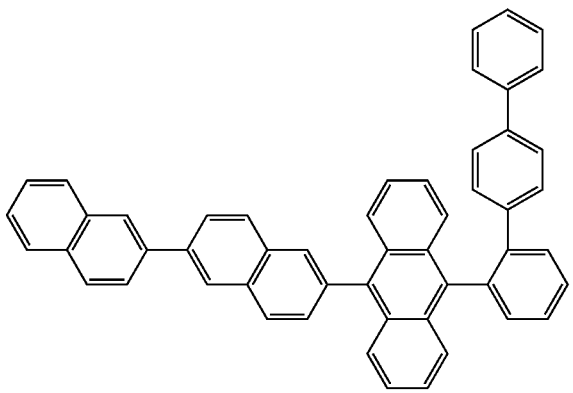
[Chemical Formula H-109]
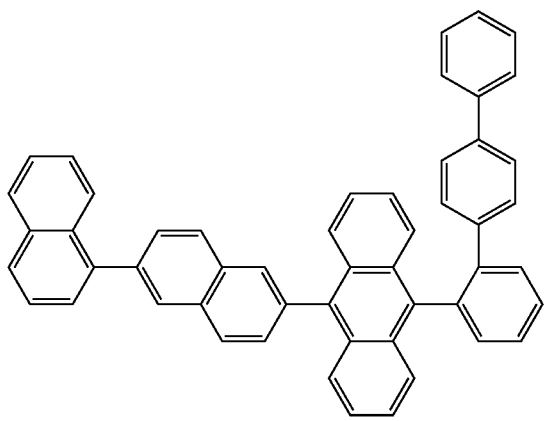
[Chemical Formula H-110]
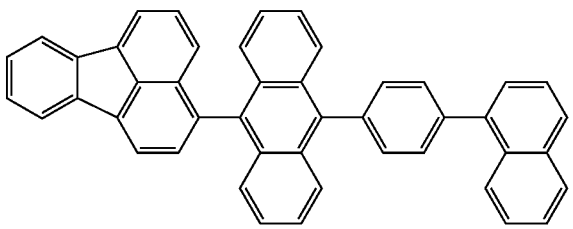

[Chemical Formula H-111]
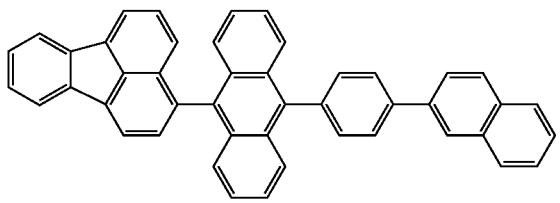
[Chemical Formula H-112]
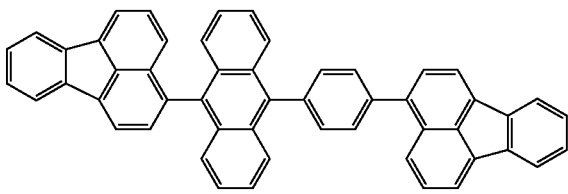
[Chemical Formula H-113]
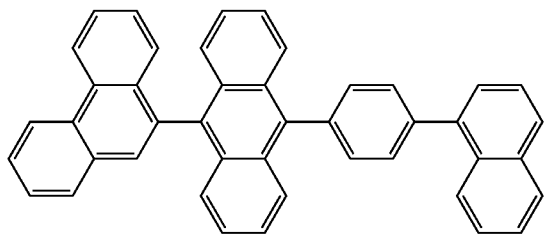
[Chemical Formula H-114]
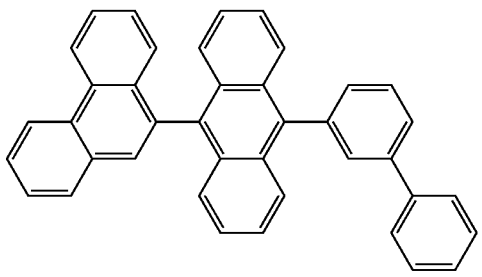
[Chemical Formula H-115]
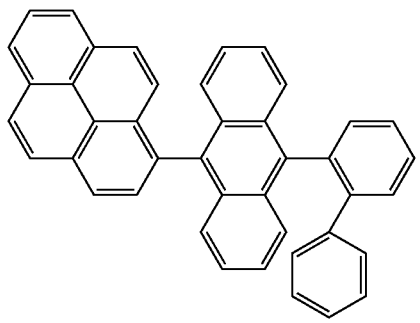
[Chemical Formula H-116]
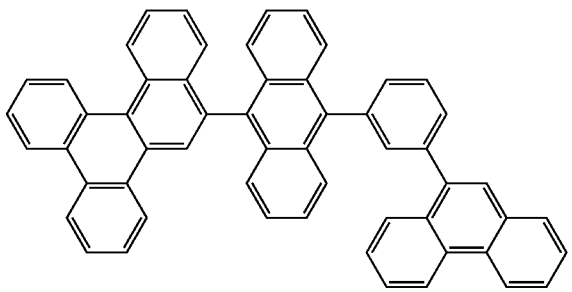
[Chemical Formula H-117]
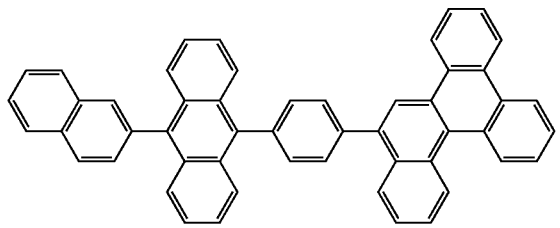
[Chemical Formula H-118]
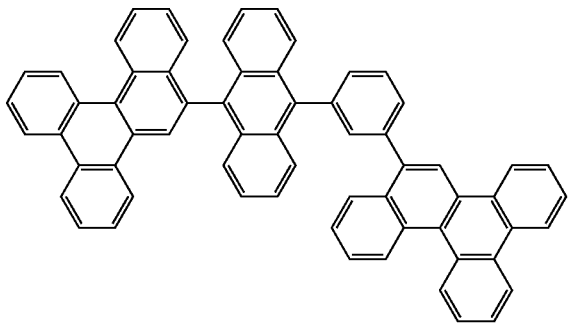
[Chemical Formula H-119]
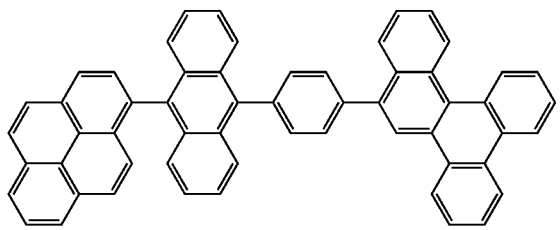
[Chemical Formula H-120]
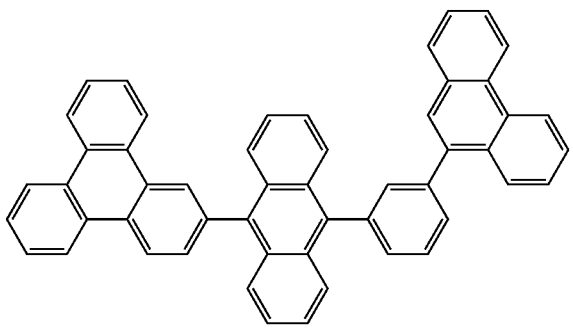

-continued
[Chemical Formula H-121]
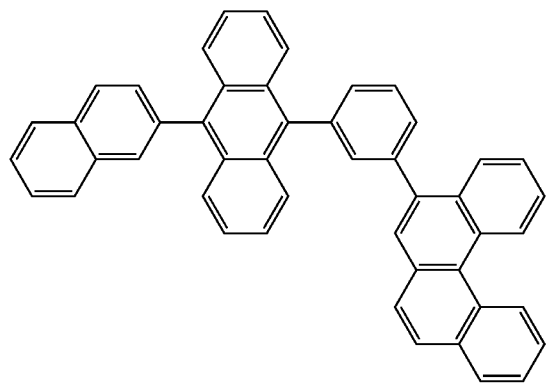
[Chemical Formula H-122]
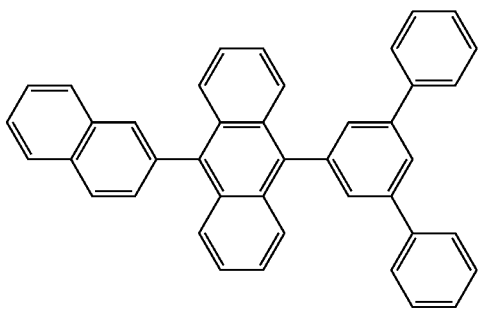
[Chemical Formula H-123]
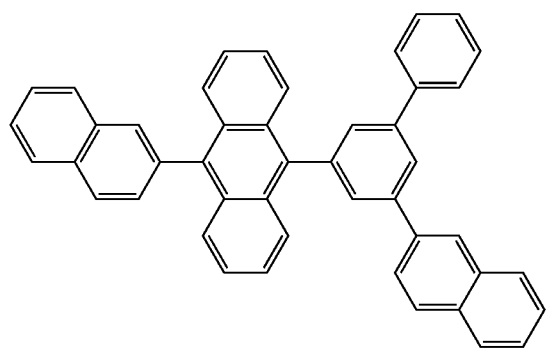
[Chemical Formula H-124]
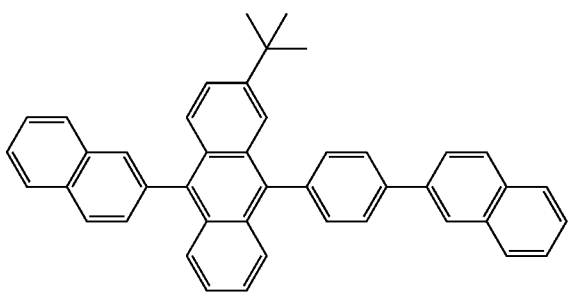
[Chemical Formula H-125]
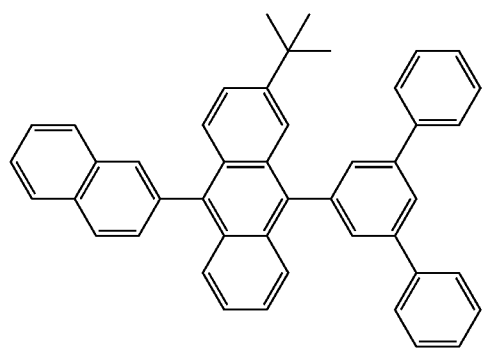
[Chemical Formula H-126]
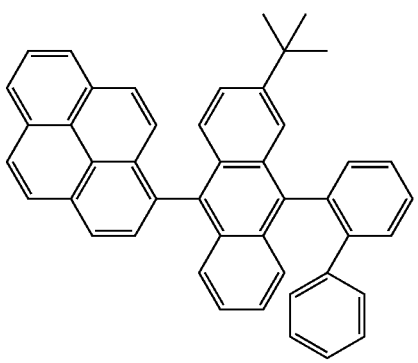
[Chemical Formula H-127]
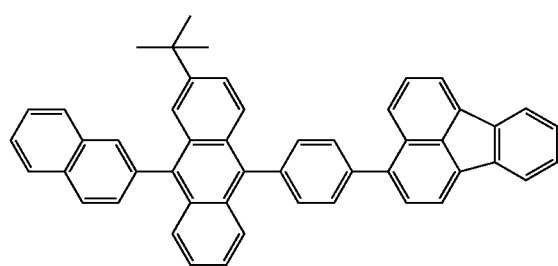
[Chemical Formula H-128]
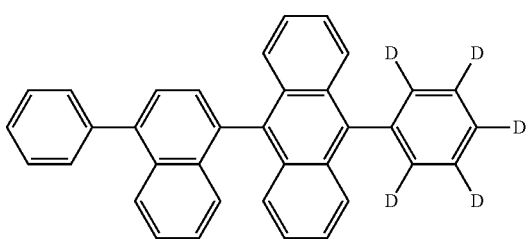

[Chemical Formula H-129]
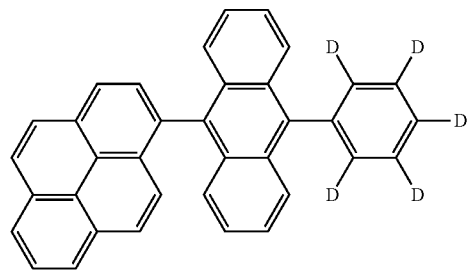
[Chemical Formula H-130]
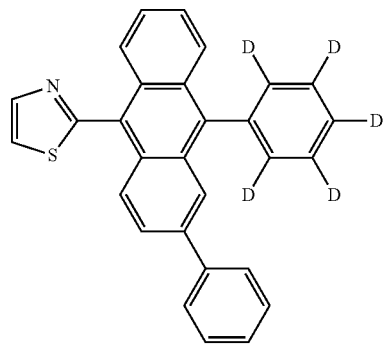
[Chemical Formula H-131]
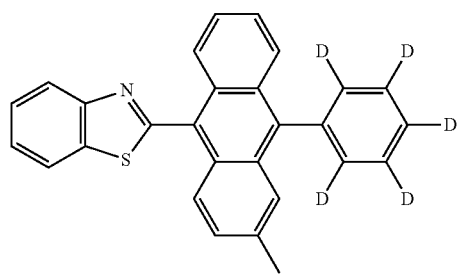
[Chemical Formula H-132]
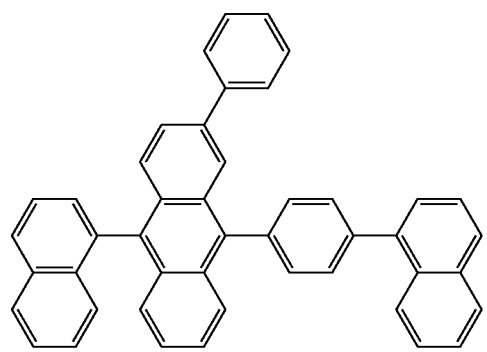
[Chemical Formula H-133]
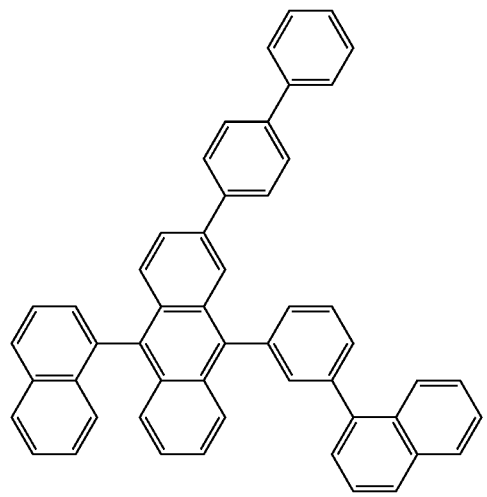
[Chemical Formula H-134]
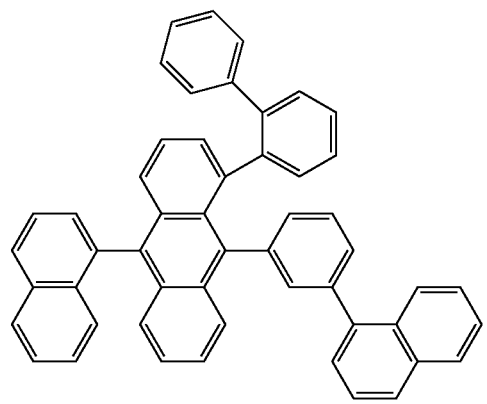

-continued
[Chemical Formula H-135]
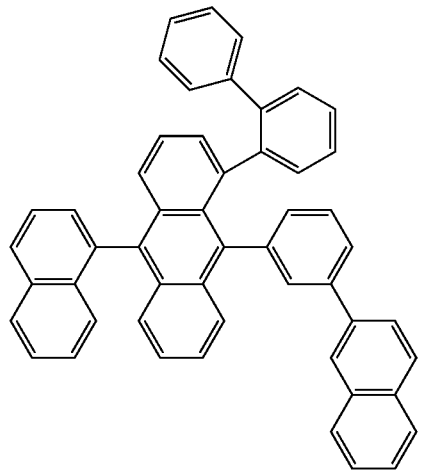
[Chemical Formula H-136]
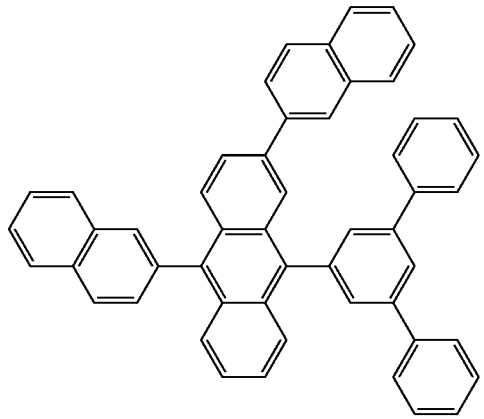
[Chemical Formula H-137]
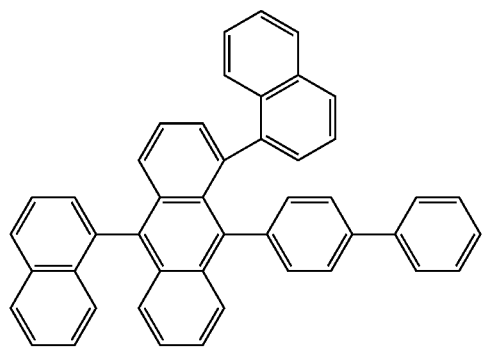
[Chemical Formula H-138]
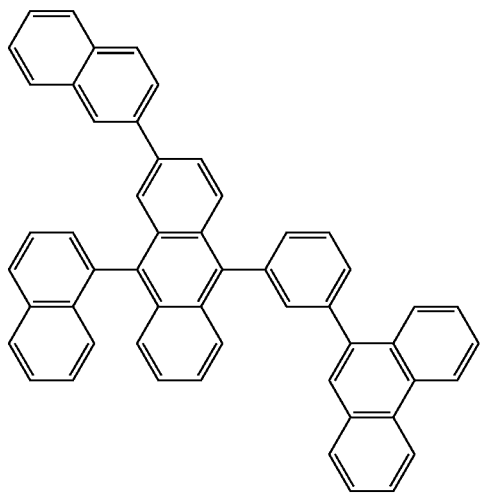
[Chemical Formula H-139]
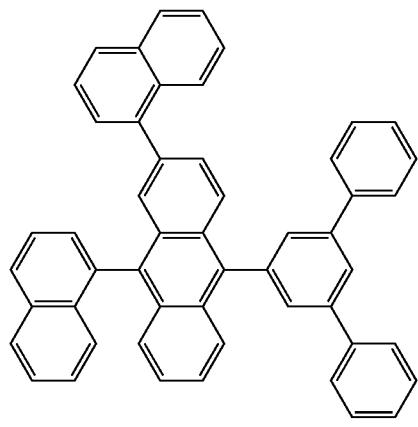
[Chemical Formula H-140]
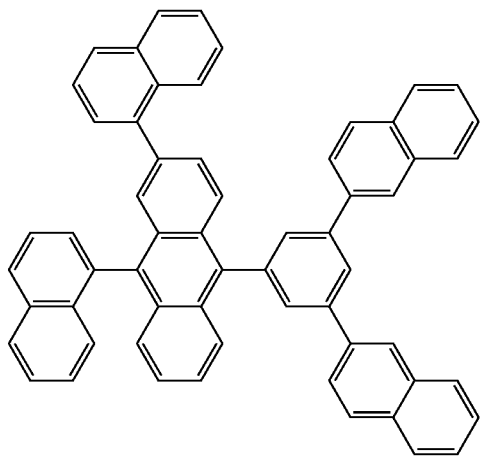

[Chemical Formula H-141]
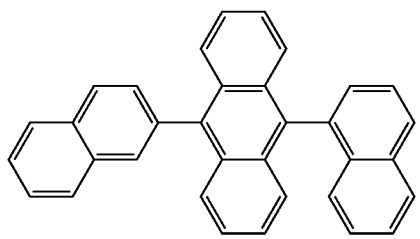
[Chemical Formula H-142]
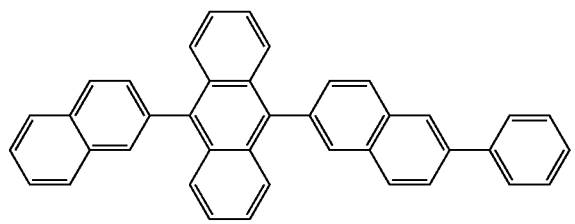
[Chemical Formula H-143]
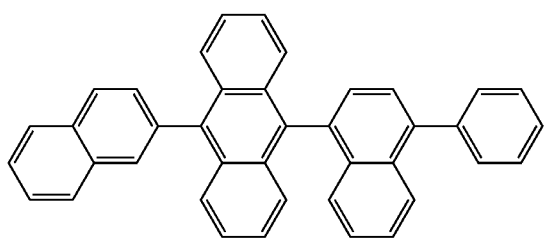
[Chemical Formula H-144]
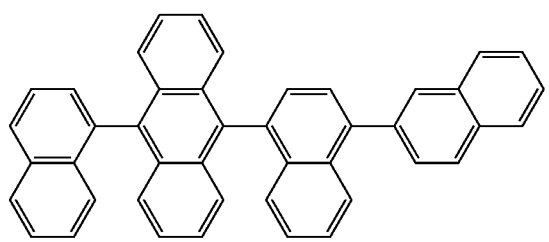
[Chemical Formula H-145]
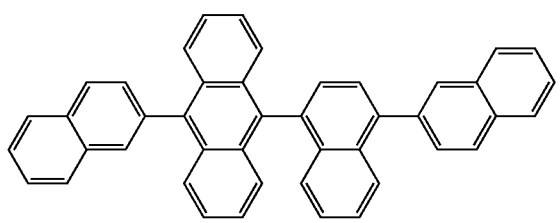
[Chemical Formula H-146]
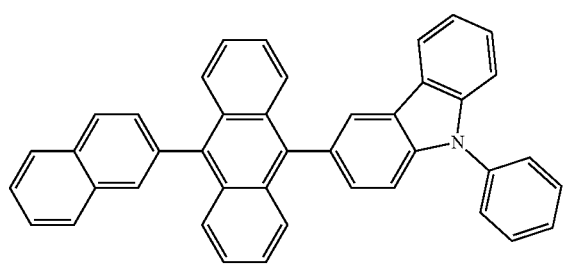
[Chemical Formula H-147]
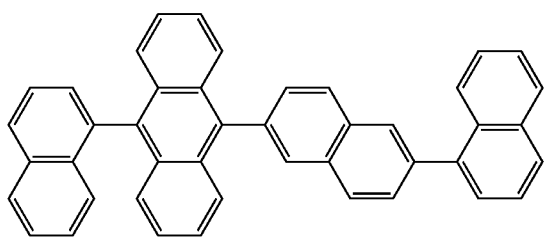
[Chemical Formula H-148]
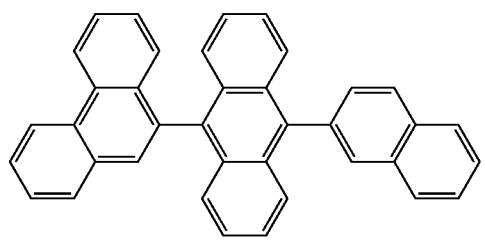
[Chemical Formula H-149]
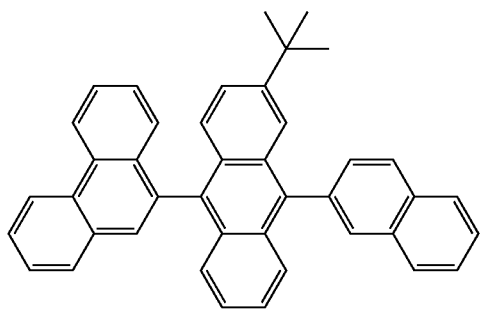
[Chemical Formua H-150]
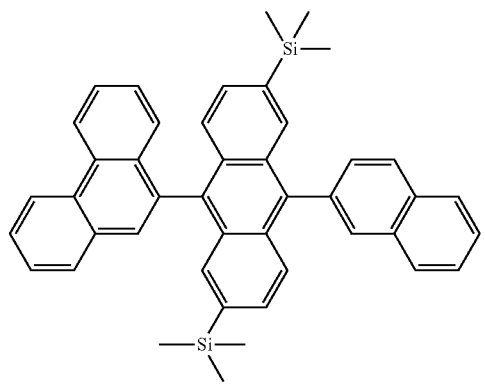

[Chemical Formula H-151]
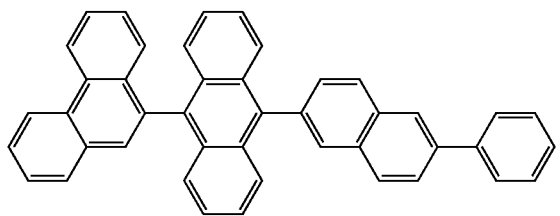
[Chemical Formula H-152]
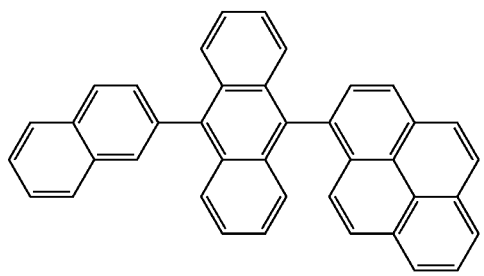
[Chemical Formula H-153]
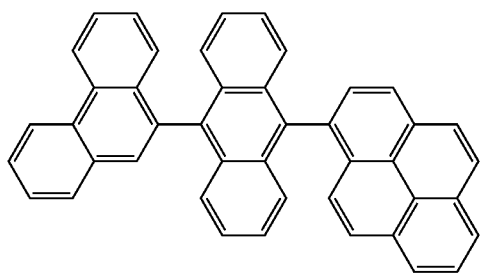
[Chemical Formula H-154]
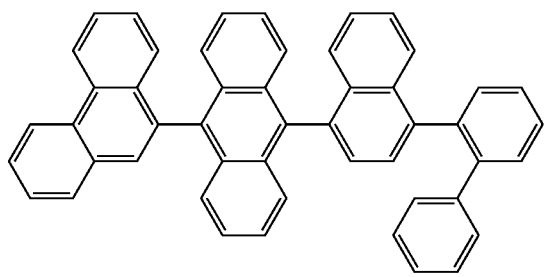
[Chemical Formula H-155]
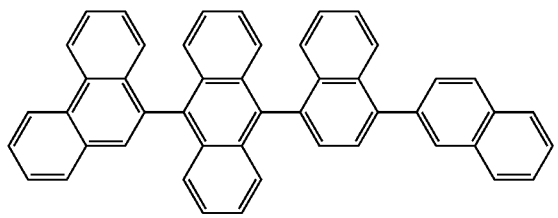
[Chemical Formula H-156]
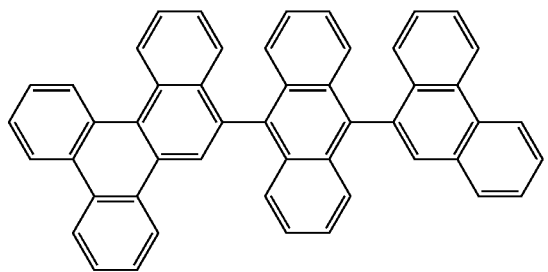
[Chemical Formula H-157]
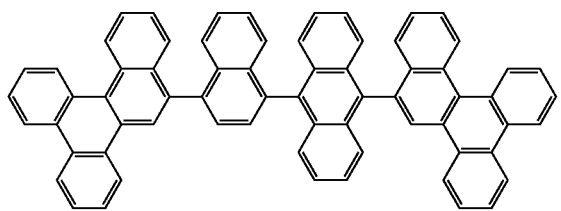
[Chemical Formula H-158]
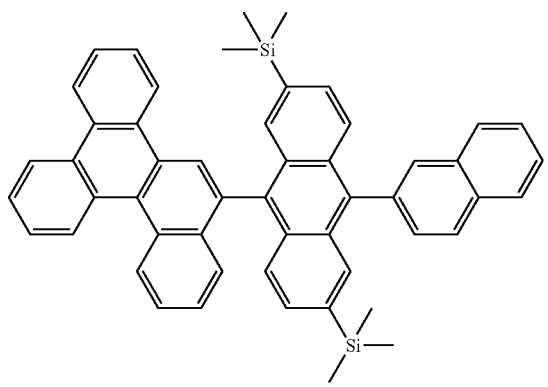

-continued
[Chemical Formula H-159]
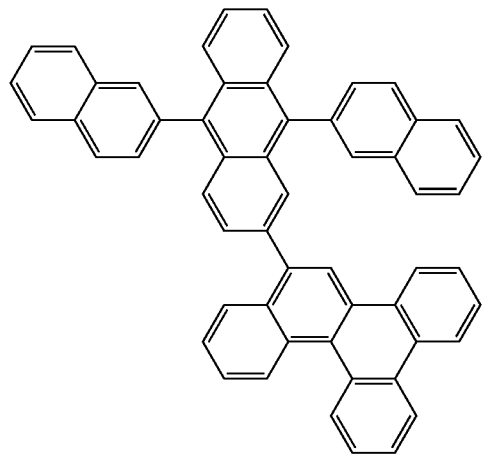
[Chemical Formula H-160]
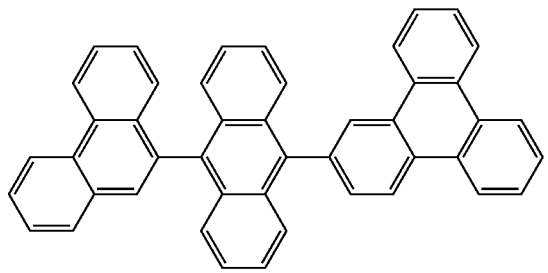
[Chemical Formula H-161]
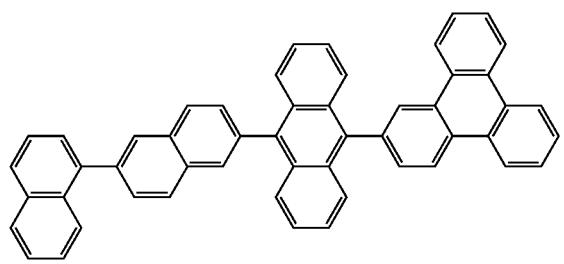
[Chemical Formula H-162]
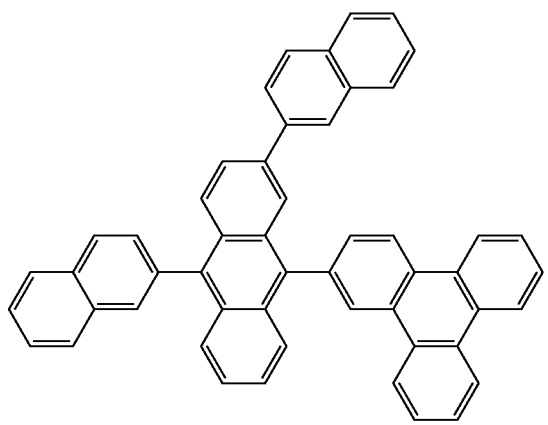
[Chemical Formula H-163]
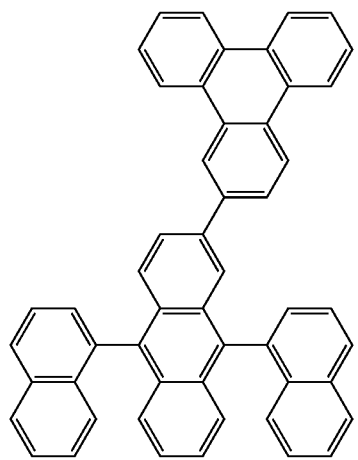
[Chemical Formula H-164]
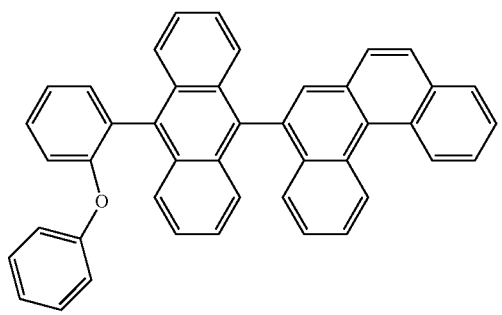

[Chemical Formula H-165]
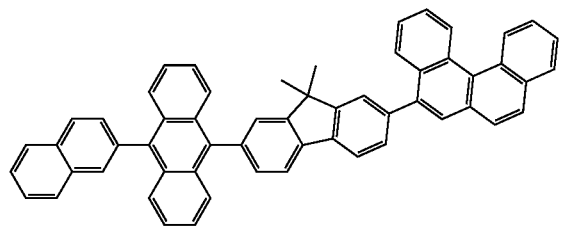
[Chemical Formula H-166]
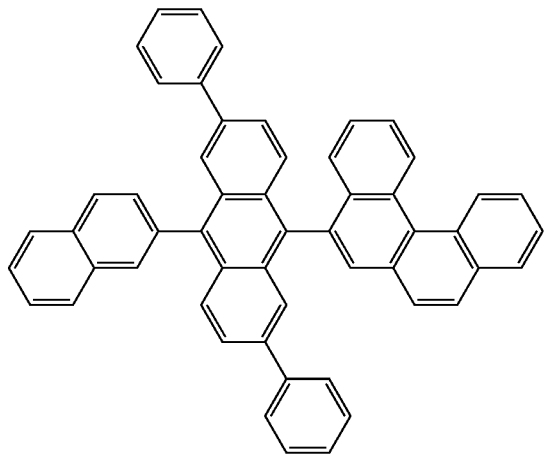
[Chemical Formula H-167]
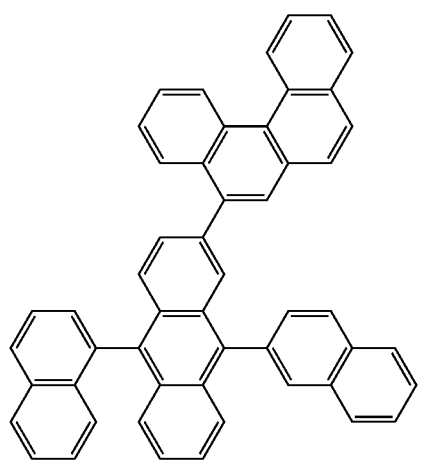
[Chemical Formula H-168]
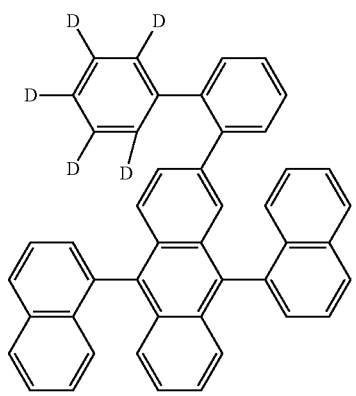
[Chemical Formula H-169]
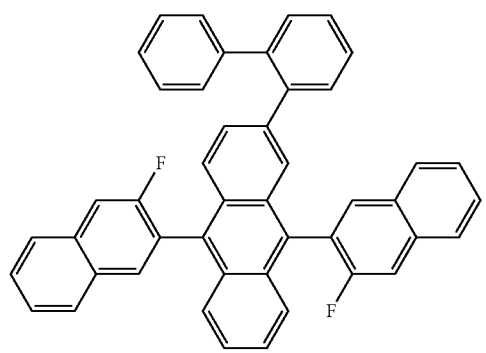
[Chemical Formula H-170]
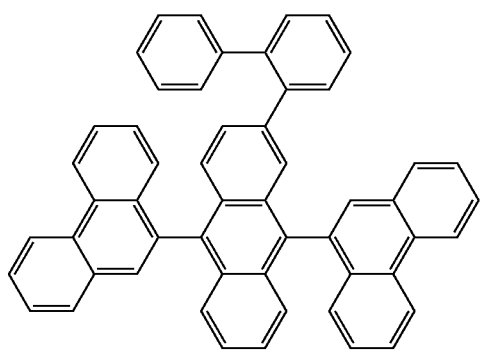

-continued
[Chemical Formula H-171]
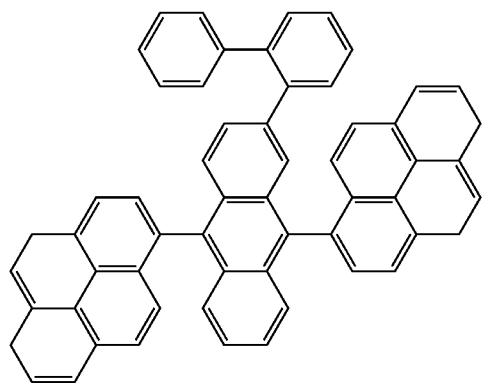
[Chemical Formula H-172]
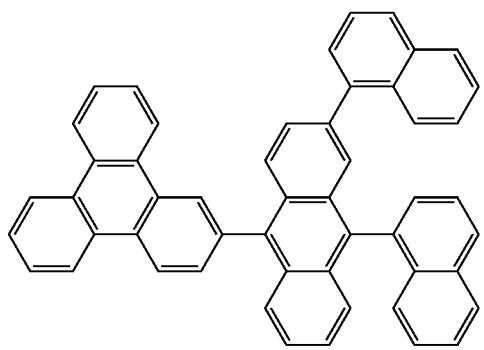
[Chemical Formula H-173]
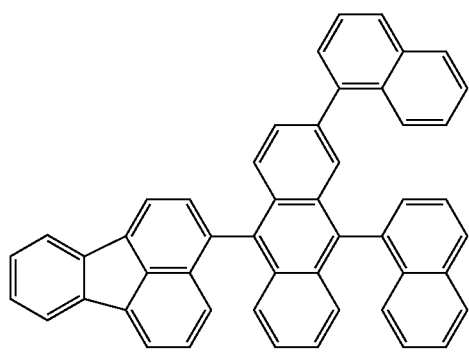
[Chemical Formula H-174]
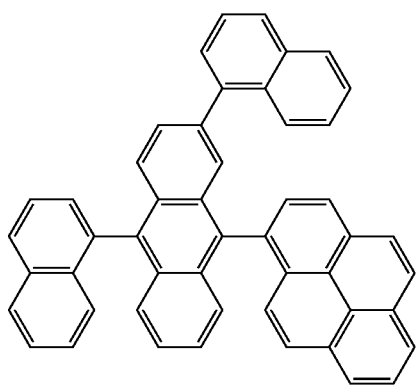
[Chemical Formula H-175]
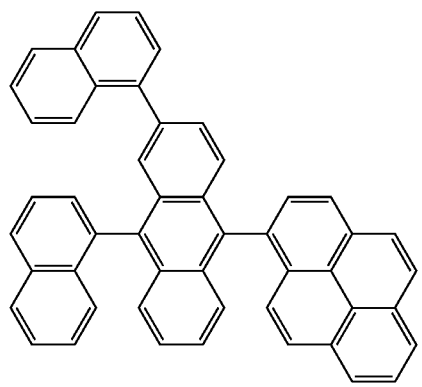
[Chemical Formula H-176]
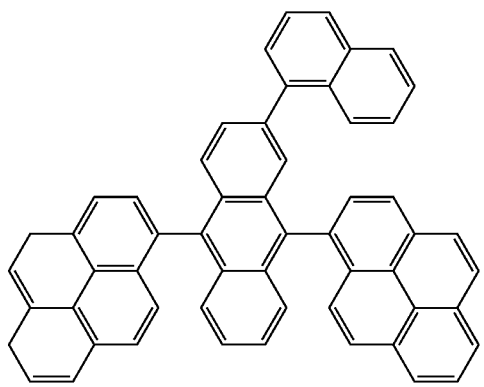

-continued
[Chemical Formula H-177]
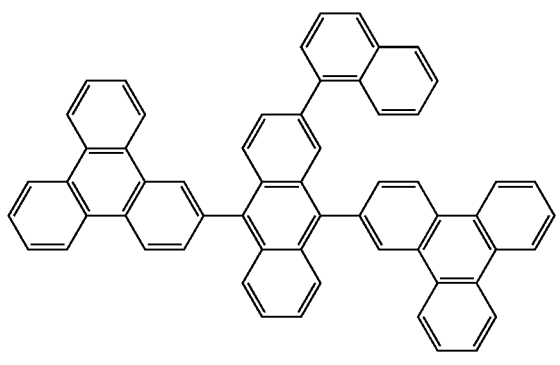
[Chemical Formula H-178]
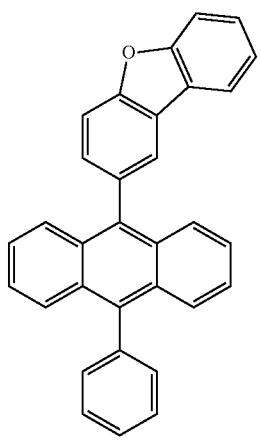
[Chemical Formula H-179]
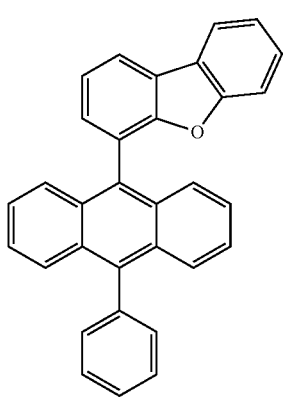
[Chemical Formula H-180]
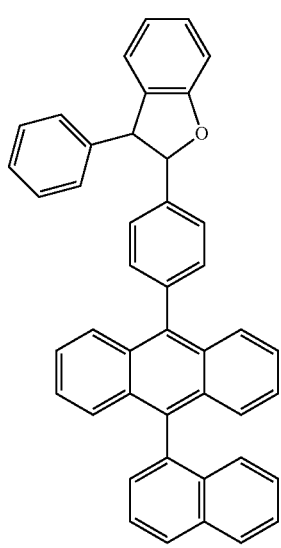
[Chemical Formula H-181]
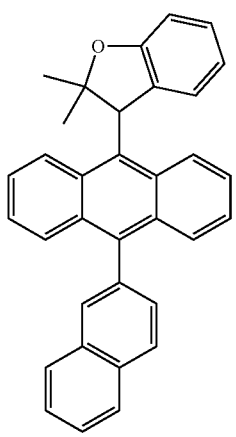
[Chemical Formula H-182]
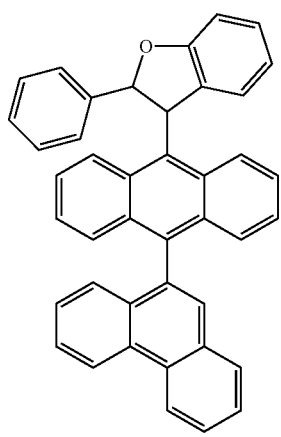

-continued
[Chemical Formula H-183]
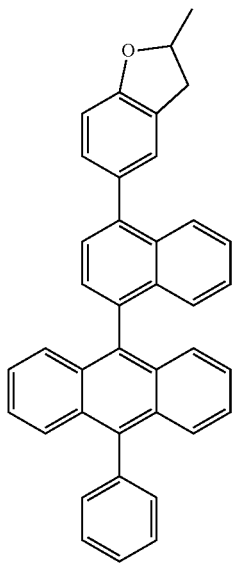
[Chemical Formula H-184]
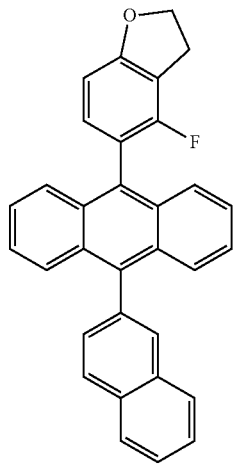
[Chemical Formula H-185]
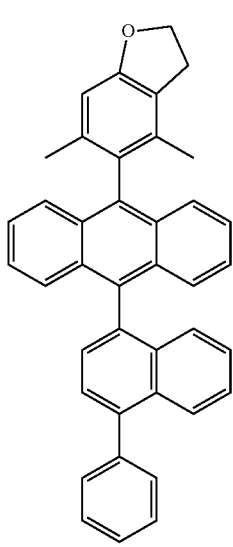
[Chemical Formula H-186]
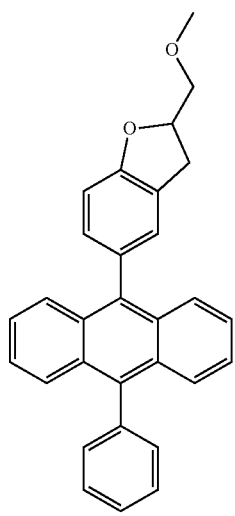
[Chemical Formula H-187]
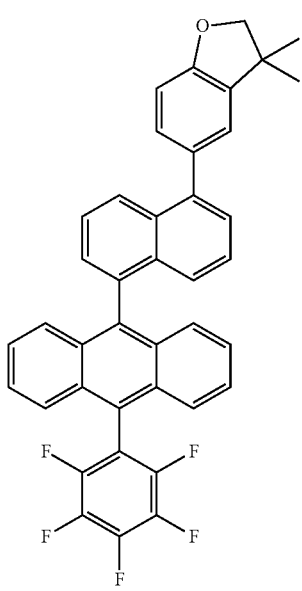
[Chemical Formula H-188]
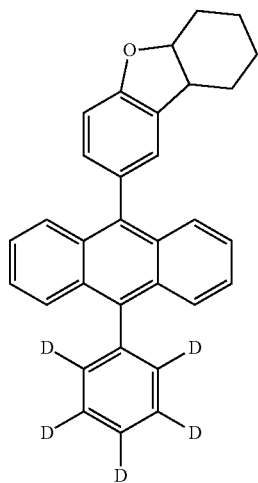

[Chemical Formula H-189]
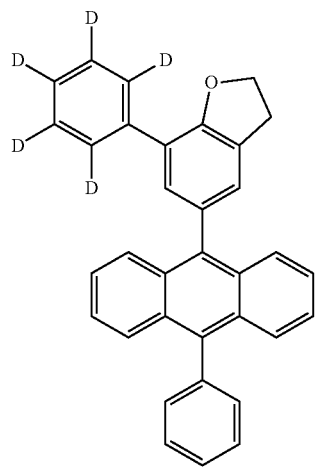
[Chemical Formula H-190]
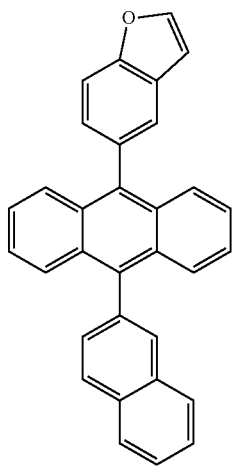
[Chemical Formula H-191]
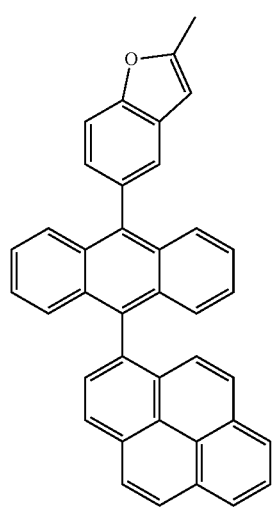
[Chemical Formula H-192]
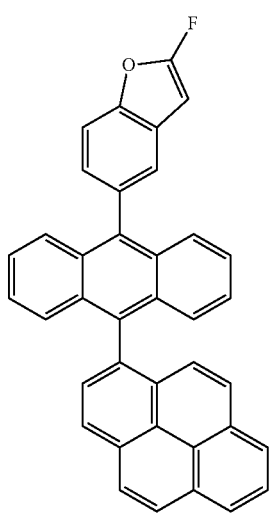
[Chemical Formula H-193]
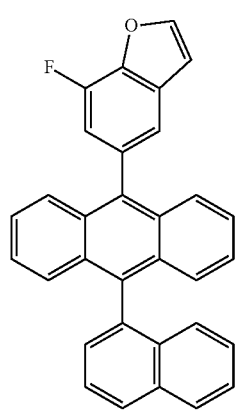
[Chemical Formula H-194]
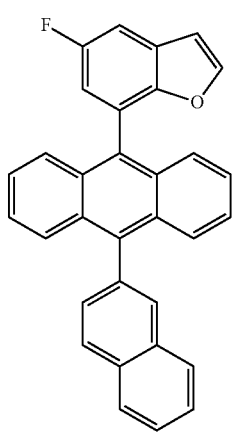

[Chemical Formula H-195]

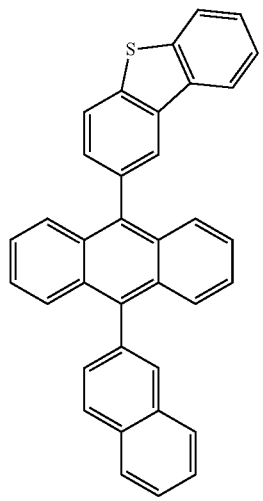

[Chemical Formula H-196]

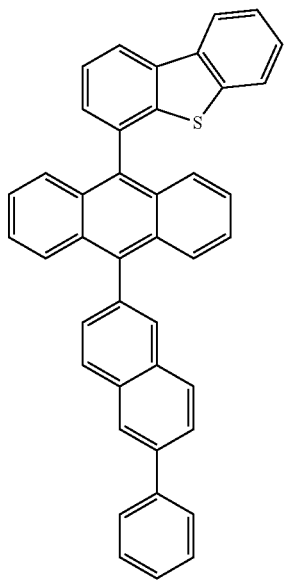

In addition, the light emitting layer of the present disclosure may contain as a dopant compound at least one of the compounds represented by the following Chemical Formula 2 to Chemical Formula 6:

[Chemical Formula 2]

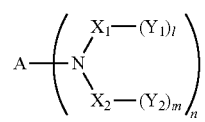

[Chemical Formula 3]

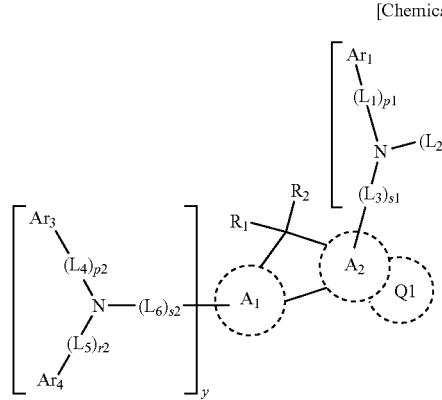

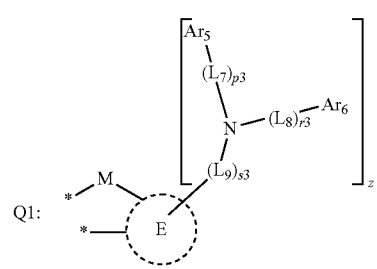

[Chemical Formula 4]

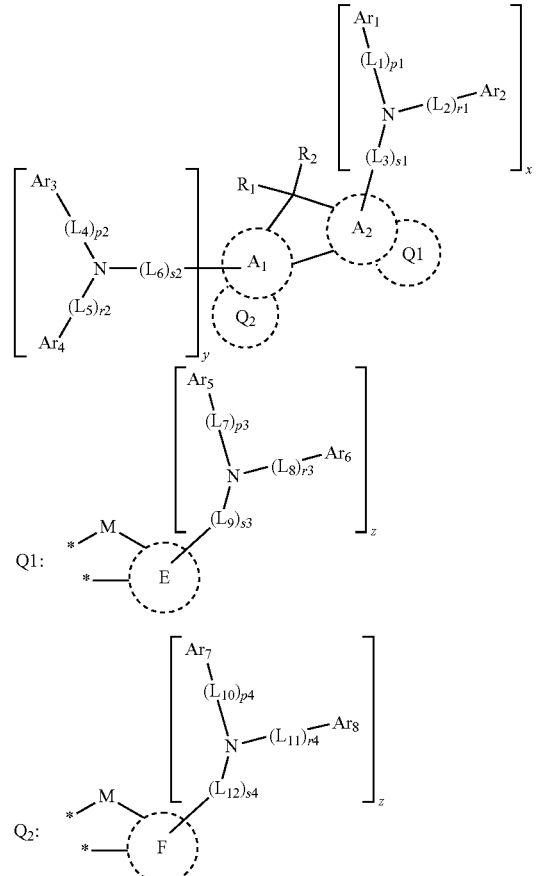

wherein,

A in Chemical Formula 2 is any one selected from a substituted or unsubstituted aryl of 5 to 50 carbon atoms, a substituted or unsubstituted heteroaryl of 3 to 50 carbon atoms bearing O, N, or S as a heteroatom, a substituted or unsubstituted arylene of 6 to 60 carbon atoms, and a substituted or unsubstituted heteroarylene of 3 to 50 carbon atoms bearing O, N, or S as a heteroatom.

Preferable is anthracene, pyrene, phenanthrene, indenophenanthrene, chrysene, naphthacene, picene, triphenylene, perylene, or pentacene. In this regard, A may be any one of the compounds represented by the following Chemical Formula A1 to Chemical Formula A10:

[Chemical Formula A1]

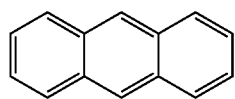

[Chemical Formula A2]

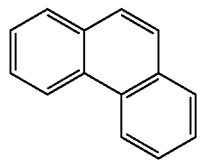

[Chemical Formula A3]

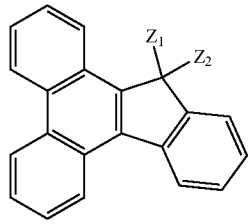

[Chemical Formula A4]

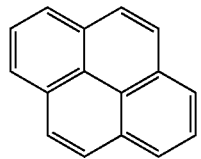

[Chemical Formula A5]

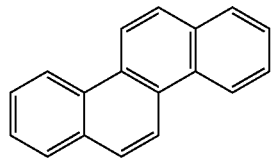

[Chemical Formula A6]

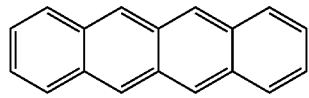

[Chemical Formula A7]

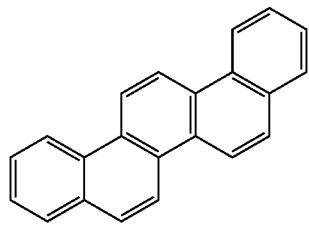

[Chemical Formula A8]

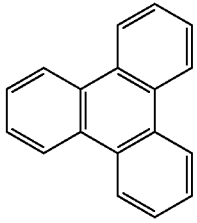

[Chemical Formula A9]

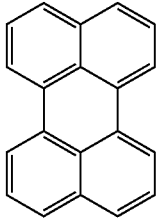

[Chemical Formula A10]

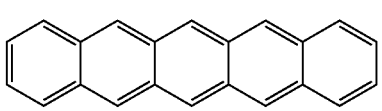

wherein, $Z_1$ and $Z_2$ in Chemical Formula A3, which may be same or different, are each independently selected from the group consisting of a hydrogen atom, a deuterium atom, a substituted or unsubstituted alkyl of 1 to 60 carbon atoms, a substituted or unsubstituted alkenyl of 2 to 60 carbon atoms, a substituted or unsubstituted alkynyl of 2 to 60 carbon atoms, a substituted or unsubstituted alkoxy of 1 to 60 carbon atoms, a substituted or unsubstituted alkylthio of 1 to 60 carbon atoms, a substituted or unsubstituted cycloalkyl of 3 to 60 carbon atoms, a substituted or unsubstituted aryl of 6 to 60 carbon atoms, a substituted or unsubstituted aryloxy of 5 to 60 carbon atoms, a substituted or unsubstituted arylthio of 5 to 60 carbon atoms, a substituted or unsubstituted heteroaryl of 2 to 60 carbon atoms, a substituted or unsubstituted (alkyl) amino of 1 to 60 carbon atoms, a di(substituted or unsubstituted alkyl of 1 to 60 carbon atoms)amino, of a (substituted or unsubstituted aryl of 6 to 60 carbon atoms)amino, and a di(substituted or unsubstituted aryl of 6 to 60 carbon atoms)amino and may each form a fused ring with a radical adjacent thereto, in Chemical Formula 2, $X_1$ and $X_2$, which may be the same or different, are each independently selected from a substituted or unsubstituted arylene of 6 to 30 carbon atoms and a single bond, and may be bonded to each other;

$Y_1$ and $Y_2$, which may be same or different, are each independently selected from the group consisting of a substituted or unsubstituted aryl of 6 to 24 carbon atoms, a substituted or unsubstituted heteroaryl of 2 to 24 carbon atoms, a substituted or unsubstituted alkyl of 1 to 24 carbon atoms, a substituted or unsubstituted heteroalkyl of 1 to 24 carbon atoms, a substituted or unsubstituted cycloalkyl of 3 to 24 carbon atoms, a substituted or unsubstituted alkoxy of 1 to 24 carbon atoms, a cyano, a halogen, a substituted or unsubstituted aryloxy of 6 to 24 carbon atoms, a substituted or unsubstituted alkylsilyl of 1 to 40 carbon atoms, a substituted or unsubstituted arylsilyl of 6 to 30 carbon atoms, a germanium, a phosphorus, a boron, a deuterium atom, and a hydrogen atom, and may each form a fused aliphatic or aromatic ring or a fused aliphatic or aromatic heterering with an adjacent radical; and l, and m are each an integer of 1 to 20, and n is an integer of 1 to 4.

In Chemical Formula 3 and Chemical Formula 4, $A_1$, $A_2$, E, and F, which may be the same or different, are each independently a substituted or unsubstituted aromatic hydrocarbon ring of 6 to 50 carbon atoms, or a substituted or unsubstituted aromatic heterering of 2 to 40 carbon atoms wherein two adjacent carbon atoms of the aromatic ring $A_1$ and two adjacent carbon atoms of the aromatic ring $A_2$ form a 5-membered fused ring together with a carbon atom to which substituents $R_1$ and $R_2$ are bonded;

linkers $L_1$ to $L_{12}$, which may be the same or different, are each independently selected from a single bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

M is any one selected from N—$R_3$, $CR_4R_5$, $SiR_6R_7$, $GeR_8R_9$, O, S, and Se;

$R_1$ to $R_9$, and $Ar_1$ to $Ar_8$, which may be the same or different, are each independently any one of selected from a hydrogen atom, a deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a substituted or unsubstituted alkyl germanium of 1 to carbon atoms, a substituted or unsubstituted aryl germanium of 1 to 30 carbon atoms, a cyano, a nitro, and a halogen, wherein $R_1$ and $R_2$ together may form a mono- or polycyclic aliphatic or aromatic ring that may be a heterocyclic ring bearing a heteroatom selected from N, O, P, Si, S, Ge, Se, and Te as a ring member;

p1 to p4, r1 to r4, and s1 to s4 are each independently an integer of 1 to 3, wherein when any of them is 2 or greater, the corresponding $L_1$ to $L_{12}$ may be same or different, x is an integer of 1 or 2, and y and z may be same or different and are each independently an integer of 0 to 3;

$Ar_1$ may form a ring with $Ar_2$, $Ar_3$ may form a ring with $Ar_4$, $Ar_5$ may form a ring with $Ar_6$, and $Ar_7$ may form a ring with $Ar_8$;

two adjacent carbon atoms of the $A_2$ ring moiety of Chemical Formula 3 may occupy respective positions * of Structural Formula $Q_1$ to form a fused ring, and two adjacent carbon atoms of the $A_1$ ring moiety of Chemical Formula 4 may occupy respective positions * of structural Formula $Q_2$ to form a fused ring, and two adjacent carbon atoms of the $A_2$ ring moiety of Chemical Formula 4 may occupy respective positions * of Structural Formula $Q_1$ to form a fuse ring.

In addition, the amine moiety in Chemical Formulas 2 to 4 may be any one selected from the following [Substituent 1] to [Substituent 52], but is not limited thereto:

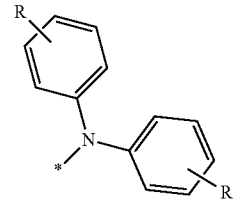

[Substituent1]

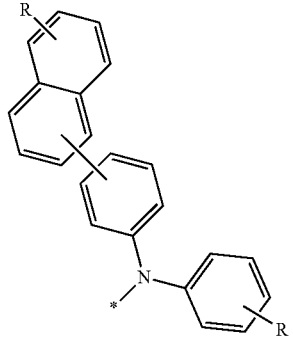

[Substituent2]

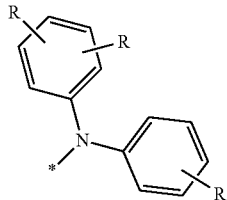

[Substituent3]

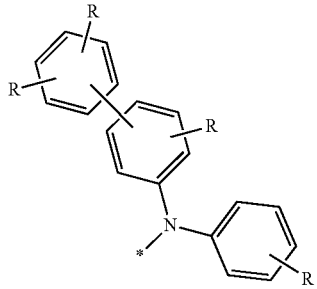

[Substituent4]

[Substituent5]
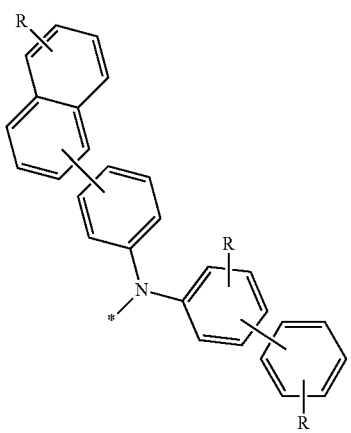
(Substituent6)
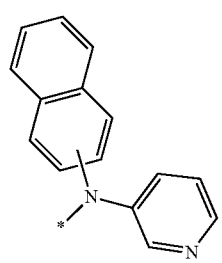
[Substituent7]
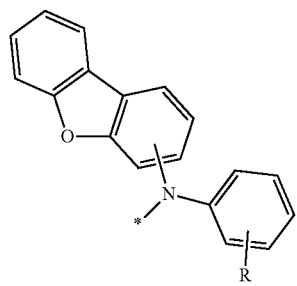
[Substituent8]
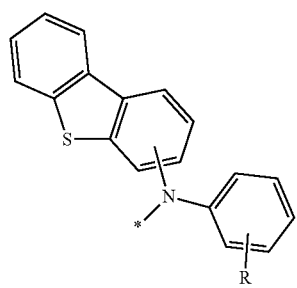
[Substituent9]
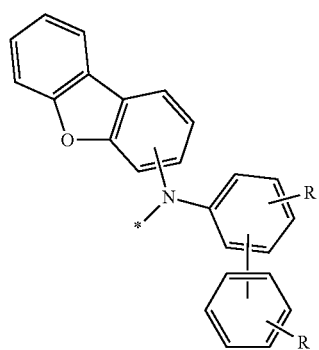
[Substituent10]
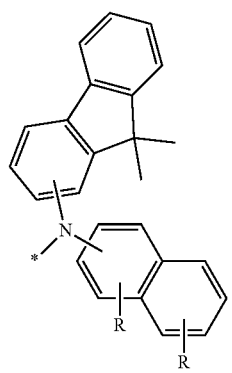
[Substituent11]
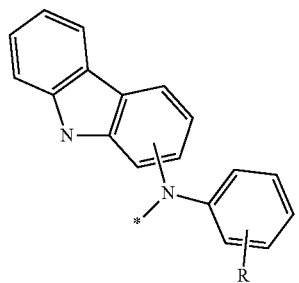
[Substituent12]
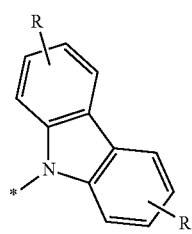
[Substituent13]
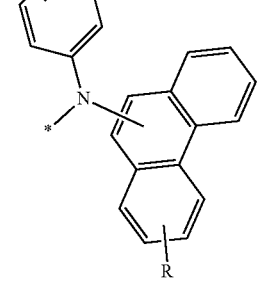
[Substituent14]
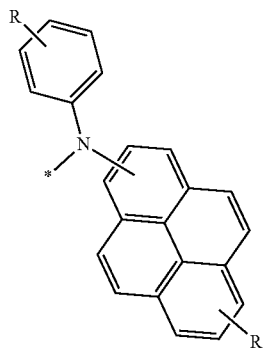

[Substituent15]
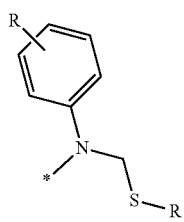
[Substituent16]
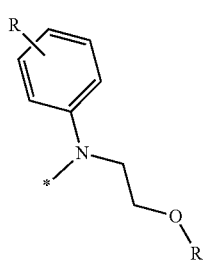
[Substituent17]
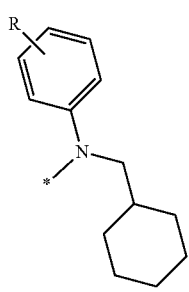
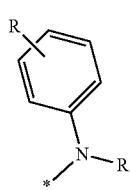
[Substituent18]
[Substituent19]
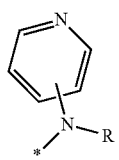
[Substituent20]
[Substituent21]
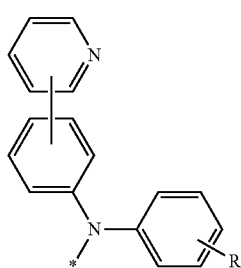
[Substituent22]
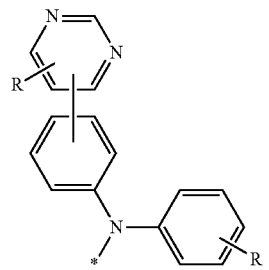
[Substituent23]
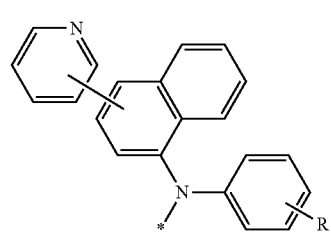
[Substituent24]
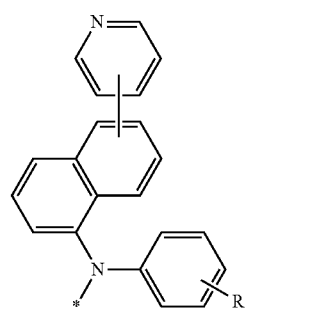
[Substituent25]
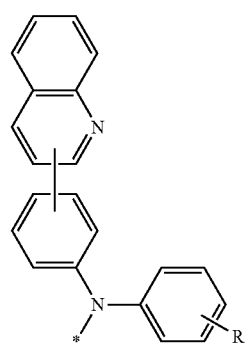
[Substituent26]
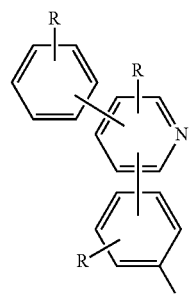

103
-continued
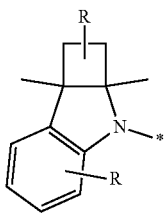
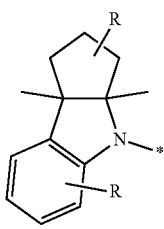
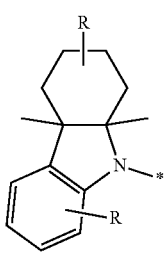
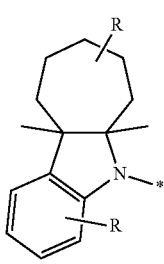
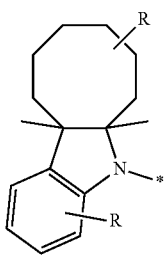
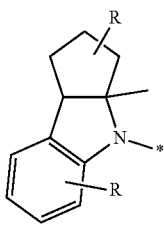
104
-continued
[Substituent27]
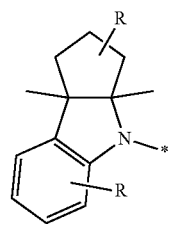
[Substituent28]
[Substituent29]
[Substituent30]
[Substituent31]
[Substituent32]
[Substituent33]
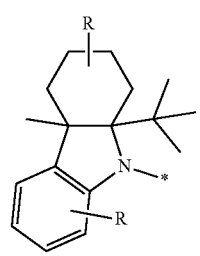
[Substituent34]
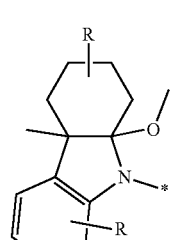
[Substituent35]
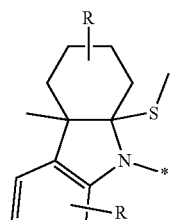
[Substituent36]
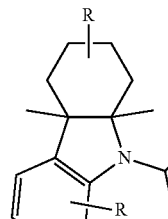
[Substituent37]
[Substituent38]
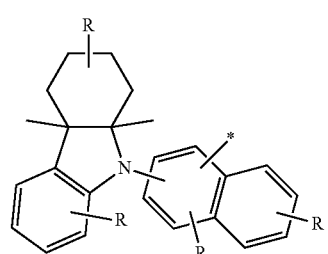

-continued
[Substituent39]
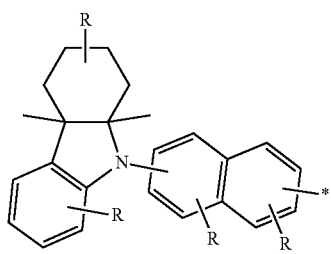
[Substituent44]
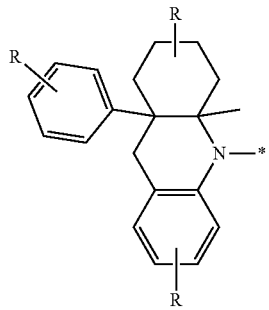
[Substituent40]
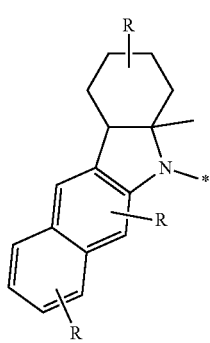
[Substituent45]
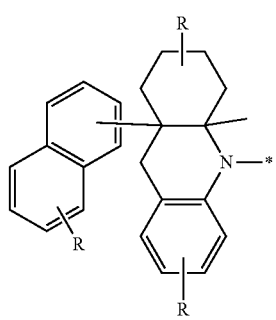
[Substituent41]
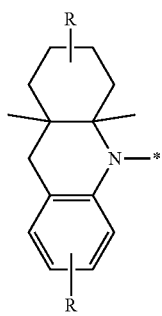
[Substituent46]
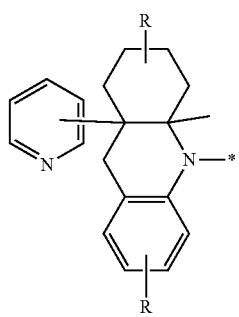
[Substituent42]
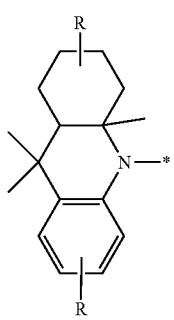
[Substituent47]
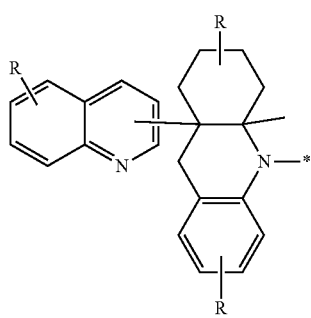
[Substituent43]
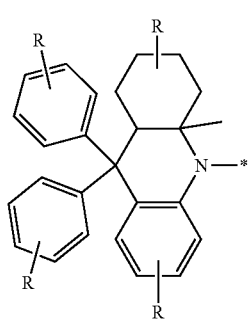
[Substituent48]
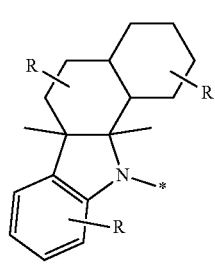

107
-continued

[Substituent49]

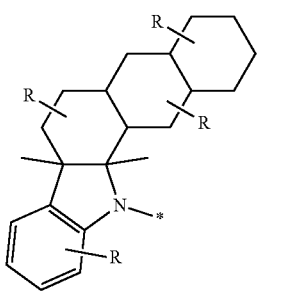

[Substituent50]

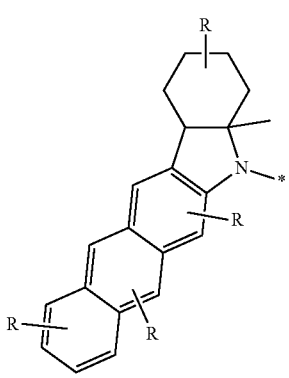

[Substituent51]

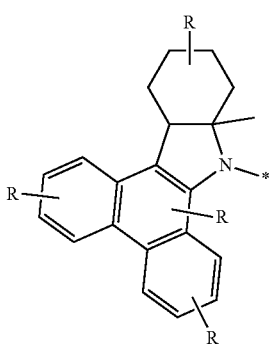

108
-continued

[Substituent52]

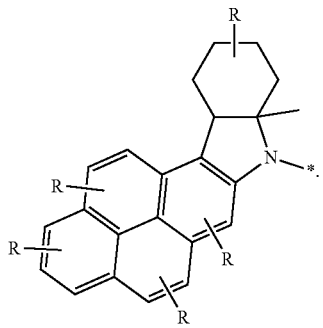

wherein, R's, which may be the same or different, are each independently selected from a hydrogen atom, a deuterium atom, a halogen atom, a hydroxyl, a cyano, a nitro, an amino, an amidino, a hydrazine, a hydrazone, a carboxyl or a salt thereof, a sulfonic acid or a salt thereof, a phosphoric acid or a salt thereof, a substituted or unsubstituted alkyl of 1 to 60 carbon atoms, a substituted or unsubstituted alkenyl of 2 to 60 carbon atoms, a substituted or unsubstituted alkynyl of 2 to 60 carbon atoms, a substituted or unsubstituted alkoxy of 1 to 60 carbon atoms, a substituted or unsubstituted alkylthio of 1 to 60 carbon atoms(alkylthio), a substituted or unsubstituted cycloalkyl of 3 to 60 carbon atoms, a substituted or unsubstituted aryl of 6 to 60 carbon atoms, a substituted or unsubstituted aryloxy of 5 to 60 carbon atoms, a substituted or unsubstituted arylthio of 5 to 60 carbon atoms, a substituted or unsubstituted heteroaryl of 2 to 60 carbon atoms, a substituted or unsubstituted (alkyl)amino of 1 to 60 carbon atoms, a di (substituted or unsubstituted alkyl of 1 to 60 carbon atoms)amino or a (substituted or unsubstituted aryl of 6 to 60 carbon atoms)amino, a di(substituted or unsubstituted aryl of 6 to 60 carbon atoms) amino, a substituted or unsubstituted alkylsilyl of 1 to 40 carbon atoms, a substituted or unsubstituted arylsilyl of 6 to 30 carbon atoms, a germanium, a phosphorus, and a boron, and may amount to 1 to 12 in each substituent and may form a fused ring with an adjacent substituent;

[Chemical Formula 5]

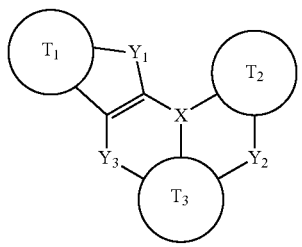

-continued

[Chemical Formula 6]

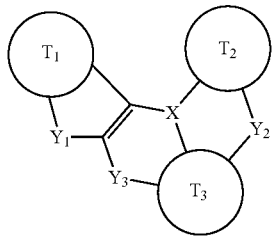

wherein,
X is any one selected from B, P, and P=O,
$T_1$ to $T_3$, which may be the same or different, are each independently a substituted or unsubstituted aromatic hydrocarbon ring of 6 to 50 carbon atoms, or a substituted or unsubstituted heteroaromatic ring of 2 to 50 carbon atoms, and
$Y_1$ to $Y_3$, which may be the same or different, are each independently any one selected from N—$R_{21}$, $CR_{22}R_{23}$, O, S, Se, and $SiR_{24}R_{25}$,
wherein $R_{21}$ to $R_{25}$, which may be same or different, are each independently any one selected from a hydrogen atom, a deuterium atom, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a nitro, a cyano, and a halogen,
at least one of $R_{21}$ to $R_{25}$ may be connected to at least one of $T_1$ to $T_3$ to form an additional mono- or polycyclic aliphatic or aromatic ring, and
$R_{22}$ may be connected to $R_{23}$ to form an additional mono- or polycyclic aliphatic or aromatic ring, and $R_{24}$ may be connected to $R_{25}$ to form an additional mono- or polycyclic aliphatic or aromatic ring.

After being deposited on the light-emitting layer by deposition in a vacuum and spin coating, the electron transport layer 60 is covered with the electron injection layer 70. A cathode metal is deposited on the electron injection layer 70 by thermal vacuum deposition to form the cathode 80, thus obtaining an organic light-emitting diode.

A material for use in the electron transport layer functions to stably carry the electrons injected from the electron injection electrode (cathode), and may be an electron transport material known in the art. Examples of the electron transport material known in the art include quinoline derivatives, particularly, tris(8-quinolinorate)aluminum ($Alq_3$), Liq, TAZ, BAlq, beryllium bis(benzoquinolin-10-olate) ($Bebq_2$), AND, Compound 201, Compound 202, BCP, and oxadiazole derivatives such as PBD, BMD, and BND, but are not limited thereto:

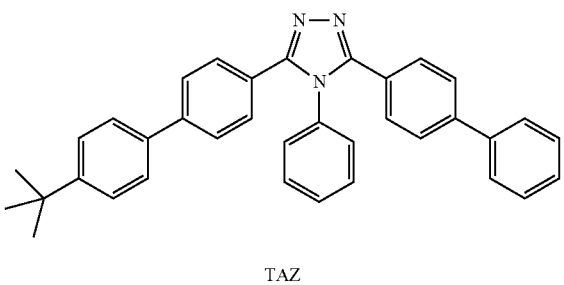

TAZ

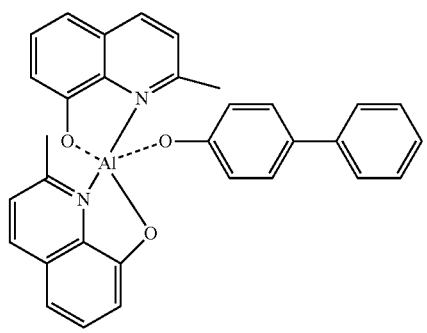

BAlq

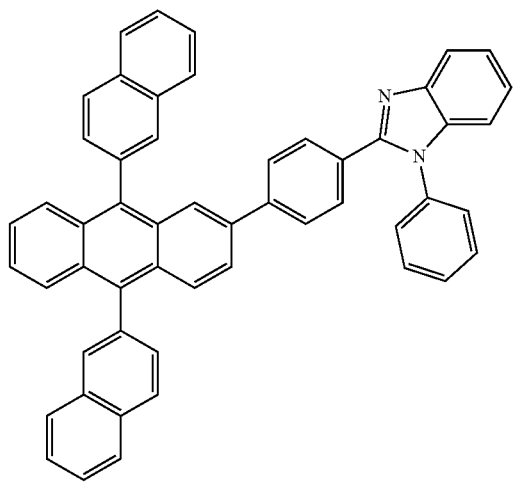

<Compound 201>

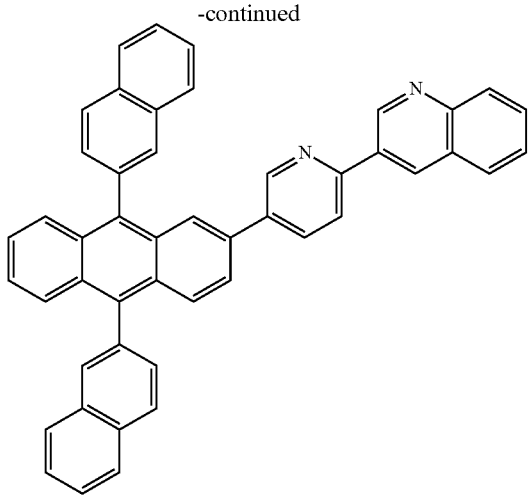

<Compound 202>

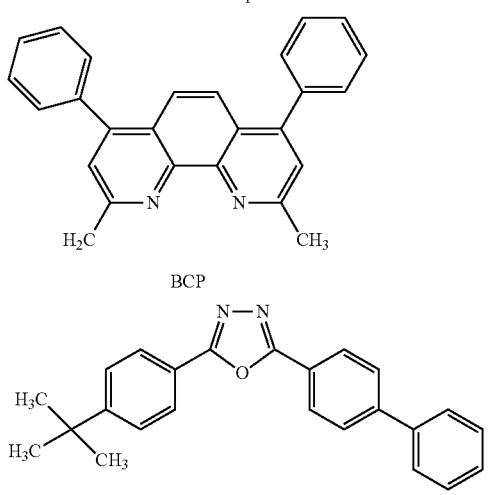

BCP

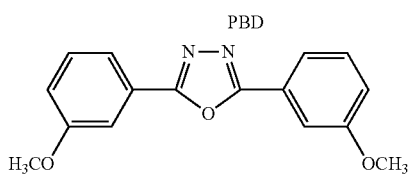

PBD

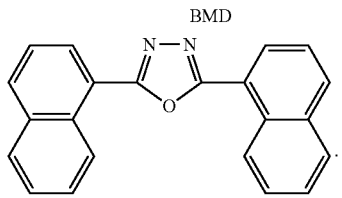

BMD

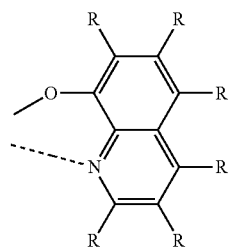

BND

In addition, the organic metal compound represented by Chemical Formula F may be used, either alone or in combination with the aforementioned electron transport layer material in the present disclosure:

$$Y_m\text{-M-}(OA)_n \qquad \text{[Chemical Formula F]}$$

wherein,

Y is a ligand that contains two moieties respectively responsible for forming a single bond through a direct bond to M and for forming a coordinate bond with M, each moiety being selected from among C, N, O and S, and which is chelated by the single bond and the coordinate bond;

M is an alkali metal, an alkaline earth metal, an aluminum (Al) atom, or a boron (B) atom, with a proviso that:

when M is an alkali metal, m=1 and n=0;

when M is an alkaline earth metal, m=1 and n=1, or m=2 and n=0; or when M is aluminum or a boron, m is an integer of 1 to 3 and n is an integer of 0 to 2, satisfying the relationship m+n=3; and OA is a monodentate ligand capable of forming a single bond or a coordinate bond with M, O is oxygen, and A is any one selected from a substituted or unsubstituted alkyl of 1 to 30 carbon atoms, a substituted or unsubstituted aryl of 5 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, and a substituted or unsubstituted heteroaryl of 2 to 50 carbon atoms bearing at least one of O, N, S, and Si as a heteroatom, wherein the term 'substituted' in the expression "a substituted or unsubstituted" means having at least one substituent selected from the group consisting of a deuterium atom, a cyano, a halogen, a hydroxy, a nitro, an alkyl, an alkoxy, an alkylamino, an arylamino, a heteroarylamino, an alkylsilyl, an arylsilyl, an aryloxy, an aryl, a heteroaryl, a germanium, a phosphorus, and a boron.

In the present disclosure, Y's, are each one selected from among, but not limited to, the following [Structural Formula C1] to [Structural Formula C39]:

[Structural Formula C1]

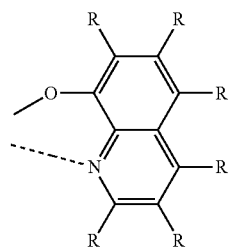

[Structural Formula C2]

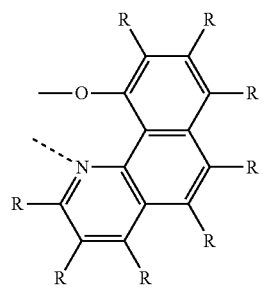

[Structural Formula C3]
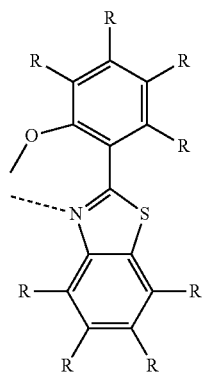
[Structural Formula C4]
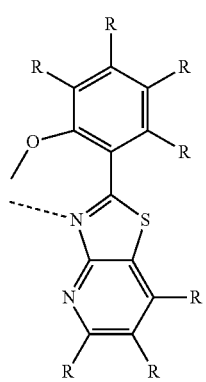
[Structural Formula C5]
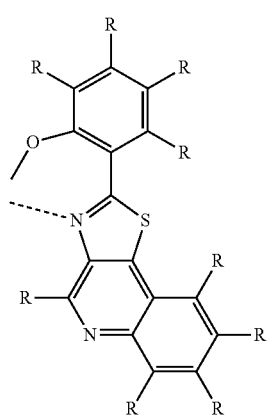
[Structural Formula C6]
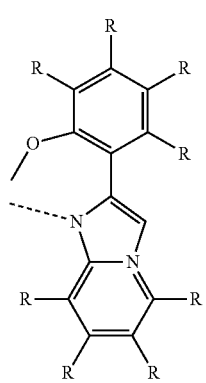
[Structural Formula C7]
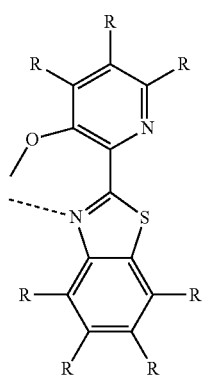
[Structural Formula C8]
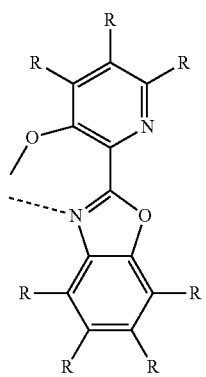
[Structural Formula C9]
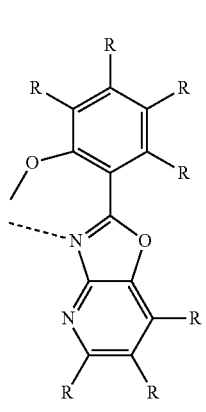
[Structural Formula C10]
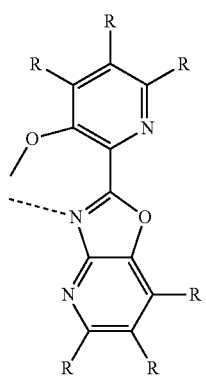

[Structural Formula C11]
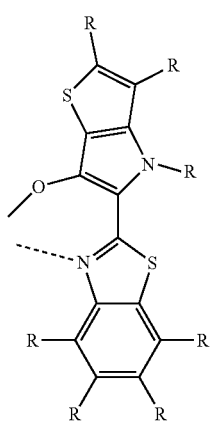
[Structural Formula C12]
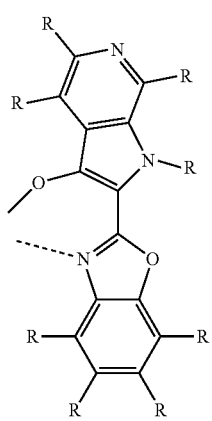
[Structural Formula C13]
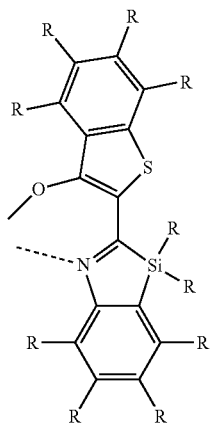
[Structural Formula C14]
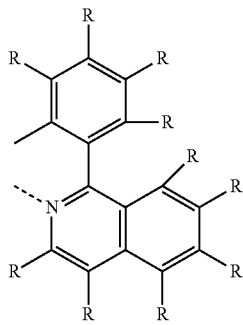
[Structural Formula C15]
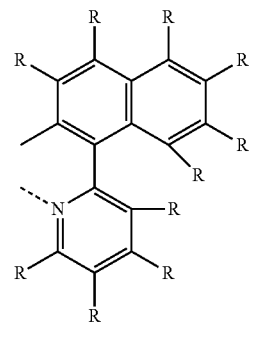
[Structural Formula C16]
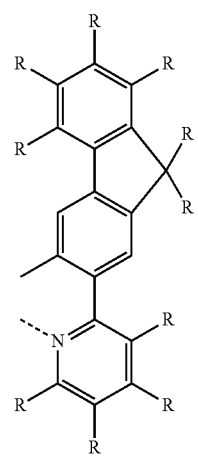
[Structural Formula C17]
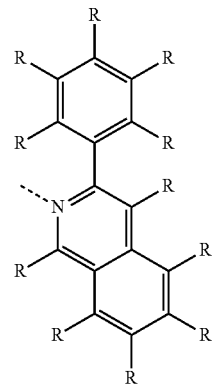
[Structural Formula C18]
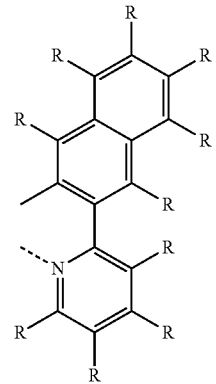

[Structural Formula C19]
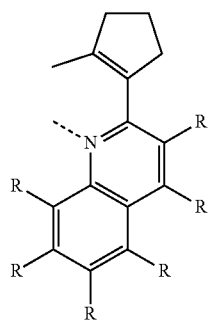
[Structural Formula C20]
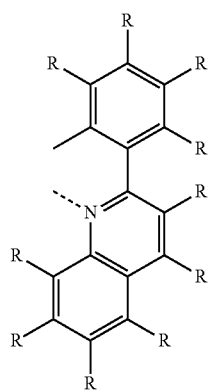
[Structural Formula C21]
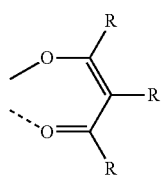
[Structural Formula C22]
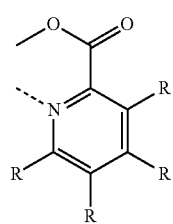
[Structuaral Formula C23]
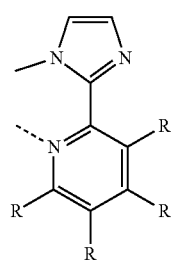
[Structural Formula C24]
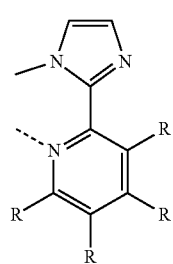
[Structural Formula C25]
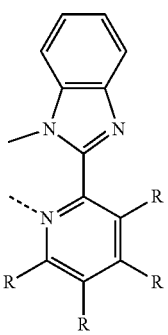
[Structural Formula C26]
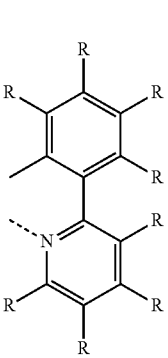
[Structural Formula C27]
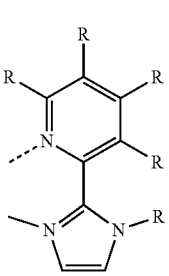
[Structural Formula C28]
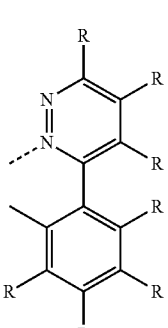
[Structural Formula C29]
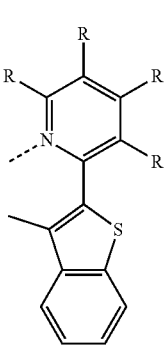

-continued

[Structural Formula C30]

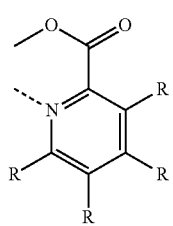

[Structural Formula C31]

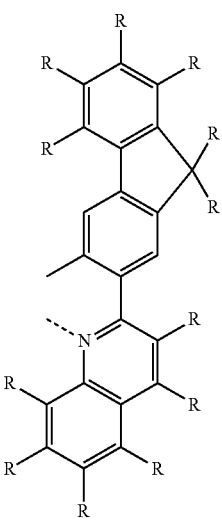

[Structural Formula C32]

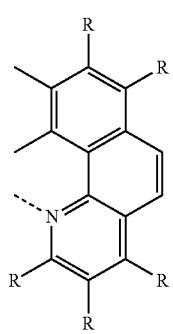

[Structural Formula C33]

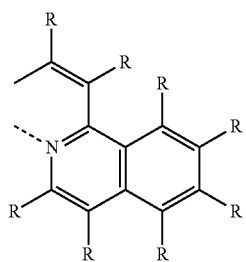

[Structural Formula C34]

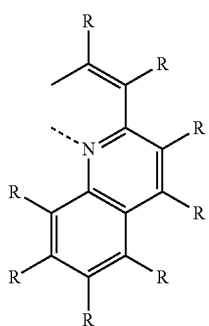

-continued

[Structural Formula C35]

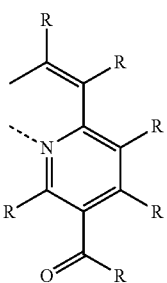

[Structural Formula C36]

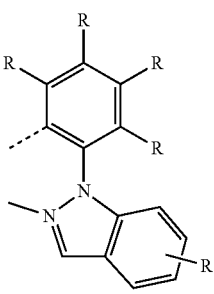

[Structural Formula C37]

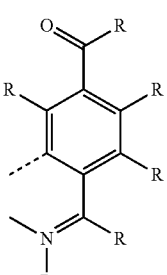

[Structural Formula C38]

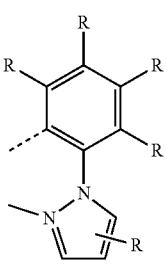

[Structural Formula C39]

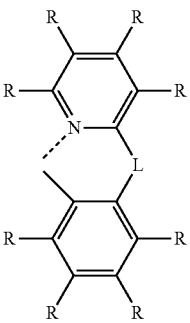

wherein,

R's, which may be the same or different, are each independently selected from a hydrogen atom, a deuterium atom, a halogen, a cyano, a substituted or unsubstituted alkyl of 1 to 30 carbon atoms, a substituted or unsubstituted aryl of 6 to 30 carbon atoms, a substituted or unsubstituted heteroaryl of 3 to 30 carbon atoms, a substituted or unsubstituted alkoxy of 1 to 30 carbon atoms, a substituted or unsubstituted cycloalkyl of 3 to 30 carbon atoms, a substituted or unsubstituted alkenyl of 2 to 30 carbon atoms, a substituted or unsubstituted alkylamino of 1 to 30 carbon atoms, a substituted or unsubstituted alkylsilyl of 1 to 30 carbon atoms, a substituted or unsubstituted arylamino of 6 to 30 carbon atoms, and a substituted or unsubstituted arylsilyl of 6 to 30 carbon atoms, and may form a spiro or fused ring with an adjacent substituent via an alkylene or alkenylene linker.

In the organic light emitting diode of the present disclosure, an electron injection layer (EIL) that functions to facilitate electron injection from the cathode may be deposited on the electron transport layer. The material for the EIL is not particularly limited.

So long as it is conventionally used in the art, any material can be available for the electron injection layer without particular limitations. Examples include CsF, NaF, LiF, NaCl, $Li_2O$, and BaO. Deposition conditions for the electron injection layer may vary, depending on compounds used, but may be generally selected from condition scopes that are almost the same as for the formation of hole injection layers.

The electron injection layer may range in thickness from about 1 Å to about 100 Å, and particularly from about 3 Å to about 90 Å. Given the thickness range for the electron injection layer, the diode can exhibit satisfactory electron injection properties without actually elevating a driving voltage.

Here, the cathode may be made of lithium (Li), magnesium (Mg), aluminum (Al), aluminum-lithium (Al—Li), calcium (Ca), magnesium-indium (Mg—In), or magnesium-silver (Mg—Ag). For a top-emitting OLED, a transparent cathode made of ITO or IZO may be employed.

In another embodiment, the light-emitting diode of the present disclosure may further comprise a light-emitting layer, made of a blue light-emitting material, a green light-emitting material, or a red light-emitting material, which can emit light in a wavelength range of 380 nm to 800 nm. That is, the light-emitting layer in the organic light-emitting device of the present disclosure may have a multilayer structure in which the additional blue, green, and/or red light-emitting layer may be made of a fluorescent or phosphorescent material.

Further, one or more layers selected from among a hole injection layer, a hole transport layer, a light emitting layer, an electron transport layer, and an electron injection layer may be deposited using a single-molecule deposition process or a solution process.

Here, the deposition process is a process by which a material is vaporized in a vacuum or at a low pressure and deposited to form a layer, and the solution process is a method in which a material is dissolved in a solvent and applied for the formation of a thin film by means of inkjet printing, roll-to-roll coating, screen printing, spray coating, dip coating, spin coating, etc.

Also, the organic light-emitting diode of the present disclosure may be applied to a device selected from among flat display devices, flexible display devices, monochrome or grayscale flat illumination devices, and monochrome or grayscale flexible illumination devices.

A better understanding of the present disclosure may be obtained through the following examples which are set forth to illustrate, but are not to be construed as limiting the present invention.

EXAMPLE

Synthesis Example 1: Synthesis of Compound 1

Synthesis Example 1-(1): Synthesis of Intermediate 1-a

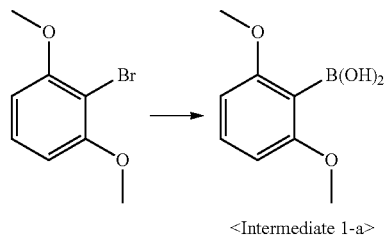

<Intermediate 1-a>

In a 1 L round-bottom flask, a solution of 2-bromo-1,3-dimethoxybenzene (50 g, 230 mmol) in tetrahydrofuran (400 ml) was chilled to −78° C. under a nitrogen atmosphere and added with drops of n-butyl lithium (167 ml, 280 mmol). The solution was stirred for 2 hours at the same temperature, mixed with trimethyl borate (36 ml, 320 mmol), and then stirred again at room temperature overnight. After completion of the reaction, drops of 2N—HCl were slowly added for acidification. Extraction was conducted with water and ethyl acetate, and the organic layer thus formed was separated and dried over magnesium sulfate. The residue was concentrated at a reduced pressure and recrystallized in heptane and toluene to afford Intermediate 1-a (20.8 g, 50%)

Synthesis Example 1-(2): Synthesis of Intermediate 1-b

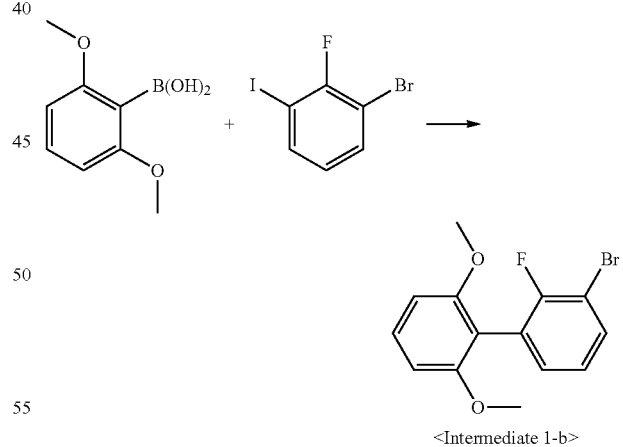

<Intermediate 1-b>

In a 500-ml reactor, Intermediate 1-a (20.8 g, 110 mmol), 1-bromo-2-fluoro-3-iodobenzene (28.7 g, 95 mmol), tetrakis(triphenylphosphine)palladium (33 g, 29 mmol), and sodium carbonate (30.3 g, 290 mmol) were put, followed by toluene (200 ml), ethanol (60 ml), and water (60 ml). The reactor was heated to 80° C. before solution was stirred for 12 hours. After completion of the reaction, the temperature of the reactor was lowered to room temperature and the reaction mixture was extracted with ethyl acetate. The organic layer thus formed was isolated by column chromatography afforded Intermediate 1-b (22.3 g, 63%)

Synthesis Example 1-(3): Synthesis of Intermediate 1-c

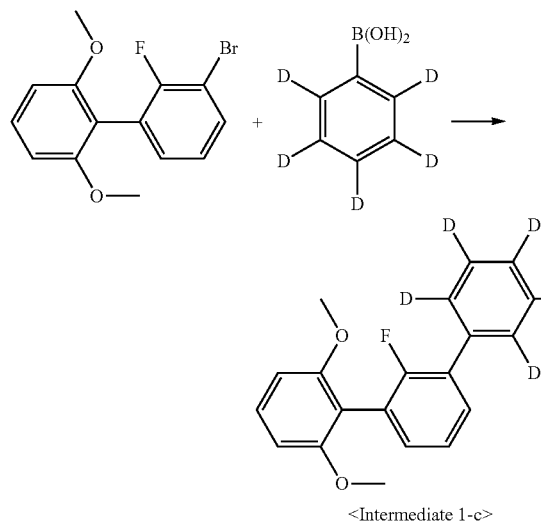

<Intermediate 1-c>

The same procedure as in Synthesis Example 1-(2) was carried out, with the exception of using phenyl-d5-boronic acid and Intermediate 1-b instead of and Intermediate 1-(a) and 1-bromo-2-fluoro-3-iodobenzene, respectively, to afford Intermediate 1-c. (yield 72%).

Synthesis Example 1-(4): Synthesis of Intermediate 1-d

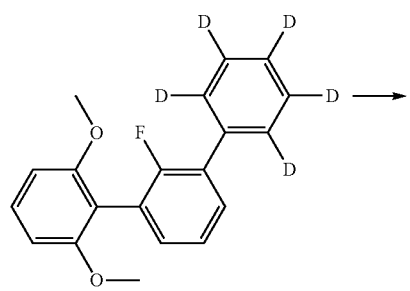

<Intermediate 1-d>

In a 500-ml round-bottom flask, Intermediate 1-c (16.6 g, 53 mmol), hydrogen bromic acid (48 ml, 260 mmol), and acetic acid (100 ml) were stirred together for 12 hours. After completion of the reaction, the reaction mixture was cooled to room temperature and stirred while water was added thereto. The reaction mixture was subjected to extraction with water and ethyl acetate. The organic layer thus formed was separated, concentrated in a vacuum, and recrystallized in heptane. Filtration and drying afforded Intermediate 1-d (17.6 g, 95%).

Synthesis Example 1-(5): Synthesis of Intermediate 1-e

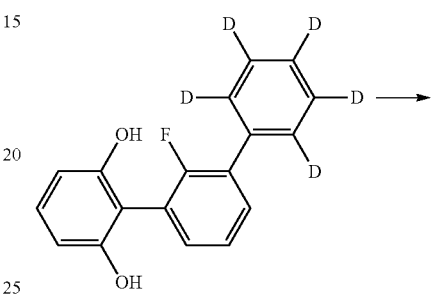

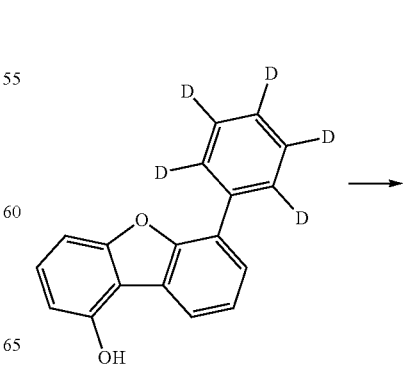

<Intermediate 1-e>

In a 500-ml round-bottom flask, Intermediate 1-d (14.3 g, 50 mmol), potassium carbonate (20.7 g, 150 mmol), and N-methyl-2-pyrrolidone (112 ml) were stirred together for 12 hours. After completion of the reaction, extraction was made and the organic layer thus formed was isolated. Concentration in a vacuum and recrystallization in heptane afforded Intermediate 1-e (10.6 g, 80%).

Synthesis Example 1-(6): Synthesis of Intermediate 1-f

125

-continued

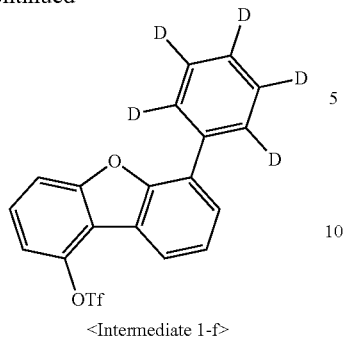

<Intermediate 1-f>

In a 500-ml round-bottom flask, Intermediate 1-e (10.6 g, 40 mmol) was put under a nitrogen atmosphere, followed by adding dichloromethane (136 ml) to dissolve the intermediate. The solution was chilled to 0° C., and pyridine (10 ml, 110 mmol) and trifluoromethanesulfonyl anhydride (12.7 g, 68 mmol) were dropwise added thereto. The solution was stirred at room temperature for 12 hours and then together with water (20 ml). After extraction with water and dichloromethane, the organic layer was isolated and recrystallized in heptane to afford Intermediate 1-f (7.5 g, 47%).

Synthesis Example 1-(7): Synthesis of Compound 1

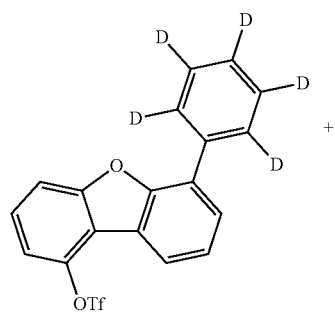

+

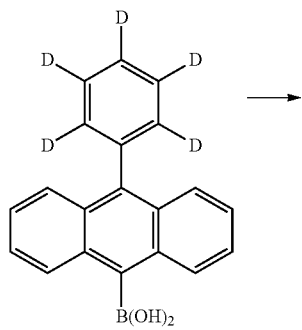

126

-continued

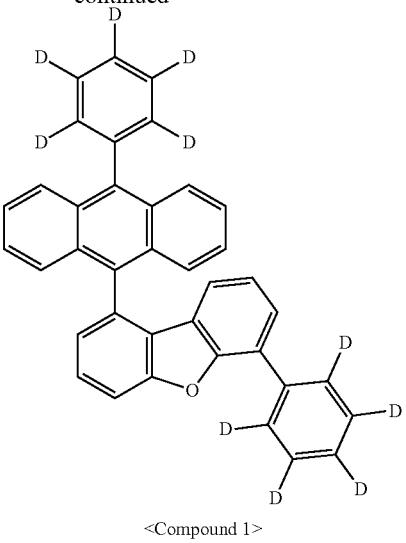

<Compound 1>

In a 250-ml round-bottom flask, Intermediate 1-f (7.5 g, 19 mmol), 10-phenyl(d5)-anthracene-9-boronic acid (7 g, 23 mmol), tetrakis(triphenylphosphine)palladium (0.66 g, 0.6 mmol), and potassium carbonate (7.9 g, 57 mmol) were put, followed by toluene (53 ml), ethanol (23 ml), and water (23 ml). The solution was heated to 80° C. and stirred for 12 hours under reflux. After completion of the reaction, the reaction mixture was cooled to room temperature and added with methanol before stirring. The organic layer thus formed was isolated, concentrated in a vacuum, and recrystallized in acetone to afford Compound 1 (6.2 g, 65%).

MS (MALDI-TOF): m/z 506.25 [M$^+$]

Synthesis Example 2: Synthesis of Compound 10

Synthesis Example 2-(1): Synthesis of Compound 10

The same procedure as in Synthesis Example 1-(1) was carried out, with the exception of using 2-bromo-1,4-dimethoxybenzene instead of 2-bromo-1,3-dimethoxybenzene, to afford Compound 10. (yield 45%)

MS (MALDI-TOF): m/z 506.25 [M$^+$]

Synthesis Example 3: Synthesis of Compound 21

Synthesis Example 3-(1): Synthesis of Intermediate 3-a

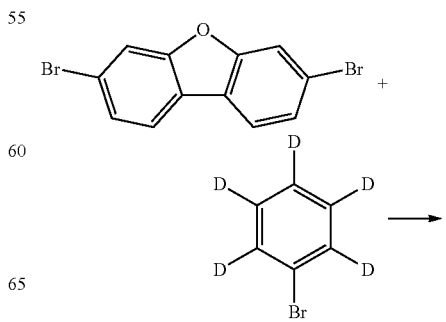

-continued

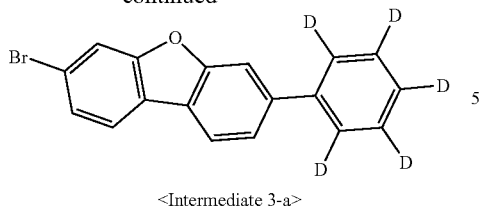

<Intermediate 3-a>

In a 2-L round-bottom flask, phenyl-d5-boronic acid (13 g, 0.08 mol) and 3,6-dibromobenzofuran (32.6 g, 0.1 mol) were dissolved in toluene (700 mL) and ethanol (150 mL). An aqueous potassium carbonate solution (150 mL) and tetrakis(triphenyl phosphine)palladium (2.3 g, 0.002 mol) were added to the reactor which was then heated to 110° C., and stirred for 12 hours. The reaction mixture was absorbed to active carbon and filtered in a vacuum. Recrystallization in toluene and ethanol afforded Intermediate 3-a (23.6 g, 90%).

Synthesis Example 3-(2): Synthesis of Compound 21

The same procedure as in Synthesis Example 1-(7) was carried out, with the exception of using Intermediate 3-a instead of Intermediate 1-f, to afford Compound 21. (yield 75%)

MS (MALDI-TOF): m/z 506.25 [M$^+$]

Dopant Preparation: Synthesis of BD Compound

Synthesis Example 4: Synthesis of BD 1

Synthesis Example 4-(1): Synthesis of Intermediate 4-a

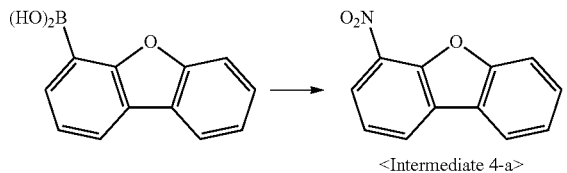 [SMILES: OB(O)c1cccc2c1oc1ccccc12 ; O=[N+]([O-])c1cccc2c1oc1ccccc12]

<Intermediate 4-a>

In a 2-L round-bottom flask reactor, 4-dibenzofuran boronic acid (85.0 g, 0.401 mol), bismuth (III) nitrate pentahydrate (99.2 g, 0.200 mol), and toluene (400 ml) were stirred together at 70° C. for 3 hours in a nitrogen atmosphere. After completion of the reaction, the reaction mixture was cooled to room temperature and the solid thus formed was filtered and washed with toluene to afford Intermediate 4-a (61.5 g, 72%).

Synthesis Example 4-(2): Synthesis of Intermediate 4-b

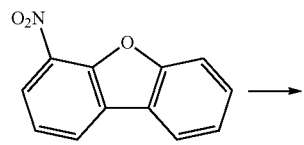

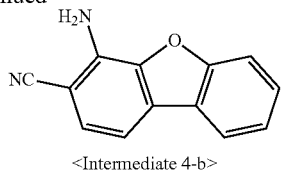

<Intermediate 4-b>

In a 2-L round-bottom flask reactor, ethyl cyanoacetate (202.9 g, 1.794 mol) and dimethyl formamide (500 ml) were placed. Potassium hydroxide (67.10 g, 1.196 mol) and potassium cyanide (38.95 g, 0.598 mol) were added, followed by dimethyl formamide (200 ml). The resulting mixture was stirred at room temperature, added with Intermediate 4-a (127.5 g, 0.737 mol) little by little, and then stirred at 50° C. for 72 hours. After completion of the reaction, an aqueous sodium hydroxide solution (25%, 200 ml) was added and stirred for 3 hours under reflux. After cooling to room temperature, extraction with ethyl acetate and water was conducted. The organic layer thus formed was separated, and concentrated in a vacuum. Purification by column chromatography afforded Intermediate 4-b (20.0 g, 16%).

Synthesis Example 4-(3): Synthesis of Intermediate 4-c

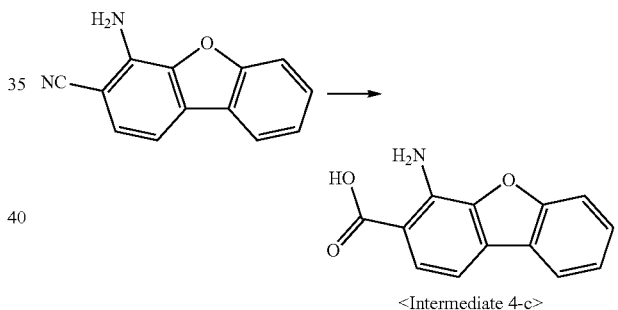

<Intermediate 4-c>

In a 2-L round-bottom flask reactor, a mixture of Intermediate 4-b (20.0 g, 0.096 mol), ethanol (600 ml), and an aqueous potassium hydroxide solution (170 ml, 142.26 g, 2.53 mol) was stirred for 12 hours under reflux. After completion of the reaction mixture was cooled to room temperature, and then acidified with 6 N HCl (400 ml). Stirring for 20 min was followed by filtration. The solid thus obtained was washed with ethanol to afford Intermediate 4-c (17.0 g, 88.5%).

Synthesis Example 4-(4): Synthesis of Intermediate 4-d

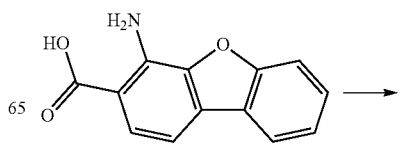

-continued

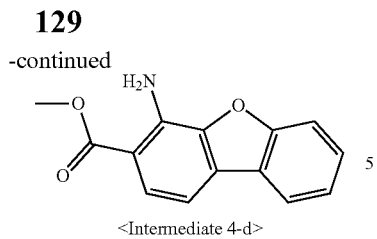

<Intermediate 4-d>

In a 2-L round-bottom flask reactor, a mixture of Intermediate 4-c (17.0 g, 75 mmol) and sulfuric acid (15 ml) was stirred for 72 hours under reflux. After completion of the reaction, the reaction mixture was extracted with ethyl acetate and water. The organic layer was separated and washed with an aqueous sodium hydrogen carbonate solution. An excess of methanol was added during the vacuum concentration of the organic layer, followed by filtration to afford Intermediate 4-d (14.0 g, 77.6%).

Synthesis Example 4-(5): Synthesis of Intermediate 4-e

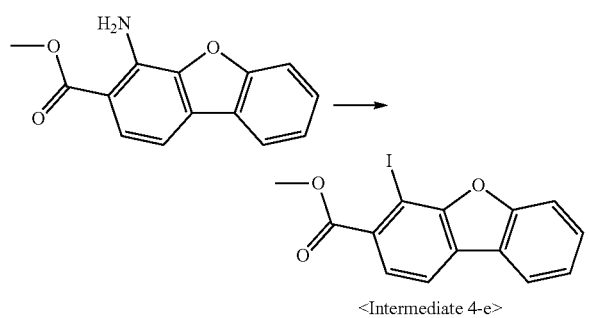

<Intermediate 4-e>

In a 1-L round-bottom flask, a mixture of Intermediate 4-d (32.6 g, 0.135 mol), HCl (30 ml), and water (150 ml) was cooled to 0° C. and stirred for 1 hour. At the same temperature, an aqueous solution (75 ml) of sodium nitrite (11.2 g, 0.162 mol) was added and then stirred for 1 hour. An aqueous solution (75 ml) of potassium iodide (44.8 g, 0.270 mol) was dropwise added, taking care not to increase the temperature of the reaction solution above 5° C. Stirring was continued for 5 hours at room temperature, and after completion of the reaction, the reaction mixture was washed with an aqueous sodium thiosulfate solution and extracted with ethyl acetate and water. The organic layer was separated and concentrated in a vacuum. Purification through column chromatography afforded Intermediate 4-e (22.8 g, 48%).

Synthesis Example 4-(6): Synthesis of Intermediate 4-f

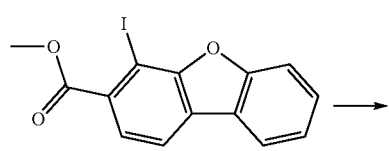

-continued

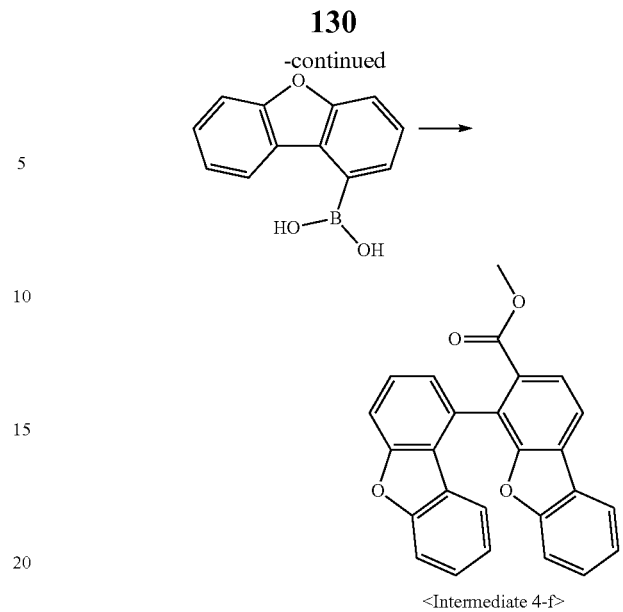

<Intermediate 4-f>

In a 500-mL round-bottom flask, Intermediate 4-e (25.7 g, 73 mmol), 1-dibenzofuran boronic acid (18.7 g, 88 mmol), tetrakis(triphenylphosphine)palladium (1.7 g, 0.15 mmol), and potassium carbonate (20.2 g, 146.7 mmol) were stirred together with toluene (125 mL), tetrahydrofuran (125 mL), and water (50 mL) for 10 hours at 80° C. After completion of the reaction, the reaction mixture was cooled to room temperature and extracted with ethyl acetate. The organic layer thus formed was separated, concentrated in a vacuum, and purified by column chromatography to afford Intermediate 4-f. (14.9 g, 52%)

Synthesis Example 4-(7): Synthesis of Intermediate 4-g

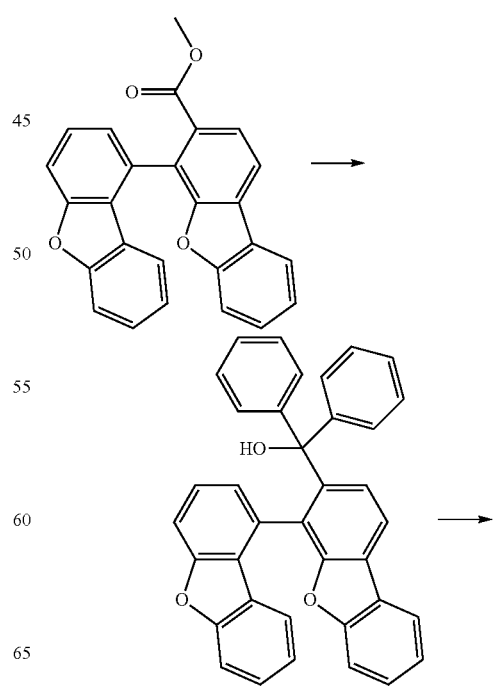

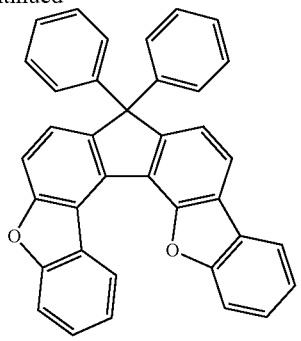

<Intermediate 4-g>

In a 500-mL round-bottom flask, bromobenzene (25.5 g, 0.163 mol) and tetrahydrofuran (170 ml) were placed and chilled to −78° C. under a nitrogen atmosphere. To the chilled reaction solution was dropwise added butyl lithium (1.6 M, 95.6 ml, 0.153 mol). At the same temperature, the solution was stirred for 1 hour and added with Intermediate 4-f (20.0 g, 0.051 mol), followed by stirring for 3 hours at room temperature. After completion of the reaction, water (50 ml) was added and stirred for 30 min. After extraction with ethyl acetate and water, the organic layer thus formed was separated and concentrated in a vacuum. The concentrate was added with acetic acid (200 ml) and HCl (1 ml) and stirred at 80° C. After completion of the reaction, washing with methanol afforded Intermediate 4-g (20.0 g, 78%).

Synthesis Example 4-(8): Synthesis of Intermediate 4-h

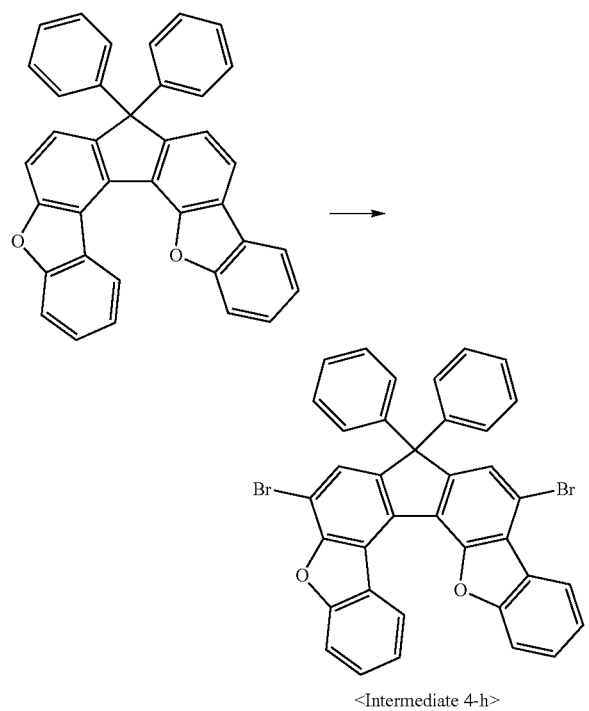

<Intermediate 4-h>

In a 1-L round-bottom flask reactor, Intermediate 4-g (16.5 g, 33 mmol) and dichloromethane (300 ml) were stirred together at room temperature. A dilution of bromine (3.4 ml, 66 mmol) in dichloromethane (50 ml) was dropwise added, followed by stirring at room temperature for 8 hours. After completion of the reaction, the reaction mixture was stirred together with acetone (100 ml). The solid thus formed was filtered and washed with acetone. Recrystallization of the solid in monochlorobenzene afforded Intermediate 4-h. (12.6 g, 58%)

Synthesis Example 4-(9): Synthesis of BD 1

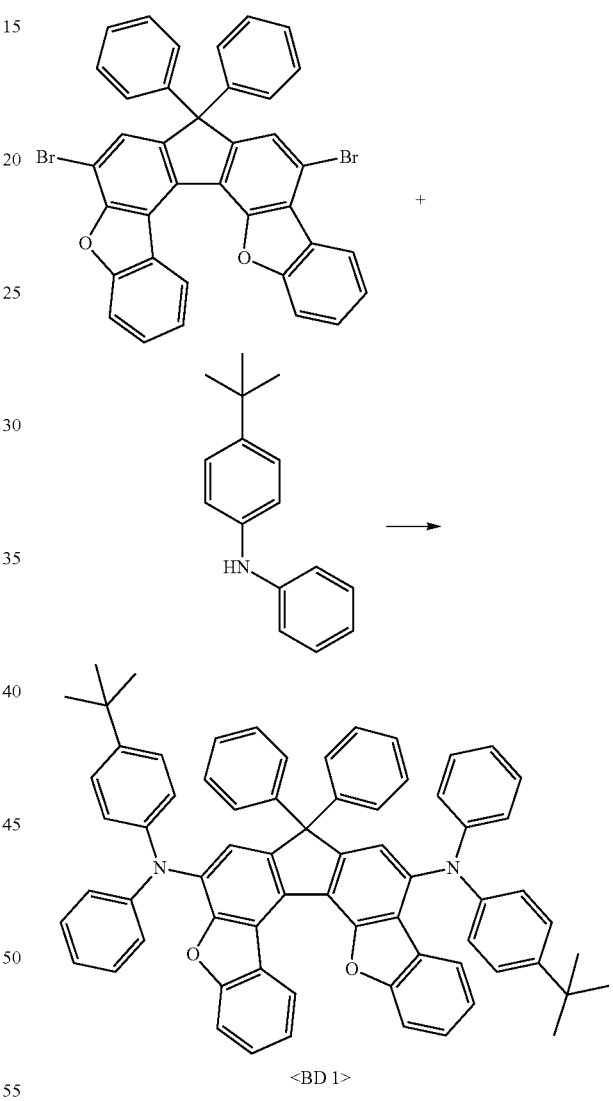

<BD 1>

In a 250-ml round-bottom flask, a mixture of Intermediate 4-h (5.9 g, 0.009 mol), (4-tert-butylphenyl)-phenylamine (4.7 g, 0.021 mol), palladium (II) acetate (0.08 g, 0.4 mmol), sodium tert-butoxide (3.4 g, 0.035 mol), tri-tert-butyl phosphine (0.07 g, 0.4 mmol), and toluene (60 ml) was stirred for 2 hours under reflux. After completion of the reaction, the reaction mixture was cooled to room temperature and then extracted with dichloromethane and water. The organic layer thus formed was separated, dried over magnesium sulfate, and concentrated in a vacuum. The concentrate was purified by column chromatography and recrystallized in dichloromethane and acetone to afford BD 1. (4.9 g, 58%)
MS (MALDI-TOF): m/z 944.43 [M$^+$]

Synthesis Example 5: Synthesis of BD 2

Synthesis Example 5-(1): Synthesis of Intermediate 5-a

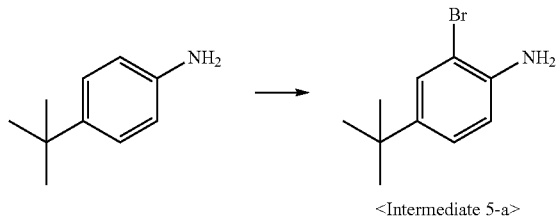

<Intermediate 5-a>

In a 1-L reactor, a solution of 4-tert-butylaniline (40 g, 236 mmol) in methylene chloride (400 mL) was stirred at 0° C. and then slowly added with N-bromosuccinimide (42 g, 236 mmol) before stirring at room temperature for 4 hours. After completion of the reaction, H$_2$O was dropwise added and then the mixture was extracted with methylene chloride. The organic layer thus formed was concentrated and isolated by column chromatography to afford Intermediate 5-a (48 g, yield 80%).

Synthesis Example 5-(2): Synthesis of Intermediate 5-b

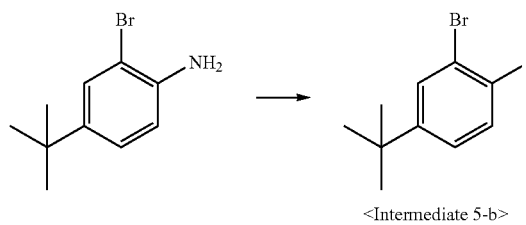

<Intermediate 5-b>

In a 2-L reactor, Intermediate 5-a (80 g, 351 mmol) and water (450 mL) were stirred together, followed by adding sulfuric acid (104 mL). At 0° C., a solution of sodium nitrite (31.5 g, 456 mmol) in water (240 mL) was dropwise added and then stirred for 2 hours. A solution of potassium iodide (116.4 g, 701 mmol) in water (450 mL) was dropwise added at 0° C. and then stirred at room temperature for 6 hours. After completion of the reaction, an aqueous sodium thiosulfate solution was added and stirred at room temperature. The reaction mixture was extracted with ethylacetate and the organic layer thus formed was isolated by column chromatography to afford Intermediate 5-b (58 g, yield 51%).

Synthesis Example 5-(3): Synthesis of Intermediate 5-c

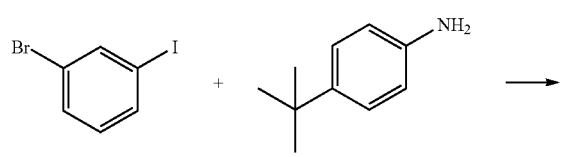

-continued

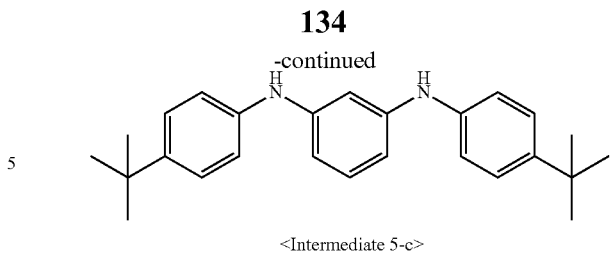

<Intermediate 5-c>

In a 1-L reactor, 1-bromo-5-iodobenzene (50.1 g, 177 mmol), 4-tert-butylaniline (58 g, 389 mmol), palladium acetate (1.6 g, 7 mmol), sodium tert-butoxide (51 g, 530 mmol), bis(diphenylphosphino)-1,1'-binaphthyl (4.4 g, 7 mmol), and toluene (500 mL) were stirred under reflux for 24 hours. After completion of the reaction, separation by filtration, concentration, and column chromatography afforded Intermediate 5-c (52.8 g, yield 80%).

Synthesis Example 5-(4): Synthesis of Intermediate 5-d

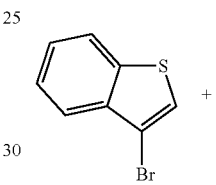

+

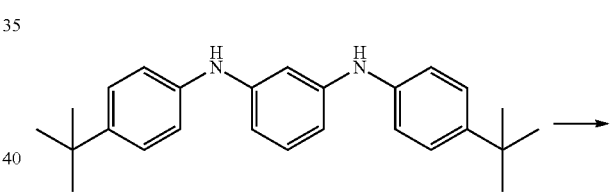

<Intermediate 5-d>

In a 250-mL reactor, Intermediate 5-c (36.5 g, 98 mmol), 3-bromobenzothiophene (20.9 g, 98 mmol), palladium acetate (0.5 g, 2 mmol), sodium tert-butoxide (18.9 g, 196 mmol), tri-tert-butylphosphine (0.8 g, 4 mmol), and toluene (200 mL) were stirred together under reflux for 5 hours. After completion of the reaction, separation by filtration, concentration, and column chromatography afforded Intermediate 5-d (35.6 g, yield 72%).

Synthesis Example 5-(5): Synthesis of Intermediate 5-e

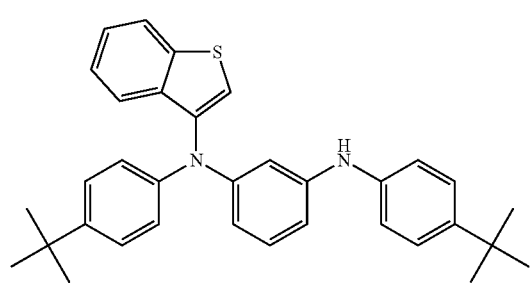

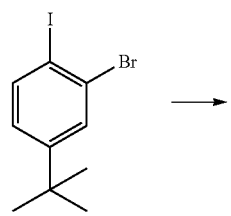

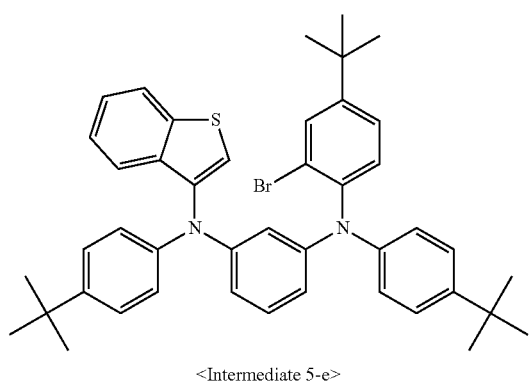

<Intermediate 5-e>

The same procedure as in Synthesis Example 5-(4) was carried out, with the exception of using Intermediate 5-d and 2-bromo-4-tert-butyl-1-iodobenzene instead of Intermediate 5-c and 3-bromobenzothiophene, respectively, to afford Intermediate 5-e. (yield 67%)

Synthesis Example 5-(6): Synthesis of BD 2

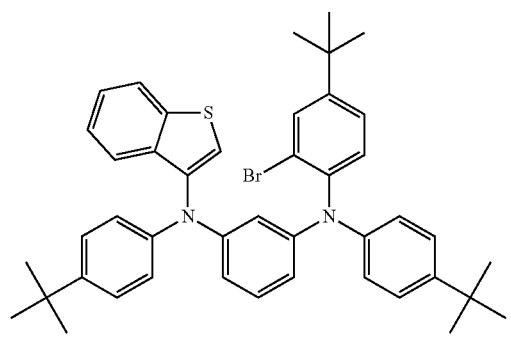

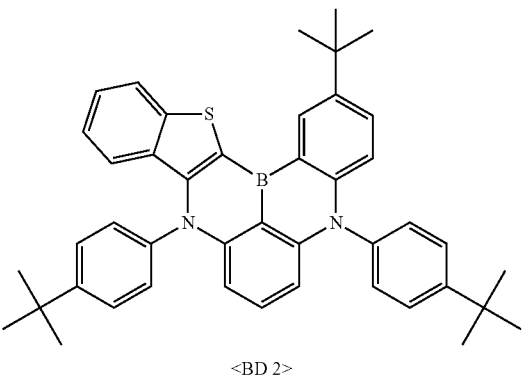

<BD 2>

To a 300-mL reactor were added Intermediate 5-e (16.5 g, 23 mmol) and tert-butyl benzene (120 mL). At −78° C., n-butyl lithium (42.5 mL, 68 mmol) was dropwise added. Then, the mixture was stirred at 60° C. for 3 hours. Subsequently, nitrogen was introduced at the same temperature into the reactor to remove heptane. Boron tribromide (11.3 g, 45 mmol) was dropwise added at −78° C. and then stirred for 1 hour at room temperature. N, N-Diisopropylethylamine (5.9 g, 45 mmol) was added at 0° C. and then stirred at 120° C. for 2 hours. After completion of the reaction, an aqueous sodium acetate solution was added at room temperature and stirred. Extraction was carried out with ethyl acetate. The organic layer was concentrated and separated by column chromatography to afford BD 2 (2.2 g, yield 15%).

MS (MALDI-TOF): m/z 644.34 [M$^+$]

Synthesis Example 6: Synthesis of BD 3

Synthesis Example 6-(1): Synthesis of Intermediate 6-a

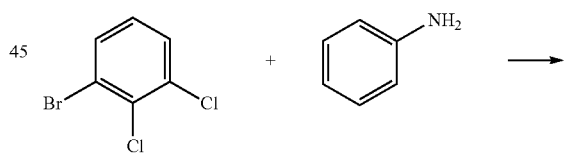

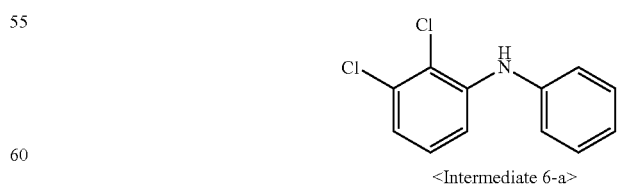

<Intermediate 6-a>

The same procedure as in Synthesis Example 5-(3) was carried out, with the exception of using 1-bromo-2,3-dichlorobenzene instead of 1-bromo-5-iodobenzene, to afford Intermediate 6-a. (yield 71%)

Synthesis Example 6-2: Synthesis of Intermediate 6-b

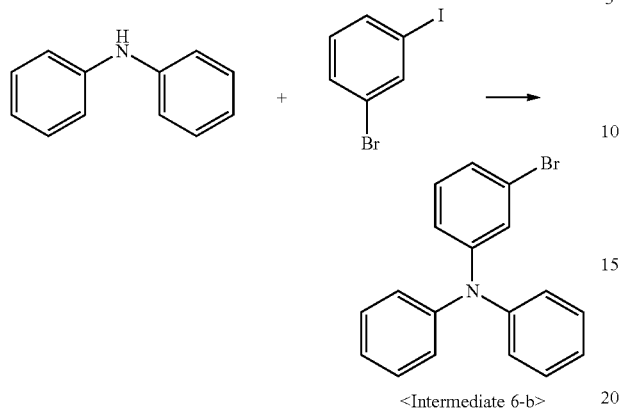

<Intermediate 6-b>

In a 2-L reactor, diphenylamine (60.0 g, 355 mmol), 1-bromo-3-iodobenzene (100.3 g, 355 mmol), palladium acetate (0.8 g, 4 mmol), xantphos (2 g, 4 mmol), sodium tert-butoxide (68.2 g, 709 mmol), and toluene (700 mL) were stirred together under reflux for 2 hours. After completion of the reaction, separation by filtration, concentration, and column chromatography afforded Intermediate 6-b (97 g, yield 91%).

Synthesis Example 6-3: Synthesis of Intermediate 6-c

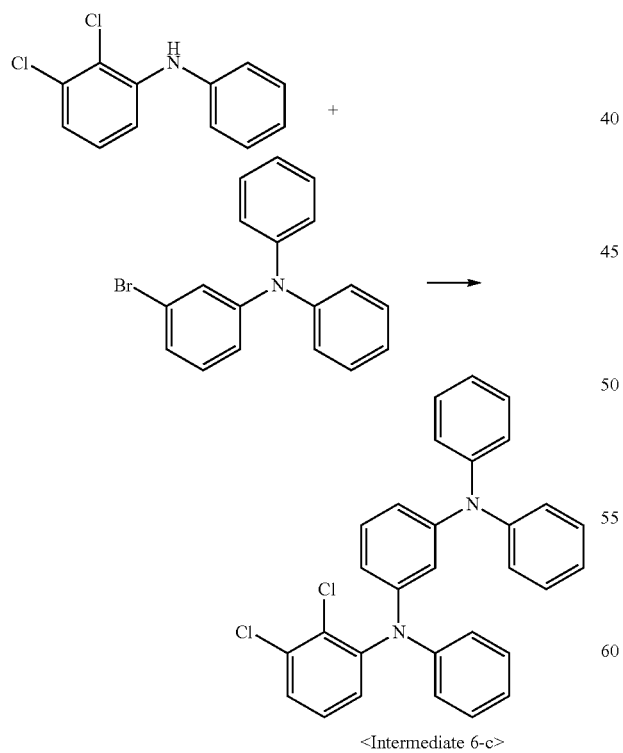

<Intermediate 6-c>

The same procedure as in Synthesis Example 5-(3) was carried out, with the exception of using Intermediate 6-a and Intermediate 6-b instead of 1-bromo-5-iodobenzene and 4-tert-butyl aniline, to afford Intermediate 6-c. (yield 78%)

Synthesis Example 6-4: Synthesis of Intermediate 6-d

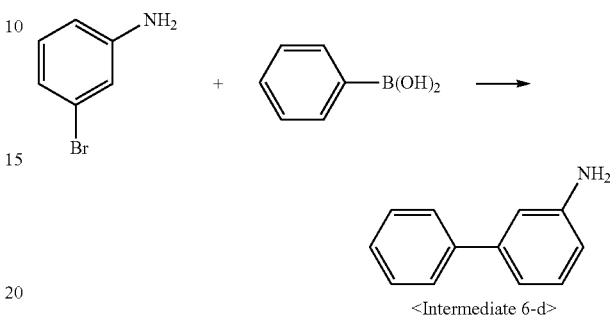

<Intermediate 6-d>

In a 1-L reactor, 3-bromoaniline (30 g, 174 mmol), phenyl boronic acid (25.5 g, 209 mmol), tetrakis(triphenylphosphine)palladium (4 g, 3 mmol), potassium carbonate (48.2 g, 349 mmol), 1,4-dioxane (150 mL), toluene (150 mL), and distilled water (90 mL) were stirred together under reflux for 4 hours. After completion of the reaction, the organic layer was concentrated in a vacuum and isolated by column chromatography to afford Intermediate 6-d (24 g, yield 80%).

Synthesis Example 6-5: Synthesis of Intermediate 6-e

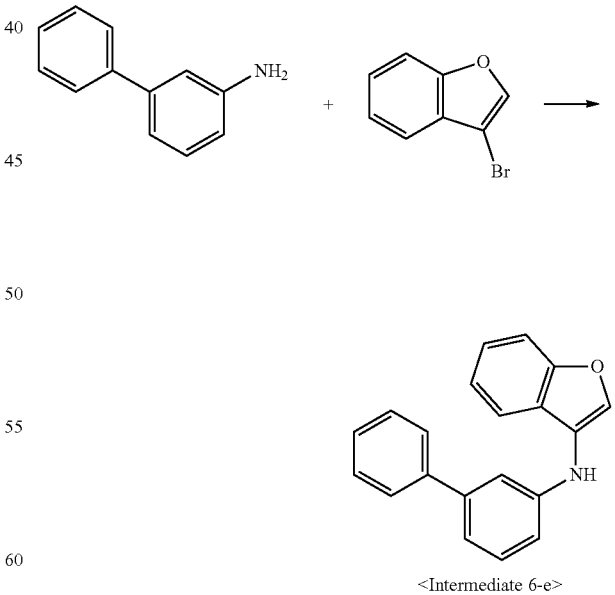

<Intermediate 6-e>

The same procedure as in Synthesis Example 5-(3) was carried out, with the exception of using 3-bromobenzofuran and Intermediate 6-d instead of 1-bromo-5-iodobenzene and 4-tert-butyl aniline, to afford Intermediate 6-e. (yield 68%)

Synthesis Example 6-6: Synthesis of Intermediate 6-f

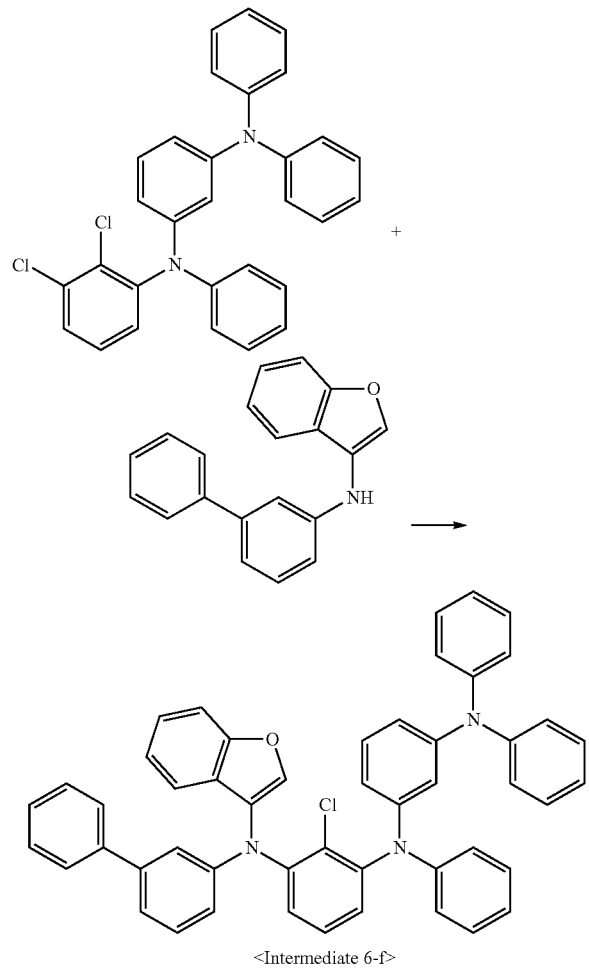

<Intermediate 6-f>

The same procedure as in Synthesis Example 5-(4) was carried out, with the exception of using Intermediate 6-e and Intermediate 6-c instead of Intermediate 5-c and 3-bromobenzothiophene, respectively, to afford Intermediate 6-f. (yield 68%)

Synthesis Example 6-7: Synthesis of BD 3

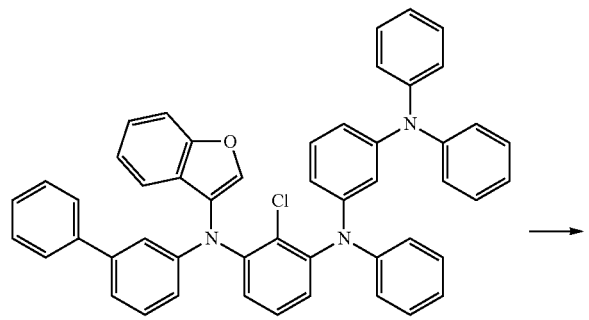

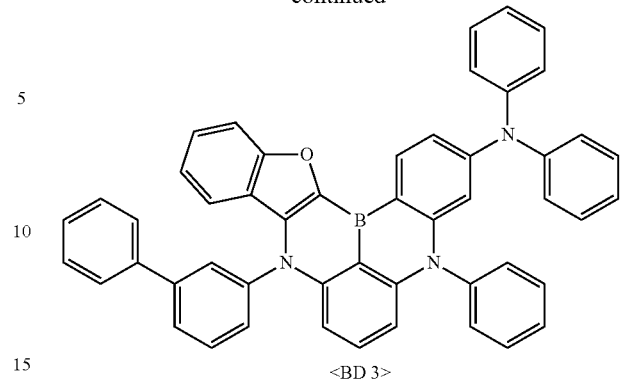

<BD 3>

In a 250-mL reactor, Intermediate 6-f (21 g, 37 mmol) and tert-butylbenzene were put. At −78° C., tert-butyl lithium (42.4 mL, 74 mmol) was dropwise added, followed by stirring at 60° C. for 3 hours. Then, pentane was removed by blowing nitrogen into the reactor. At −78° C., boron tribromide (7.1 mL, 74 mmol) was dropwise added before stirring at room temperature for 1 hour. N, N-diisopropylethyl amine (6 g, 74 mmol) was dropwise added at 0° C. before stirring at 120° C. for 2 hours. After completion of the reaction, an aqueous sodium acetate solution was added and stirred. The reaction mixture was extracted with ethylacetate, and the organic layer thus formed was concentrated and isolated by column chromatography to afford BD 3 (2.0 g, yield 17%).

MS (MALDI-TOF): m/z 703.28 [M$^+$]

Examples 1-24: Fabrication of Organic Light-Emitting Diodes

An ITO glass substrate was patterned to have a translucent area of 2 mm×2 mm and cleansed. The ITO glass was mounted in a vacuum chamber that was then set to have a base pressure of $1 \times 10^{-7}$ torr. On the ITO glass substrate, films were sequentially formed of 2-TNATA (400 Å) and HT (200 Å) in the order. Subsequently, a light-emitting layer (250 Å) was formed of a combination of host and dopant compounds (97:3 wt %) listed in Table 1, below. Then, [Chemical Formula E-1] was deposited to form an electron transport layer (300 Å) on which an electron injection layer of Liq (10 Å) was formed and then covered with an Al layer (1000 Å) to fabricate an organic light-emitting diode. The organic light-emitting diodes thus obtained were measured at 10 mA/cm$^2$ for luminescence properties

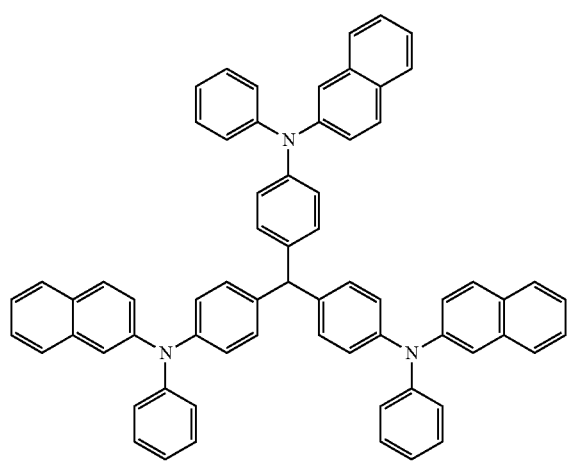

[DNTPD]

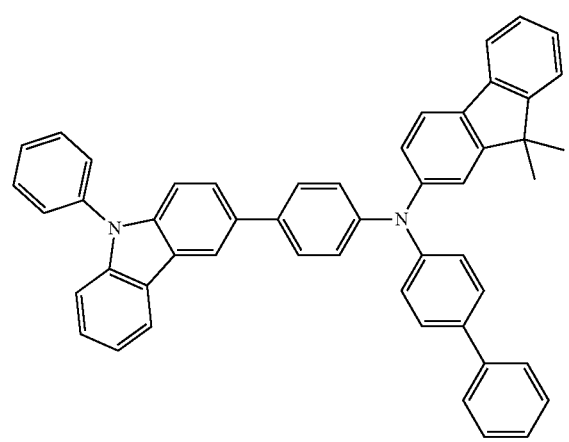

[HT]

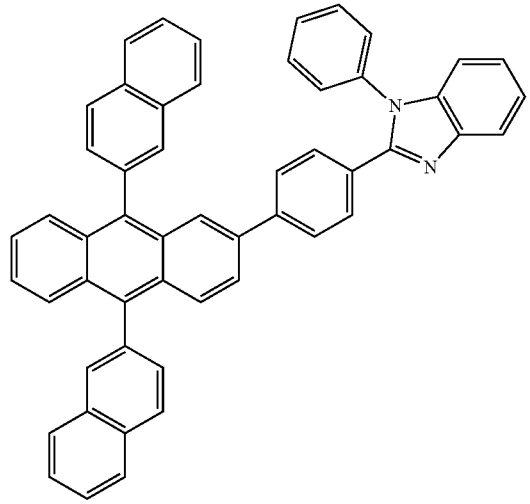

[Chemical Formula E-1]

Comparative Examples 1 to 27

Organic light emitting diodes were fabricated in the same manner as in the Examples 1 to 24, with the exception of using [BH 1] to [BH 9] compounds instead of the host compounds of Examples 1 to 24. The luminescence of the organic light-emitting diodes thus obtained was measured at 10 mA/cm$^2$, and the measurements are summarized in Table 2, below.

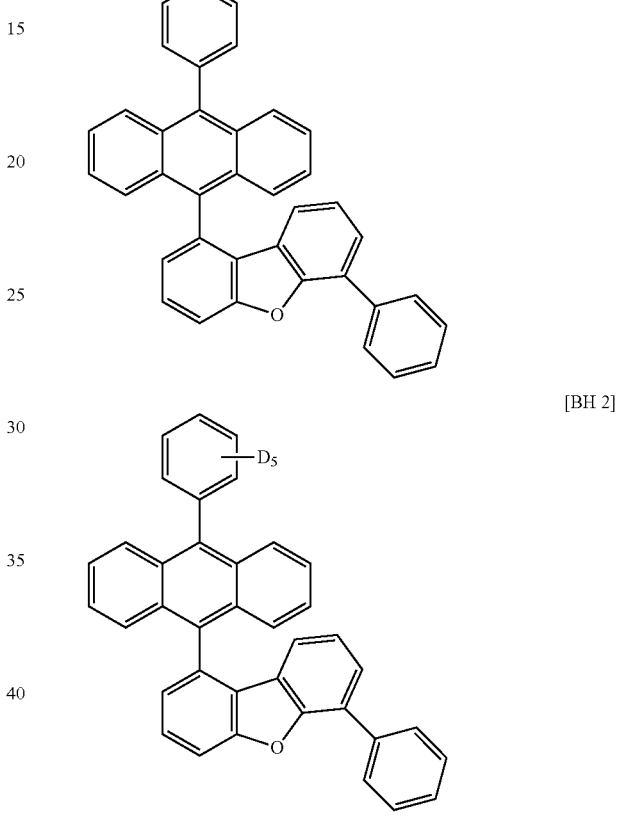

[BH 1]

[BH 2]

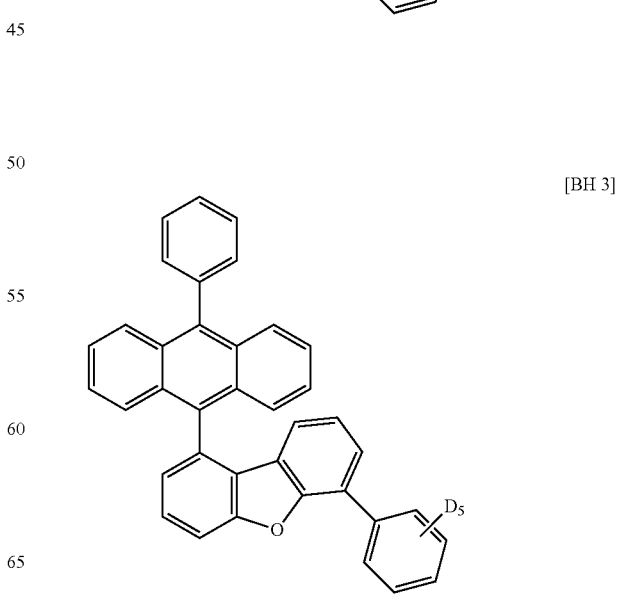

[BH 3]

[BH 4]
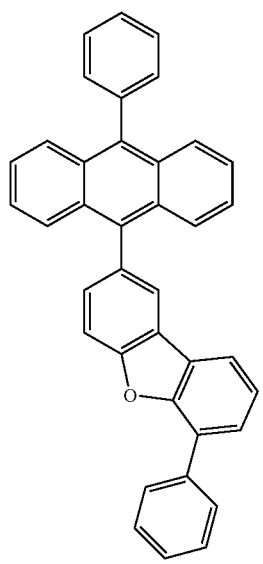
[BH 5]
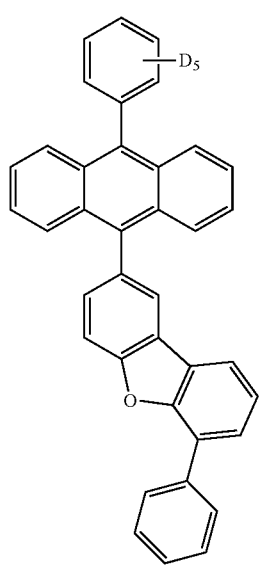
[BH 6]
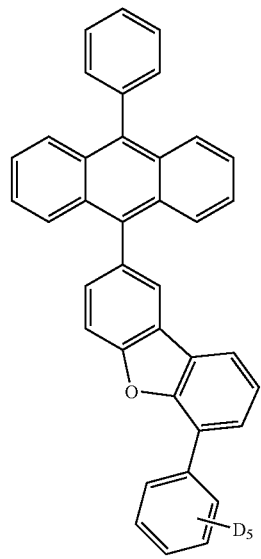
[BH 7]
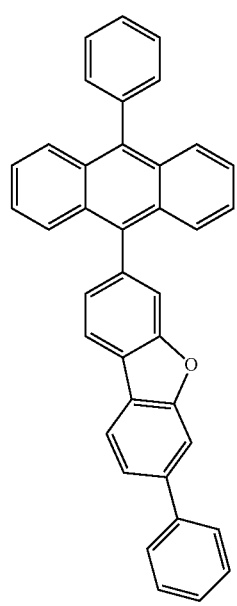

-continued

[BH 8]

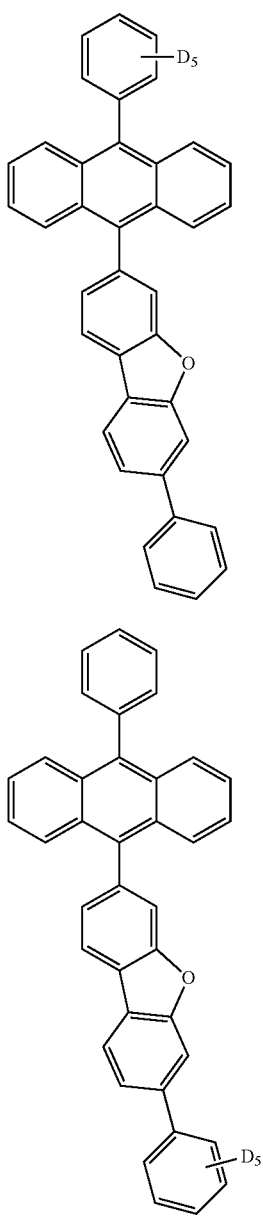

[BH 9]

TABLE 1

| | Host | Dopant | EQE | T97 |
|---|---|---|---|---|
| Ex. 1 | Compound 1 | BD1 | 10.4 | 130 |
| Ex. 2 | Compound 10 | BD1 | 10.2 | 125 |
| Ex. 3 | Compound 21 | BD1 | 10.2 | 118 |
| Ex. 4 | Compound 1 | BD2 | 10.4 | 173 |
| Ex. 5 | Compound 10 | BD2 | 10.3 | 166 |
| Ex. 6 | Compound 21 | BD2 | 10.2 | 157 |
| Ex. 7 | Compound 5 | BD1 | 10.4 | 128 |
| Ex. 8 | Compound 14 | BD1 | 10.2 | 124 |
| Ex. 9 | Compound 24 | BD1 | 10.2 | 116 |
| Ex. 10 | Compound 5 | BD2 | 10.4 | 172 |
| Ex. 11 | Compound 14 | BD2 | 10.4 | 165 |
| Ex. 12 | Compound 24 | BD2 | 10.3 | 155 |
| Ex. 13 | Compound 1 | BD3 | 10.5 | 180 |
| Ex. 14 | Compound 5 | BD3 | 10.4 | 178 |
| Ex. 15 | Compound 10 | BD3 | 10.4 | 169 |
| Ex. 16 | Compound 14 | BD3 | 10.3 | 168 |

TABLE 1-continued

| | Host | Dopant | EQE | T97 |
|---|---|---|---|---|
| Ex. 17 | Compound 21 | BD3 | 10.3 | 161 |
| Ex. 18 | Compound 24 | BD3 | 10.2 | 159 |
| Ex. 19 | Compound 43 | BD1 | 10.4 | 156 |
| Ex. 20 | Compound 48 | BD1 | 10.4 | 143 |
| Ex. 21 | Compound 60 | BD1 | 10.3 | 136 |
| Ex. 22 | Compound 43 | BD2 | 10.5 | 207 |
| Ex. 23 | Compound 48 | BD2 | 10.4 | 190 |
| Ex. 24 | Compound 60 | BD2 | 10.4 | 182 |

TABLE 2

| | Host | Dopant | EQE | T97 |
|---|---|---|---|---|
| C. Ex. 1 | BH1 | BD1 | 10.1 | 80 |
| C. Ex. 3 | BH3 | BD1 | 10.1 | 85 |
| C. Ex. 4 | BH4 | BD1 | 10.1 | 80 |
| C. Ex. 5 | BH5 | BD1 | 10.1 | 88 |
| C. Ex. 6 | BH6 | BD1 | 10.1 | 82 |
| C. Ex. 7 | BH7 | BD1 | 10.1 | 81 |
| C. Ex. 8 | BH8 | BD1 | 10.1 | 87 |
| C. Ex. 9 | BH9 | BD1 | 10.1 | 83 |
| C. Ex. 10 | BH1 | BD2 | 10.1 | 85 |
| C. Ex. 11 | BH2 | BD2 | 10.1 | 94 |
| C. Ex. 12 | BH3 | BD2 | 10.1 | 89 |
| C. Ex. 13 | BH4 | BD2 | 10.1 | 84 |
| C. Ex. 14 | BH5 | BD2 | 10.1 | 90 |
| C. Ex. 15 | BH6 | BD2 | 10.1 | 85 |
| C. Ex. 16 | BH7 | BD2 | 10.1 | 84 |
| C. Ex. 17 | BH8 | BD2 | 10.1 | 91 |
| C. Ex. 18 | BH9 | BD2 | 10.1 | 84 |
| C. Ex. 19 | BH1 | BD3 | 10.1 | 84 |
| C. Ex. 20 | BH2 | BD3 | 10.1 | 81 |
| C. Ex. 21 | BH3 | BD3 | 10.1 | 85 |
| C. Ex. 22 | BH4 | BD3 | 10.1 | 91 |
| C. Ex. 23 | BH5 | BD3 | 10.1 | 85 |
| C. Ex. 24 | BH6 | BD3 | 10.1 | 82 |
| C. Ex. 25 | BH7 | BD3 | 10.1 | 85 |
| C. Ex. 26 | BH8 | BD3 | 10.1 | 84 |
| C. Ex. 27 | BH9 | BD3 | 10.1 | 82 |

As is understood from data of Tables 1 and 2, the compounds according to the present disclosure allowed longer lifespans, compared to anthracene compounds bearing none or less than a specific ratio of deuterium atoms, thereby finding high applicability to organic light-emitting diodes.

INDUSTRIAL APPLICABILITY

When used as hosts in a light-emitting layer, the anthracene derivatives according to the present disclosure exhibit longer lifespan properties than preexisting materials. Thus, the anthracene derivatives according to the present disclosure can impart improved properties to organic light-emitting diodes and thus are industrially applicable to organic light-emitting diodes and relevant industries.

The invention claimed is:

1. An anthracene derivative represented by the following Chemical Formula A-1:

[Chemical Formula A-1]

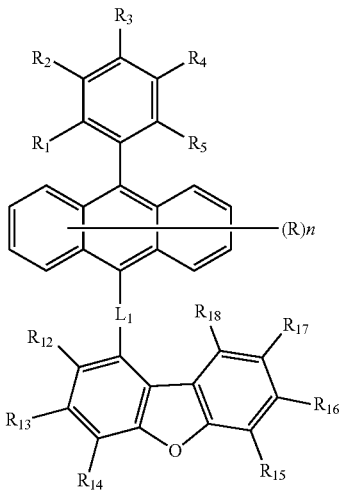

wherein,
$R_1$ to $R_5$, which are same or different, are each independently a hydrogen or deuterium atom,
R is a deuterium atom,
n is an integer of 0 to 8, with a hydrogen atom positioned on an aromatic carbon atom which is not substituted with R within the anthracene moiety,
$L_1$, which functions as a linker, is a single bond or a deuterium-substituted or unsubstituted arylene of 6 to 12 carbon atoms;
$R_{12}$ to $R_{14}$, which are same or different, are each independently a hydrogen or deuterium atom, and
$R_{15}$ to $R_{18}$, which are same or different, are each independently selected from a hydrogen atom, a deuterium atom, a deuterium-substituted or unsubstituted phenyl, a deuterium-substituted or unsubstituted biphenyl, a deuterium-substituted or unsubstituted terphenyl, a deuterium-substituted or unsubstituted naphthyl, a deuterium-substituted or unsubstituted phenanthryl, and a fluorenyl in which identical or different alkyls of 1 to 5 carbon atoms can or cannot be substituted on the carbon atom at position 9 and a deuterium atom can or cannot be substituted on each of the carbon atoms of the aromatic rings,
at least one of $R_{15}$ to $R_{18}$ being selected from a deuterium-substituted or unsubstituted phenyl, a deuterium-substituted or unsubstituted biphenyl, a deuterium-substituted or unsubstituted terphenyl, a deuterium-substituted or unsubstituted naphthyl, a deuterium-substituted or unsubstituted phenanthryl, and a fluorenyl in which identical or different alkyls of 1 to 5 carbon atoms can or cannot be substituted on the carbon atom at position 9 and a deuterium atom can or cannot be substituted on each of the carbon atoms of the aromatic rings,
wherein the anthracene derivative has a degree of deuteration of 30% or more (percentages of all deuterium atoms bonded directly to carbon atoms of the anthracene derivative relative to a sum of all deuterium and hydrogen atoms bonded directly to carbon atoms of the anthracene derivative).

2. The anthracene derivative of claim 1, wherein n is 0 (zero).

3. The anthracene derivative of claim 1, wherein $R_1$ to $R_5$ are each a deuterium atom.

4. The anthracene derivative of claim 1, wherein $L_1$ is a single bond or a deuterium-substituted or unsubstituted phenylene.

5. The anthracene derivative of claim 4, wherein $L_1$ is a single bond.

6. The anthracene derivative of claim 1, wherein only one of $R_{15}$ to $R_{18}$ is selected from a deuterium-substituted or unsubstituted phenyl, a deuterium-substituted or unsubstituted biphenyl, a deuterium-substituted or unsubstituted terphenyl, a deuterium-substituted or unsubstituted naphthyl, a deuterium-substituted or unsubstituted phenanthryl, and a fluorenyl in which identical or different alkyls of 1 to 5 carbon atoms can or cannot be substituted on the carbon atom at position 9 and a deuterium atom can or cannot be substituted on each of the carbon atoms of the aromatic rings.

7. The anthracene derivative of claim 1, wherein the anthracene derivative has a degree of deuteration of 35% or higher.

8. The anthracene derivative of claim 7, wherein the anthracene derivative has a degree of deuteration of 40% or higher.

9. The anthracene derivative of claim 1, wherein the anthracene derivative is any one selected from the group compounds represented by [Compound 1] to [Compound 9], [Compound 43] to [Compound 45], [Compound 55] to [Compound 56], [Compound 60] to [Compound 61], and [Compound 65]:

<Compound 1>

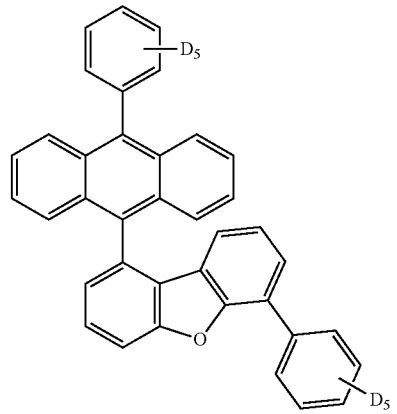

<Compound 2>

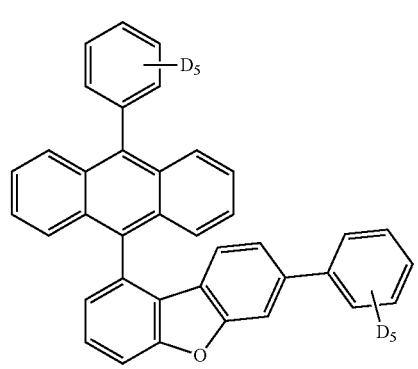

-continued
<Compound 3>
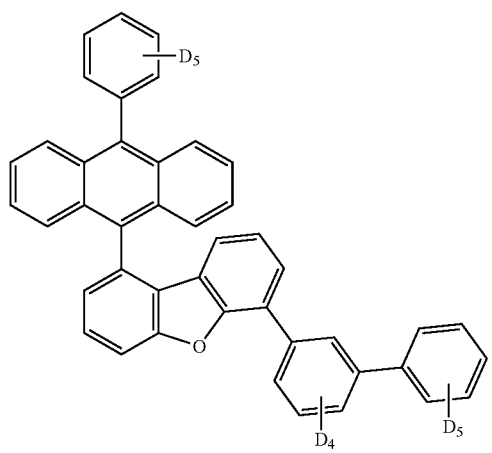
<Compound 4>
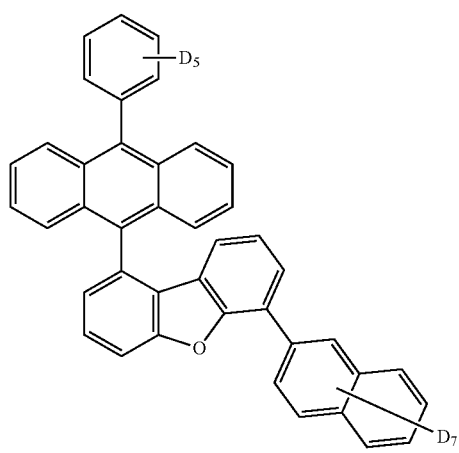
<Compound 5>
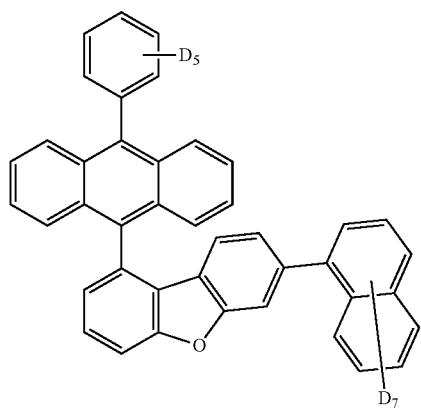
-continued
<Compound 6>
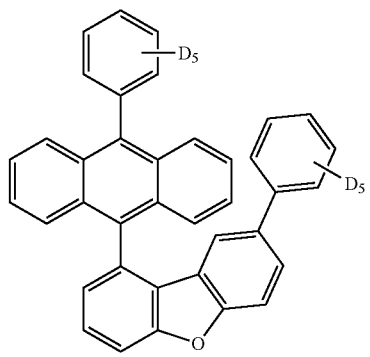
<Compound 7>
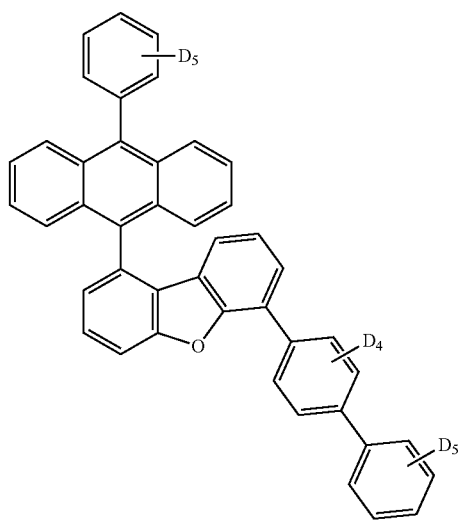
<Compound 8>
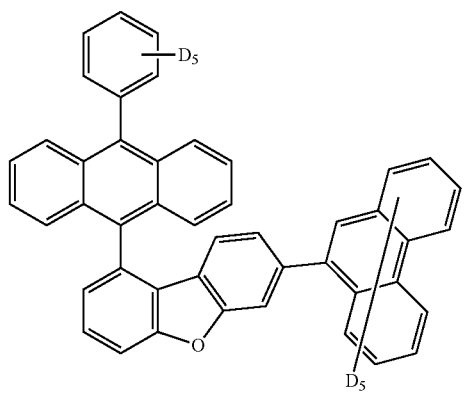

<Compound 9>
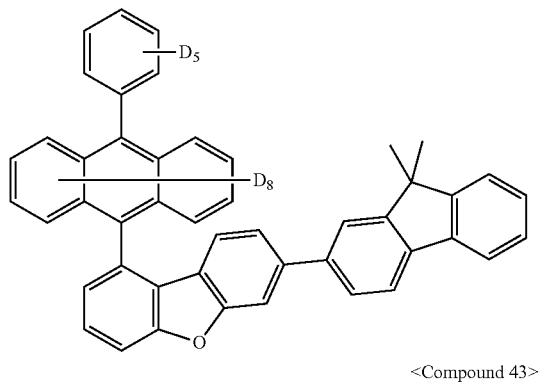
<Compound 43>
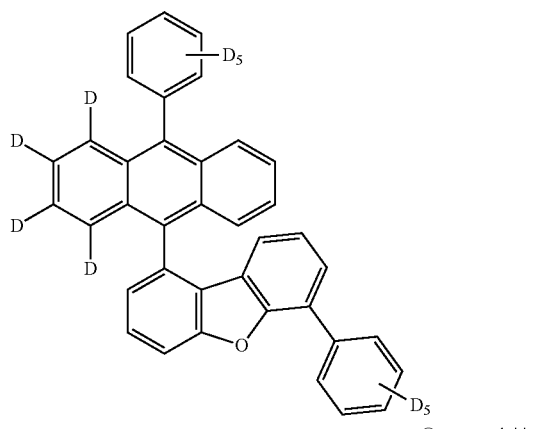
<Compound 44>
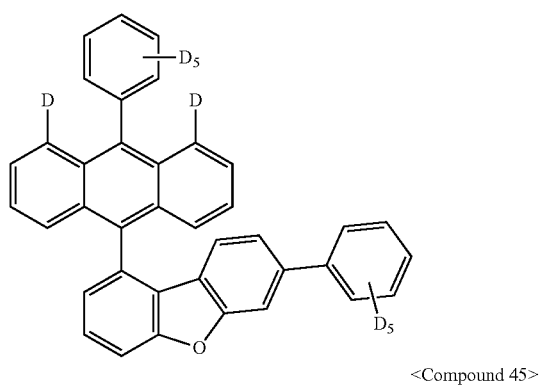
<Compound 45>
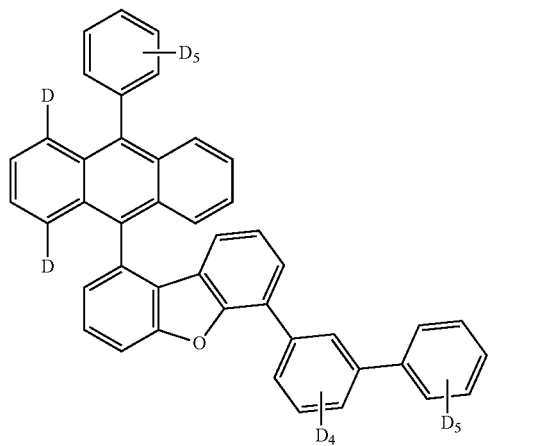
<Compound 55>
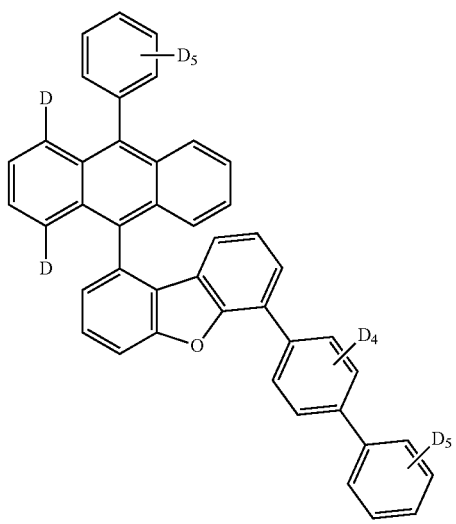
<Compound 56>
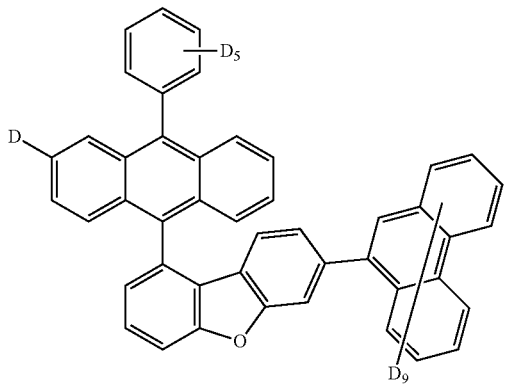
<Compound 60>
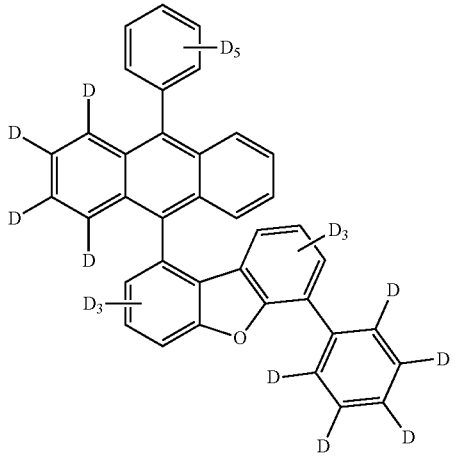

-continued

<Compound 61>

<Compound 65>

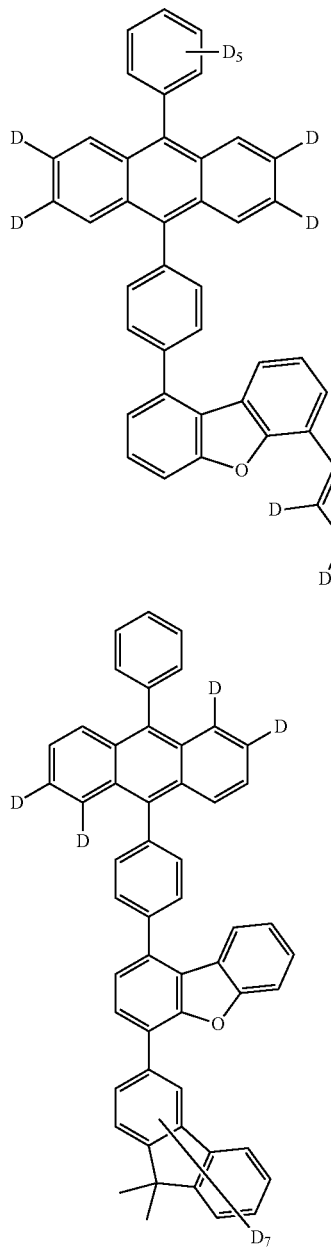

10. An organic light-emitting diode, comprising:
a first electrode; a second electrode facing the first electrode; and
an organic layer disposed between the first electrode and the second electrode,
wherein the organic layer includes the anthracene derivative of claim 1.

11. The organic light-emitting diode of claim 10, wherein the organic layer comprises at least one of a hole injection layer, a hole transport layer, a functional layer capable of both hole injection and hole transport, a light-emitting layer, an electron transport layer, and an electron injection layer.

12. The organic light-emitting diode of claim 11, wherein at least one selected from among the layers is deposited using a deposition process or a solution process.

13. The organic light-emitting diode of claim 10, wherein the organic layer disposed between the first electrode and the second electrode is a light-emitting layer.

14. The organic light-emitting diode of claim 13, wherein light-emitting layer further comprises a dopant and the anthracene derivative serves as a host.

15. The organic light-emitting diode of claim 14, wherein the dopant comprises at least one of the compounds represented by the following Chemical Formulas 2 to 6:

[Chemical Formula 2]

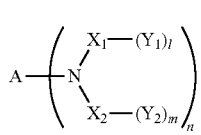

[Chemical Formula 3]

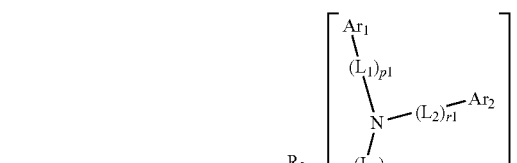
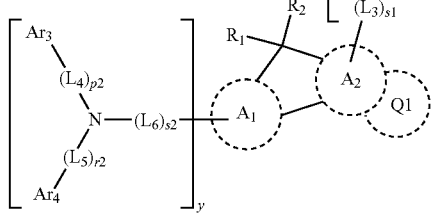

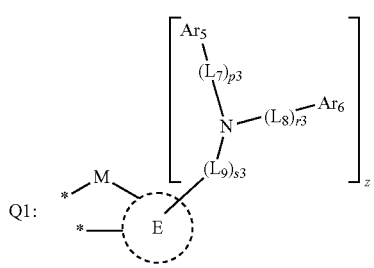

[Chemical Formula 4]

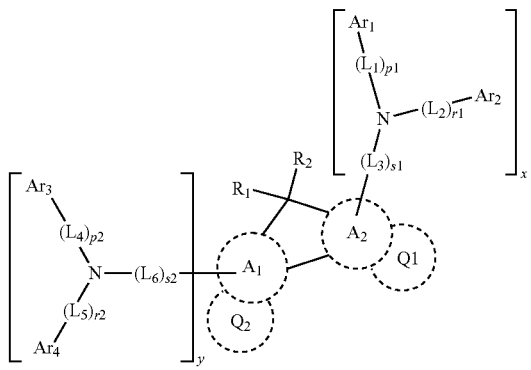

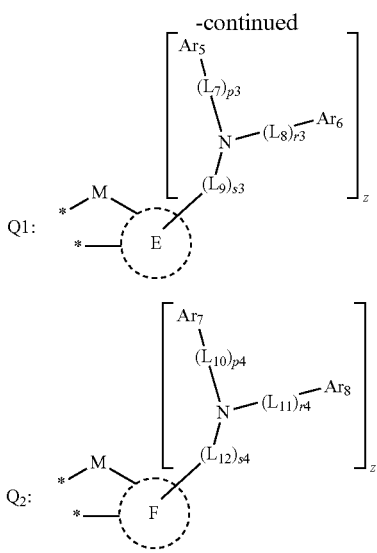

wherein,

A in Chemical Formula 2 is any one selected from a substituted or unsubstituted aryl of 5 to 50 carbon atoms, a substituted or unsubstituted heteroaryl of 3 to 50 carbon atoms bearing O, N, or S as a heteroatom, a substituted or unsubstituted arylene of 6 to 60 carbon atoms, and a substituted or unsubstituted heteroarylene of 3 to 50 carbon atoms bearing O, N, or S as a heteroatom;

in Chemical Formula 2, $X_1$ and $X_2$, which are same or different, are each independently selected from a substituted or unsubstituted arylene of 6 to 30 carbon atoms and a single bond, and can be bonded to each other;

$Y_1$ and $Y_2$, which are same or different, are each independently selected from the group consisting of a substituted or unsubstituted aryl of 6 to 24 carbon atoms, a substituted or unsubstituted heteroaryl of 2 to 24 carbon atoms, a substituted or unsubstituted alkyl of 1 to 24 carbon atoms, a substituted or unsubstituted heteroalkyl of 1 to 24 carbon atoms, a substituted or unsubstituted cycloalkyl of 3 to 24 carbon atoms, a substituted or unsubstituted alkoxy of 1 to 24 carbon atoms, a cyano, a halogen, a substituted or unsubstituted aryloxy of 6 to 24 carbon atoms, a substituted or unsubstituted alkylsilyl of 1 to 40 carbon atoms, a substituted or unsubstituted arylsilyl of 6 to 30 carbon atoms, a deuterium atom, and a hydrogen atom, and can each form a fused aliphatic or aromatic ring or a fused aliphatic or aromatic heteroring with an adjacent radical; and l and m are each an integer of 1 to 20, and n is an integer of 1 to 4;

in Chemical Formula 3 and Chemical Formula 4, $A_1$, $A_2$, E, and F, which are same or different, are each independently a substituted or unsubstituted aromatic hydrocarbon ring of 6 to 50 carbon atoms, or a substituted or unsubstituted aromatic heteroring of 2 to 40 carbon atoms wherein two adjacent carbon atoms of the aromatic ring $A_1$ and two adjacent carbon atoms of the aromatic ring $A_2$ form a 5-membered fused ring together with a carbon atom to which substituents $R_1$ and $R_2$ are bonded;

linkers $L_1$ to $L_{12}$, which are same or different, are each independently selected from a single bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

M is any one selected from N—$R_3$, $CR_4R_5$, $SiR_6R_7$, $GeR_8R_9$, O, S, and Se;

$R_1$ to $R_9$, and $Ar_1$ to $Ar_8$, which are same or different, are each independently any one of selected from a hydrogen atom, a deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a substituted or unsubstituted alkyl germanium of 1 to 30 carbon atoms, a substituted or unsubstituted aryl germanium of 1 to 30 carbon atoms, a cyano, a nitro, and a halogen, wherein $R_1$ and $R_2$ together can form a mono- or polycyclic aliphatic or aromatic ring that is a heterocyclic ring bearing a heteroatom selected from N, O, P, Si, S, Ge, Se, and Te as a ring member;

p1 to p4, r1 to r4, and s1 to s4 are each independently an integer of 1 to 3, wherein when any of them is 2 or greater, the corresponding $L_1$ to $L_{12}$ are same or different, x is an integer of 1 or 2, and y and z are same or different and are each independently an integer of 0 to 3;

$Ar_1$ can form a ring with $Ar_2$, $Ar_3$ can form a ring with $Ar_4$, $Ar_5$ can form a ring with $Ar_6$, and $Ar_7$ can form a ring with $Ar_8$;

two adjacent carbon atoms of the $A_2$ ring moiety of Chemical Formula 3 can occupy respective positions * of Structural Formula $Q_1$ to form a fused ring, and two adjacent carbon atoms of the $A_1$ ring moiety of Chemical Formula 4 can occupy respective positions * of structural Formula $Q_2$ to form a fused ring, and two adjacent carbon atoms of the $A_2$ ring moiety of Chemical Formula 4 can occupy respective positions * of Structural Formula $Q_1$ to form a fuse ring;

[Chemical Formula 5]

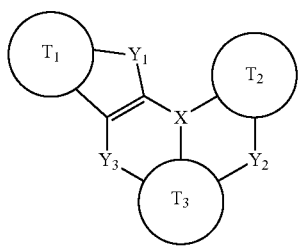

[Chemical Formula 6]

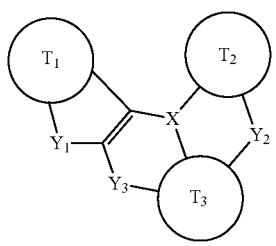

wherein,

X is any one selected from B, P, and P=O, $T_1$ to $T_3$, which are same or different, are each independently a substituted or unsubstituted aromatic hydrocarbon ring of 6 to 50 carbon atoms, or a substituted or unsubstituted heteroaromatic ring of 2 to 50 carbon atoms, and $Y_1$ to $Y_3$, which are same or different, are each independently any one selected from N—$R_{21}$, $CR_{22}R_{23}$, O, S, Se, and $SiR_{24}R_{25}$, wherein $R_{21}$ to $R_{25}$, which are same or different, are each independently any one selected from a hydrogen atom, a deuterium atom, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a nitro, a cyano, and a halogen, at least one of $R_{21}$ to $R_{25}$ can be connected to at least one of $T_1$ to $T_3$ to form an additional mono- or polycyclic aliphatic or aromatic ring, and $R_{22}$ can be connected to $R_{23}$ to form an additional mono- or polycyclic aliphatic or aromatic ring, and $R_{24}$ can be connected to $R_{25}$ to form an additional mono- or polycyclic aliphatic or aromatic ring.

16. The organic light-emitting diode of claim 10, wherein the organic light-emitting diode is used for a device selected from among a flat display device; a flexible display device; a monochrome or grayscale flat illumination; and a monochrome or grayscale flexible illumination device.

* * * * *